United States Patent
de Juan, Jr. et al.

(10) Patent No.: US 9,395,558 B2
(45) Date of Patent: Jul. 19, 2016

(54) METHODS AND APPARATUS TO IDENTIFY EYE COVERINGS FOR VISION

(75) Inventors: Eugene de Juan, Jr., San Francisco, CA (US); Yair Alster, Palo Alto, CA (US); Cary J. Reich, Los Gatos, CA (US); Ashley Tuan, Menlo Park, CA (US); Angela K MacFarlane, Menlo Park, CA (US); Matt Clarke, Menlo Park, CA (US); Brian Levy, New York, NY (US)

(73) Assignee: NexisVision, Inc., Menlo Park, CA (US)

( * ) Notice: Subject to any disclaimer, the term of this patent is extended or adjusted under 35 U.S.C. 154(b) by 0 days.

(21) Appl. No.: 13/885,135

(22) PCT Filed: Oct. 25, 2011

(86) PCT No.: PCT/US2011/057755
§ 371 (c)(1),
(2), (4) Date: Oct. 21, 2013

(87) PCT Pub. No.: WO2012/061160
PCT Pub. Date: May 10, 2012

(65) Prior Publication Data
US 2014/0028979 A1    Jan. 30, 2014

Related U.S. Application Data

(60) Provisional application No. 61/406,504, filed on Oct. 25, 2010, provisional application No. 61/480,231, filed on Apr. 28, 2011.

(51) Int. Cl.
*A61B 3/00* (2006.01)
*G02C 7/04* (2006.01)
(Continued)

(52) U.S. Cl.
CPC . *G02C 7/047* (2013.01); *A61B 3/18* (2013.01); *A61F 9/00804* (2013.01);
(Continued)

(58) Field of Classification Search
CPC ... A61F 2/142; A61F 2/14; A61F 2250/0067; A61F 9/04; G02C 7/04; G02C 7/047
USPC ................. 351/247; 623/5.11, 5.16
See application file for complete search history.

(56) References Cited

U.S. PATENT DOCUMENTS 2,641,161 A   6/1953   Silverstein
3,246,941 A   4/1966   Moss
(Continued)

FOREIGN PATENT DOCUMENTS

CA   993401 A1   7/1976
CA   2174967 C   5/1995
(Continued)

OTHER PUBLICATIONS

International Preliminary Report for EP 98936282.7, mailed on Mar. 26, 2004, 54 pages.
(Continued)

*Primary Examiner* — Mahidere Sahle

(57) ABSTRACT

Methods and apparatus can fit coverings to treat eyes. The covering can be identified so as to provide improved flow of tear liquid under the covering. The covering can be identified based on an inner corneal curvature and an outer corneal curvature and one or more of a limbus sag height or a conjunctival sag height. The covering may form a chamber when placed on the eye to pump tear liquid under at least a portion of the covering. The covering may comprise an outer portion with rigidity to resist movement on the cornea and an inner portion to contact the cornea and provide an environment for epithelial regeneration. The covering may comprise a material having high oxygen permeability, for example silicone, with a wettable coating disposed on at least an upper surface of the coating.

31 Claims, 58 Drawing Sheets

(51) Int. Cl.
*A61B 3/18* (2006.01)
*G02C 7/02* (2006.01)
*A61F 9/008* (2006.01)
*A61B 3/10* (2006.01)
*A61B 3/107* (2006.01)
*A61F 9/04* (2006.01)

(52) U.S. Cl.
CPC .............. *G02C 7/027* (2013.01); *A61B 3/1005* (2013.01); *A61B 3/107* (2013.01); *A61B 3/1015* (2013.01); *A61F 9/04* (2013.01); *G02C 7/04* (2013.01)

(56) References Cited

U.S. PATENT DOCUMENTS

| | | |
|---|---|---|
| 3,488,111 A | 1/1970 | Isen |
| 3,489,491 A | 1/1970 | Creighton |
| 3,495,899 A | 2/1970 | Biri |
| 3,594,074 A | 7/1971 | Rosen |
| 3,619,044 A | 11/1971 | Kamath |
| 3,688,386 A | 9/1972 | Pereira |
| 3,833,786 A | 9/1974 | Brucker |
| 3,915,609 A | 10/1975 | Robinson |
| 3,944,347 A | 3/1976 | Barkdoll et al. |
| 3,973,837 A | 8/1976 | Page |
| 3,973,838 A | 8/1976 | Page |
| 4,037,866 A | 7/1977 | Price |
| 4,053,442 A | 10/1977 | Jungr et al. |
| 4,068,933 A | 1/1978 | Seiderman |
| 4,071,272 A | 1/1978 | Drilik |
| 4,121,885 A | 10/1978 | Erickson et al. |
| 4,166,255 A | 8/1979 | Graham |
| 4,171,878 A | 10/1979 | Kivaev et al. |
| 4,194,815 A | 3/1980 | Trombley |
| 4,200,320 A | 4/1980 | Durham |
| 4,208,362 A | 6/1980 | Ceichert et al. |
| 4,211,476 A | 7/1980 | Brummel et al. |
| 4,268,133 A | 5/1981 | Fischer et al. |
| 4,312,575 A | 1/1982 | Peyman et al. |
| 4,381,007 A | 4/1983 | Doss |
| 4,487,905 A | 12/1984 | Mitchell |
| 4,621,912 A | 11/1986 | Meyer |
| 4,640,594 A | 2/1987 | Berger |
| 4,666,249 A | 5/1987 | Bauman et al. |
| 4,666,267 A | 5/1987 | Wichterle |
| 4,701,288 A | 10/1987 | Cook et al. |
| 4,772,283 A | 9/1988 | White |
| 4,806,382 A | 2/1989 | Goldberg et al. |
| 4,810,082 A | 3/1989 | Abel, Jr. |
| 4,886,350 A | 12/1989 | Wichterle |
| 4,890,911 A | 1/1990 | Sulc et al. |
| 4,909,896 A | 3/1990 | Ikushima et al. |
| 4,940,751 A | 7/1990 | Frances et al. |
| 4,943,150 A | 7/1990 | Deichert et al. |
| 4,952,045 A | 8/1990 | Stoyan |
| 4,978,481 A | 12/1990 | Janssen et al. |
| 4,981,841 A | 1/1991 | Gibson |
| 4,997,583 A | 3/1991 | Itzhak |
| 5,008,289 A | 4/1991 | Bernstein |
| 5,073,021 A | 12/1991 | Marron |
| 5,104,213 A | 4/1992 | Wolfson |
| 5,143,660 A | 9/1992 | Hamilton et al. |
| 5,152,786 A | 10/1992 | Hanna |
| 5,166,710 A | 11/1992 | Hofer et al. |
| 5,178,879 A | 1/1993 | Adekunle et al. |
| 5,191,365 A | 3/1993 | Stoyan |
| 5,213,720 A | 5/1993 | Civerchia |
| 5,236,236 A | 8/1993 | Girimont |
| 5,245,367 A | 9/1993 | Miller et al. |
| 5,246,259 A | 9/1993 | Hellenkamp et al. |
| 5,293,186 A | 3/1994 | Seden et al. |
| 5,346,491 A | 9/1994 | Oertli |
| 5,347,326 A | 9/1994 | Volk |
| 5,349,395 A | 9/1994 | Stoyan |
| 5,397,848 A | 3/1995 | Yang et al. |
| 5,428,412 A | 6/1995 | Stoyan |
| 5,433,714 A | 7/1995 | Bloomberg |
| 5,433,898 A | 7/1995 | Thakrar et al. |
| 5,434,630 A | 7/1995 | Bransome |
| 5,472,436 A | 12/1995 | Fremstad |
| 5,496,084 A | 3/1996 | Miralles Medan |
| 5,517,260 A | 5/1996 | Glady et al. |
| 5,538,301 A | 7/1996 | Yavitz et al. |
| 5,570,144 A | 10/1996 | Lofgren-Nisser |
| 5,578,332 A | 11/1996 | Hamilton et al. |
| 5,598,233 A | 1/1997 | Haralambopoulos et al. |
| 5,628,794 A | 5/1997 | Lindstrom |
| 5,632,773 A | 5/1997 | Graham et al. |
| 5,649,922 A | 7/1997 | Yavitz |
| 5,662,706 A | 9/1997 | Legerton et al. |
| 5,671,038 A | 9/1997 | Porat |
| 5,712,721 A | 1/1998 | Large |
| 5,732,990 A | 3/1998 | Yavitz et al. |
| 5,757,458 A | 5/1998 | Miller et al. |
| 5,760,100 A | 6/1998 | Nicolson et al. |
| 5,760,870 A | 6/1998 | Payor et al. |
| 5,804,263 A | 9/1998 | Goldberg et al. |
| 5,820,624 A | 10/1998 | Yavitz |
| 5,854,291 A | 12/1998 | Laughlin et al. |
| 5,869,533 A | 2/1999 | Holt |
| 5,885,597 A | 3/1999 | Botknecht et al. |
| 5,905,561 A | 5/1999 | Lee et al. |
| 5,910,512 A | 6/1999 | Conant |
| 5,923,397 A | 7/1999 | Bonafini, Jr. |
| 5,929,968 A | 7/1999 | Cotie et al. |
| 5,953,098 A | 9/1999 | Lieberman et al. |
| 5,957,921 A | 9/1999 | Mirhashemi et al. |
| 5,962,532 A | 10/1999 | Campbell et al. |
| 5,971,541 A | 10/1999 | Danker et al. |
| 5,980,040 A | 11/1999 | Xu et al. |
| 5,986,001 A | 11/1999 | Ingenito et al. |
| 6,010,219 A | 1/2000 | Stoyan |
| 6,030,974 A | 2/2000 | Schwartz et al. |
| 6,036,314 A | 3/2000 | Wolfson |
| 6,036,688 A | 3/2000 | Edwards |
| 6,048,855 A | 4/2000 | De Lacharriere et al. |
| 6,075,066 A | 6/2000 | Matsuda et al. |
| 6,092,898 A | 7/2000 | De Juan et al. |
| 6,099,121 A | 8/2000 | Chapman et al. |
| 6,217,171 B1 | 4/2001 | Auten et al. |
| 6,244,709 B1 | 6/2001 | Vayntraub et al. |
| 6,248,788 B1 | 6/2001 | Robbins et al. |
| 6,325,509 B1 | 12/2001 | Hodur et al. |
| 6,340,229 B1 | 1/2002 | Lieberman et al. |
| 6,361,169 B1 | 3/2002 | Tung |
| 6,364,482 B1 | 4/2002 | Roffman et al. |
| 6,406,145 B1 | 6/2002 | Jubin |
| 6,474,814 B1 | 11/2002 | Griffin |
| 6,520,637 B2 | 2/2003 | Hodur et al. |
| 6,541,028 B1 | 4/2003 | Kuri-Harcuch et al. |
| 6,551,307 B2 | 4/2003 | Peyman |
| 6,568,808 B2 | 5/2003 | Campin |
| 6,579,918 B1 | 6/2003 | Auten et al. |
| 6,593,370 B2 | 7/2003 | Tamura et al. |
| 6,652,095 B2 | 11/2003 | Tung |
| 6,659,607 B2 | 12/2003 | Miyamura et al. |
| 6,726,322 B2 | 4/2004 | Andino et al. |
| 6,726,684 B1 | 4/2004 | Woloszko et al. |
| 6,779,888 B2 | 8/2004 | Marmo |
| 6,843,563 B2 | 1/2005 | Richardson |
| 6,849,671 B2 | 2/2005 | Steffen et al. |
| 6,951,894 B1 | 10/2005 | Nicolson et al. |
| 7,018,039 B2 | 3/2006 | Legerton et al. |
| 7,025,455 B2 | 4/2006 | Roffman |
| 7,080,905 B2 | 7/2006 | Marmo et al. |
| 7,097,301 B2 | 8/2006 | Legerton et al. |
| 7,104,648 B2 | 9/2006 | Dahi et al. |
| 7,150,529 B2 | 12/2006 | Legerton et al. |
| 7,163,292 B2 | 1/2007 | Dahi et al. |
| 7,193,124 B2 | 3/2007 | Coffee |
| 7,216,974 B2 | 5/2007 | Meyers et al. |
| 7,249,849 B2 | 7/2007 | Marmo et al. |
| 7,270,412 B2 | 9/2007 | Legerton et al. |

(56) References Cited

U.S. PATENT DOCUMENTS

| | | |
|---|---|---|
| 7,322,694 B2 | 1/2008 | Dahi et al. |
| 7,329,001 B2 | 2/2008 | Benrashid et al. |
| 7,338,160 B2 | 3/2008 | Lieberman et al. |
| 7,360,890 B2 | 4/2008 | Back |
| 7,377,637 B2 | 5/2008 | Legerton et al. |
| 7,401,922 B2 | 7/2008 | Legerton |
| 7,404,638 B2 | 7/2008 | Miller et al. |
| 7,461,937 B2 | 12/2008 | Steffen et al. |
| 7,491,350 B2 | 2/2009 | Silvestrini |
| 7,530,689 B2 | 5/2009 | Berke |
| 7,537,339 B2 | 5/2009 | Legerton et al. |
| 7,543,936 B2 | 6/2009 | Legerton et al. |
| 7,559,649 B2 | 7/2009 | Cotie et al. |
| 7,585,074 B2 | 9/2009 | Dahi et al. |
| 7,594,725 B2 | 9/2009 | Legerton et al. |
| 7,628,810 B2 | 12/2009 | Christie et al. |
| 7,682,020 B2 | 3/2010 | Berke |
| 7,695,135 B1 | 4/2010 | Rosenthal |
| 7,699,465 B2 | 4/2010 | Dootjes et al. |
| 7,717,555 B2 | 5/2010 | Legerton et al. |
| 7,735,997 B2 | 6/2010 | Muckenhirn |
| 7,748,844 B2 | 7/2010 | Lai |
| 7,762,668 B2 | 7/2010 | Dai et al. |
| 7,828,432 B2 | 11/2010 | Meyers et al. |
| 7,859,769 B2 | 12/2010 | Zalevsky |
| 7,976,577 B2 | 7/2011 | Silvestrini |
| 7,984,988 B2 | 7/2011 | Berke |
| 8,137,344 B2 | 3/2012 | Jia et al. |
| 8,201,941 B2 | 6/2012 | Choo et al. |
| 8,459,793 B2 | 6/2013 | De Juan, Jr. et al. |
| 8,591,025 B1 | 11/2013 | De Juan, Jr. et al. |
| 8,678,584 B2 | 3/2014 | De Juan, Jr. et al. |
| 2002/0095199 A1 | 7/2002 | West, Jr. et al. |
| 2002/0164484 A1 | 11/2002 | Jiang et al. |
| 2004/0015163 A1 | 1/2004 | Buysse |
| 2004/0088050 A1 | 5/2004 | Norrby et al. |
| 2004/0141150 A1 | 7/2004 | Roffman et al. |
| 2004/0170666 A1 | 9/2004 | Keates et al. |
| 2004/0184158 A1 | 9/2004 | Shadduck |
| 2004/0212779 A1 | 10/2004 | Dahi et al. |
| 2005/0033420 A1 | 2/2005 | Christie et al. |
| 2005/0107775 A1 | 5/2005 | Huang et al. |
| 2005/0213030 A1* | 9/2005 | Meyers ............... 351/167 |
| 2005/0259221 A1 | 11/2005 | Marmo |
| 2005/0288196 A1 | 12/2005 | Horn |
| 2006/0077581 A1 | 4/2006 | Schwiegerling |
| 2006/0083773 A1 | 4/2006 | Myung |
| 2006/0100617 A1 | 5/2006 | Boukhny |
| 2006/0132707 A1 | 6/2006 | Tung |
| 2006/0152673 A1 | 7/2006 | Cotie et al. |
| 2006/0197909 A1 | 9/2006 | Legerton |
| 2006/0197910 A1 | 9/2006 | Legerton |
| 2006/0238712 A1 | 10/2006 | Dahi |
| 2006/0241751 A1 | 10/2006 | Marmo |
| 2006/0250576 A1 | 11/2006 | Legerton et al. |
| 2006/0256283 A1 | 11/2006 | Legerton |
| 2006/0256284 A1 | 11/2006 | Dahi |
| 2006/0285072 A1 | 12/2006 | Dahi |
| 2006/0290882 A1 | 12/2006 | Meyers et al. |
| 2007/0013869 A1 | 1/2007 | Dahi |
| 2007/0014760 A1 | 1/2007 | Peyman |
| 2007/0037898 A1 | 2/2007 | Phelan et al. |
| 2007/0046894 A1 | 3/2007 | Muckenhirn |
| 2007/0106394 A1 | 5/2007 | Chen |
| 2007/0129720 A1 | 6/2007 | Demarais et al. |
| 2007/0182920 A1 | 8/2007 | Back et al. |
| 2007/0232755 A1 | 10/2007 | Matsushita et al. |
| 2007/0242216 A1 | 10/2007 | Dootjes et al. |
| 2007/0244559 A1 | 10/2007 | Shiuey |
| 2007/0273834 A1 | 11/2007 | Legerton |
| 2008/0039832 A1 | 2/2008 | Palanker et al. |
| 2008/0074611 A1 | 3/2008 | Meyers et al. |
| 2008/0100796 A1 | 5/2008 | Pruitt et al. |
| 2008/0243156 A1 | 10/2008 | John |
| 2008/0287915 A1 | 11/2008 | Rosenthal et al. |
| 2008/0291391 A1 | 11/2008 | Meyers et al. |
| 2009/0033864 A1 | 2/2009 | Shone et al. |
| 2009/0096987 A1 | 4/2009 | Lai et al. |
| 2009/0237612 A1 | 9/2009 | Cotie et al. |
| 2009/0303442 A1 | 12/2009 | Choo et al. |
| 2010/0036488 A1 | 2/2010 | De Juan, Jr. et al. |
| 2010/0060849 A1 | 3/2010 | Hibino |
| 2010/0128224 A1 | 5/2010 | Legerton |
| 2010/0157250 A1 | 6/2010 | Berke |
| 2010/0208196 A1 | 8/2010 | Benrashid et al. |
| 2010/0271589 A1 | 10/2010 | Legerton et al. |
| 2011/0034854 A1 | 2/2011 | Neuberger et al. |
| 2011/0208300 A1 | 8/2011 | De Juan, Jr. et al. |
| 2012/0105804 A1 | 5/2012 | Legerton |
| 2012/0113386 A1 | 5/2012 | Back |
| 2012/0169994 A1 | 7/2012 | Matsushita et al. |
| 2012/0310133 A1 | 12/2012 | De Juan, Jr. et al. |
| 2012/0327362 A1 | 12/2012 | Doraiswamy et al. |
| 2013/0025606 A1 | 1/2013 | De Juan, Jr. et al. |
| 2013/0066283 A1 | 3/2013 | de Juan, Jr. et al. |
| 2013/0070200 A1 | 3/2013 | De Juan, Jr. et al. |
| 2013/0077044 A1 | 3/2013 | De Juan, Jr. et al. |
| 2013/0201442 A1 | 8/2013 | Back |
| 2013/0201443 A1 | 8/2013 | Back et al. |
| 2013/0201454 A1 | 8/2013 | Back |
| 2013/0208236 A1 | 8/2013 | McCabe et al. |
| 2013/0208237 A1 | 8/2013 | Hawke et al. |
| 2013/0222761 A1 | 8/2013 | Hansen et al. |
| 2013/0242255 A1 | 9/2013 | Caldarise et al. |
| 2013/0258276 A1 | 10/2013 | Hansen et al. |
| 2013/0278890 A1 | 10/2013 | de Juan, Jr. et al. |
| 2013/0293832 A1 | 11/2013 | de Juan, Jr. et al. |
| 2014/0069438 A1 | 3/2014 | de Juan, Jr. et al. |
| 2014/0069439 A1 | 3/2014 | de Juan, Jr. et al. |
| 2014/0155800 A1 | 6/2014 | de Juan, Jr. et al. |
| 2014/0251347 A1 | 9/2014 | de Juan, Jr. et al. |

FOREIGN PATENT DOCUMENTS

| | | |
|---|---|---|
| DE | 3143839 A1 | 5/1983 |
| EP | 42679 A2 | 12/1981 |
| EP | 0434205 A2 | 6/1991 |
| EP | 0574352 A1 | 12/1993 |
| EP | 0378512 A3 | 2/1995 |
| EP | 0378512 B1 | 2/1995 |
| EP | 638416 A1 | 11/1995 |
| EP | 0985157 B1 | 12/1998 |
| EP | 1664907 A1 | 6/2006 |
| GB | 2107895 A | 5/1983 |
| JP | 55-101125 | 7/1980 |
| JP | 57-27456 | 6/1982 |
| JP | 57-27457 | 6/1982 |
| JP | 2661909 B2 | 10/1997 |
| JP | 11-151263 A | 6/1999 |
| JP | 11-249048 A | 9/1999 |
| JP | 2004-504105 A | 2/2004 |
| WO | 90/14083 A1 | 11/1990 |
| WO | 92/07617 A1 | 5/1992 |
| WO | 93/07840 A1 | 4/1993 |
| WO | 94/05225 A1 | 3/1994 |
| WO | 95/13764 A1 | 5/1995 |
| WO | 95/15134 A1 | 6/1995 |
| WO | 96/27816 A1 | 9/1996 |
| WO | 97/19381 A1 | 5/1997 |
| WO | 98/03267 A1 | 1/1998 |
| WO | 98/54603 A1 | 12/1998 |
| WO | 99/30560 A1 | 6/1999 |
| WO | 99/43354 A2 | 9/1999 |
| WO | 99/43354 A3 | 9/1999 |
| WO | 99/46631 A1 | 9/1999 |
| WO | 00/09042 A1 | 2/2000 |
| WO | 2011/050327 A1 | 4/2001 |
| WO | 01/68082 A1 | 9/2001 |
| WO | 02/06883 A2 | 1/2002 |
| WO | 02/10841 A1 | 2/2002 |
| WO | 02/068008 A1 | 9/2002 |
| WO | 2003/097759 A1 | 11/2003 |
| WO | 2004/068196 A1 | 8/2004 |
| WO | 2004/097502 A1 | 11/2004 |

(56) References Cited

FOREIGN PATENT DOCUMENTS

| | | |
|---|---|---|
| WO | 2004/109368 A2 | 12/2004 |
| WO | 2005/079290 A2 | 9/2005 |
| WO | 2005/116729 A2 | 12/2005 |
| WO | 2006/026666 A2 | 3/2006 |
| WO | 2006/026666 A3 | 3/2006 |
| WO | 2006/113149 A2 | 10/2006 |
| WO | 2006/121591 A1 | 11/2006 |
| WO | 2006/134649 A1 | 12/2006 |
| WO | 2007/002231 A1 | 1/2007 |
| WO | 2007/044513 A1 | 4/2007 |
| WO | 2007/053297 A2 | 5/2007 |
| WO | 2007/053297 A3 | 5/2007 |
| WO | 2009/065061 A1 | 5/2009 |
| WO | 2009/073213 A1 | 6/2009 |
| WO | 2006/113149 A3 | 10/2009 |
| WO | 2009/145842 A2 | 12/2009 |
| WO | 2010/051172 A1 | 5/2010 |
| WO | 2010/144317 A1 | 12/2010 |
| WO | 2011/050365 A1 | 4/2011 |
| WO | 2012/061160 A1 | 5/2012 |
| WO | 2012/149056 A1 | 11/2012 |
| WO | 2013/184239 A1 | 12/2013 |

OTHER PUBLICATIONS

International Search Report and Written Opinion for PCT/US2013/037219, mailed on Jul. 22, 2013, 20 pages.
International Search Report and Written Opinion for PCT/US2013/059244, mailed on Nov. 18, 2013, 7 pages.
Jorge L. Alio et al. "Contact Lens Fitting to Correct Irregular Astigmatic After Corneal Refractive Surgery", Journal of Cataract & Refractive Surgery, 2002, vol. 28, No. 10, p. 1750-1757.
Notice of Allowance for U.S. Appl. No. 13/894,176, mailed on Feb. 26, 2014, 10 pages.
Non-final Office Action for U.S. Appl. No. 13/894,176, mailed on Aug. 5, 2013, 13 pages.
Non-final Office Action for U.S. Appl. No. 13/456,168, mailed on Sep. 12, 2013, 17 pages.
Notice of Allowance for U.S. Appl. No. 13/715,917, mailed on Aug. 1, 2013, 12 pages.
Notice of Allowance for U.S. Appl. No. 13/615,111, mailed on Apr. 23, 2013, 10 pages.
English translation of Japanese Office Action for Japanese Application No. 2011-502997, mailed on Jun. 14, 2013, 7 pages.
International Search Report and Written Opinion of the International Searching Authority for PCT Application No. PCT/US2010/053975, mailed on Feb. 11, 2011, 30 pages.
International Preliminary Report on Patentability for PCT Application No. PCT/US2010/053975, dated Apr. 24, 2012, 20 pages.
International Search Report and Written Opinion of the International Searching Authority for PCT Application No. PCT/US2010/053854, mailed on Mar. 1, 2011, 18 pages.
International Preliminary Report on Patentability for PCT Application No. PCT/US2010/053854, mailed on Apr. 24, 2012, 13 pages.
International Search Report and Written Opinion of the International Searching Authority for PCT Application No. PCT/US2009/002166, mailed on Nov. 19, 2009, 13 pages.
International Preliminary Report on Patentability for PCT Application No. PCT/US2009/002166, mailed onOct. 5, 2010, 5 pages.
International Search Report for PCT/US2011/57755, mailed on Feb. 7, 2012, 14 pages.
International Search Report and Written Opinion of the International Searching Authority for PCT Application No. PCT/US2012/035050, mailed on Oct. 3, 2012, 11 pages.
Bissen-Miyajima et al., "Role of the endothelial pump in flap adhesion after laser in situ keratomileusis," J Cataract Refract Surg. Sep. 2004; 30(9): pp. 1989-1992.
Bausch & Lomb Boston® Materials & Solutions Product Guide, 2009, 38 pages total.
SynergEyes, Inc., SynergEyes® A Practitioner Training, retrieved from the Internet: <http://www.fitsynergeyes.com/syn_a/synergeyesA_presentation.pdf>, 52 pages.
SynergEyes, Inc., "SynergEyes® A," [package insert, P/N 70008 Rev. I], 12 pages.
Synerg Eyes®, Inc., Product Overview of CLEARKONE® and SYNERGEYES® PS retrieved from the Internet http://www.synergeyes.com/index.html on May 29, 2012, 5 pages.
Schimmelpfenning et al., "A technique for controlled sensory denervation of the rabbit cornea", Database accession No. NLM7129102, Graefe's Archive for Clinical and Experimental Opthalmology, vol. 218, No. 6, 1982, p. 287-293. (Abstract only).
EP Office Action for Application No. 10825787.4, mailed on Aug. 12, 2014, 5 pages.
EP Search Report for Application No. 10825787.4, mailed on Jun. 18, 2013, 13 pages.
Final Office Action for U.S. Appl. No. 13/503,842, mailed on Aug. 13, 2014, 21 pages.
Non-Final Office Action for U.S. Appl. No. 13/503,842, mailed on Apr. 3, 2014, 29 pages.
Final Office Action for U.S. Appl. No. 13/555,056, mailed on Sep. 5, 2014, 23 pages.
Non-Final Office Action for U.S. Appl. No. 13/555,056, mailed on Mar. 28, 2014, 30 pages.
Notice of Allowance for U.S. Appl. No. 13/456,168, mailed on May 30, 2014, 11 pages.
Non-Final Office Action for U.S. Application No. 13/503,841, mailed on Jun. 27, 2014, 22 pages.
Notice of Allowance for U.S. Appl. No. 13/928,077, mailed on Jan. 15, 2014, 8 pages.
Japanese Office Action for Application No. 2011-502997, mailed on Jun. 3, 2013, 5 pages.
International Search Report and Written Opinion for PCT/US2014/044136, mailed on Jan. 16, 2015, 21 pages.
International Search Report and Written Opinion for PCT/US2014/064391, mailed on Jan. 26, 2015, 10 pages.
Final Office Action for U.S. Appl. No. 13/503,841, mailed on Nov. 26, 2014, 6 pages.
Non-Final Office Action for U.S. Appl. No. 14/286,605, mailed on Dec. 18, 2014, 17 pages.
International Search Report and Written Opinion for PCT/US2014/065543, mailed on Feb. 25, 2015, 18 pages.
International Search Report and Written Opinion for PCT/US2015/013006, mailed on Apr. 2, 2015, 17 pages.
U.S. Appl. No. 12/384,659, Non-Final Office Action mailed Jan. 21, 2016.
U.S. Appl. No. 13/503,841, Non-Final Office Action mailed Nov. 16, 2015.
U.S. Appl. No. 13/503,842, Non-Final Office Action mailed Nov. 25, 2015.
U.S. Appl. No. 14/539,698, Notice of Allowance mailed Jan. 21, 2016.
U.S. Appl. No. 14/793,965, Non-Final Office Action mailed Dec. 31, 2015.

* cited by examiner

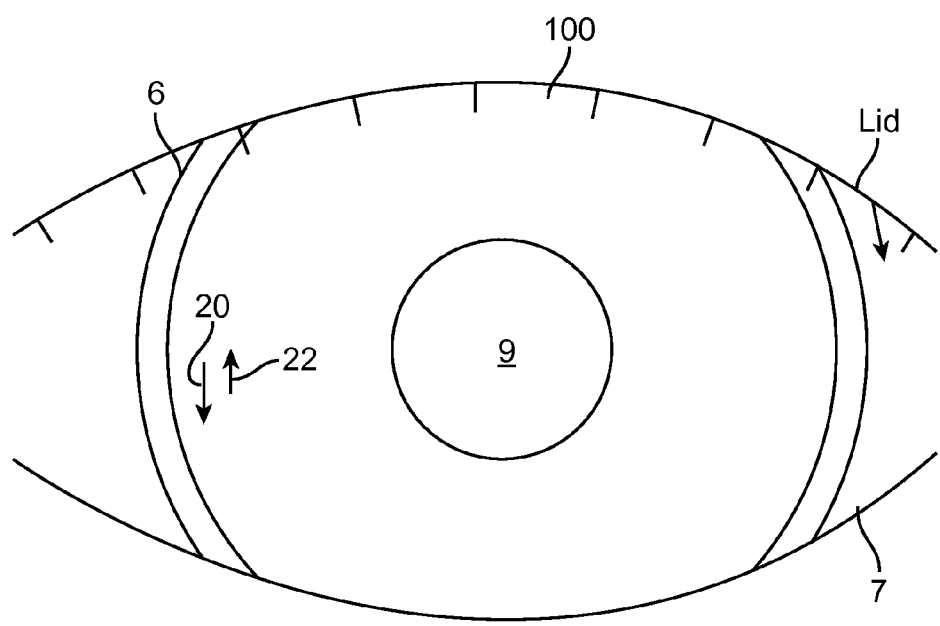
FIG. 1A1

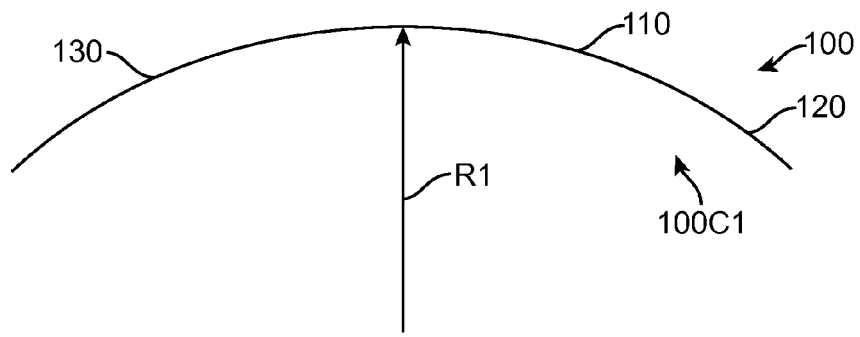
FIG. 1B1
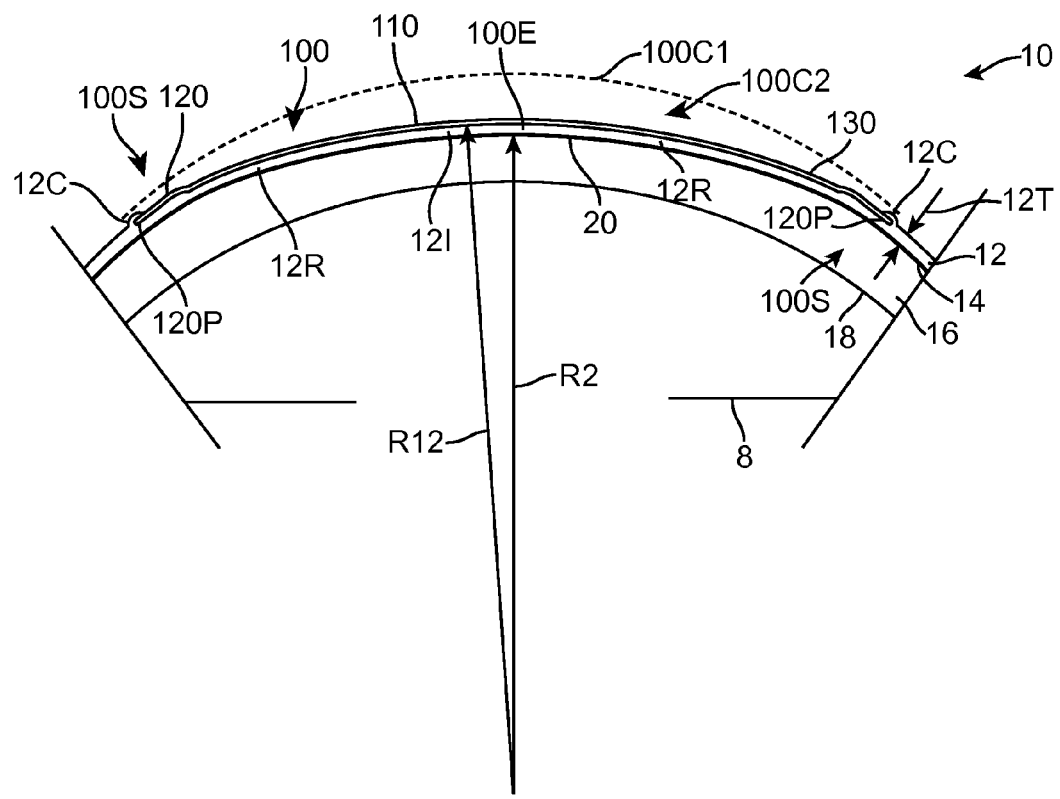
FIG. 1B2

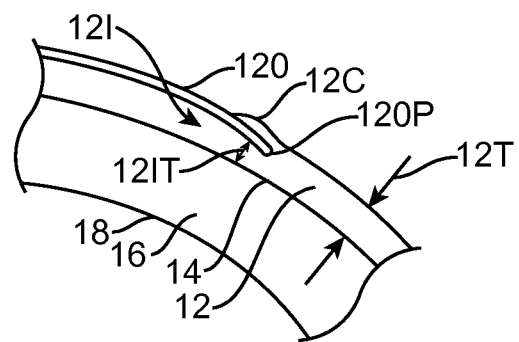
FIG. 1B2A
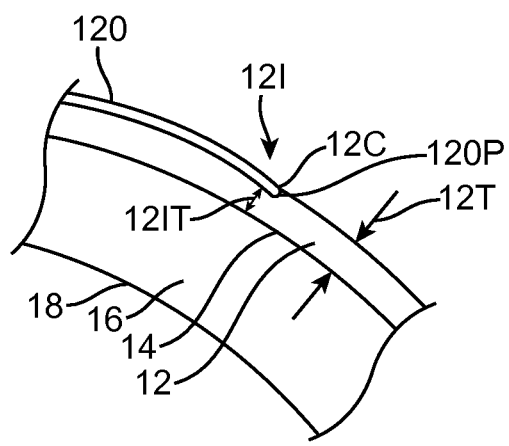
FIG. 1B2B

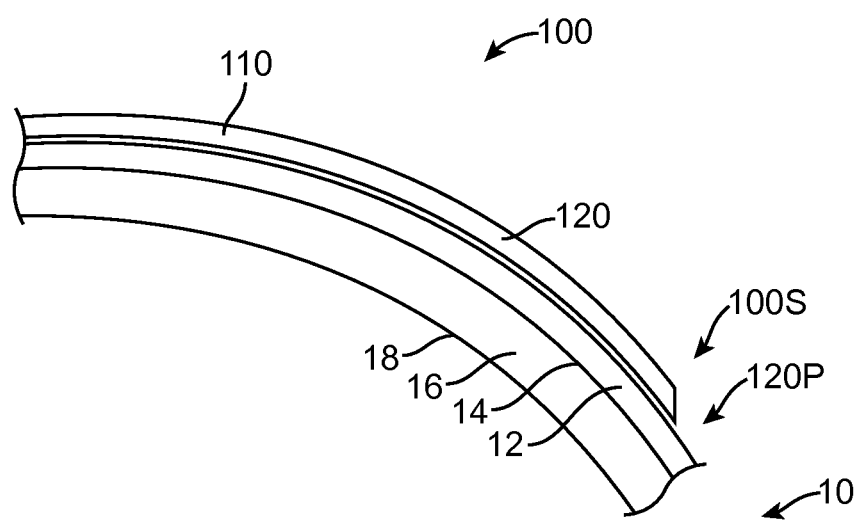
FIG. 1B2C

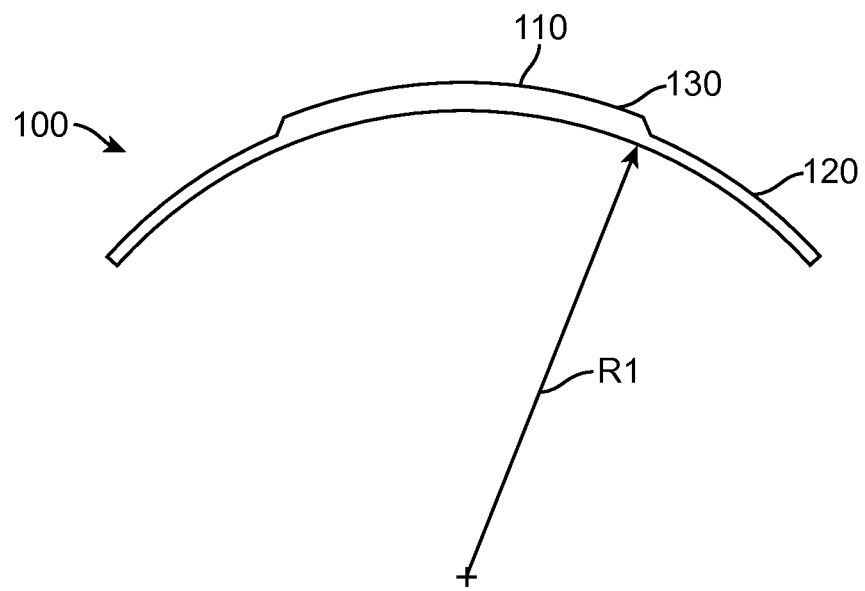
FIG. 1C
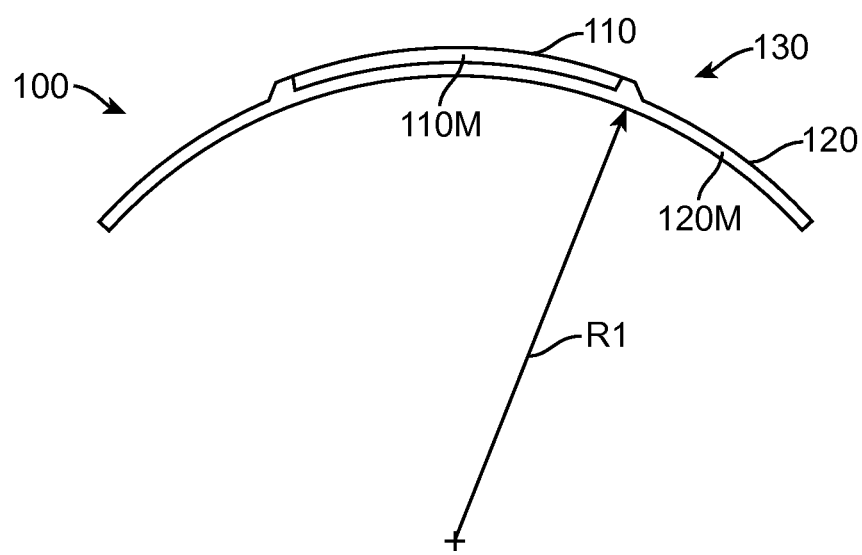
FIG. 1C1

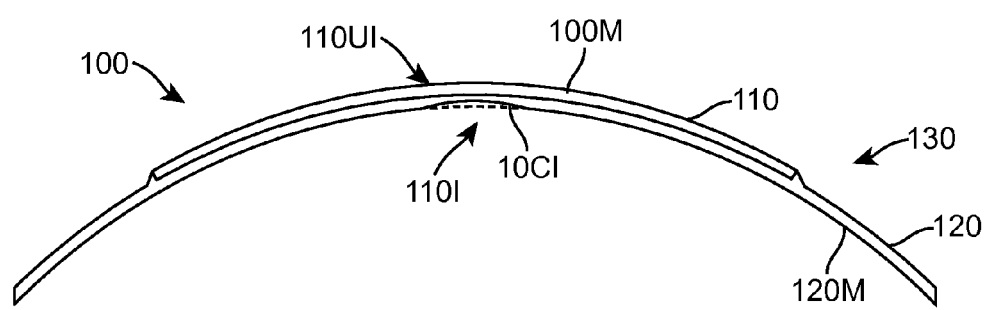
FIG. 1C1A

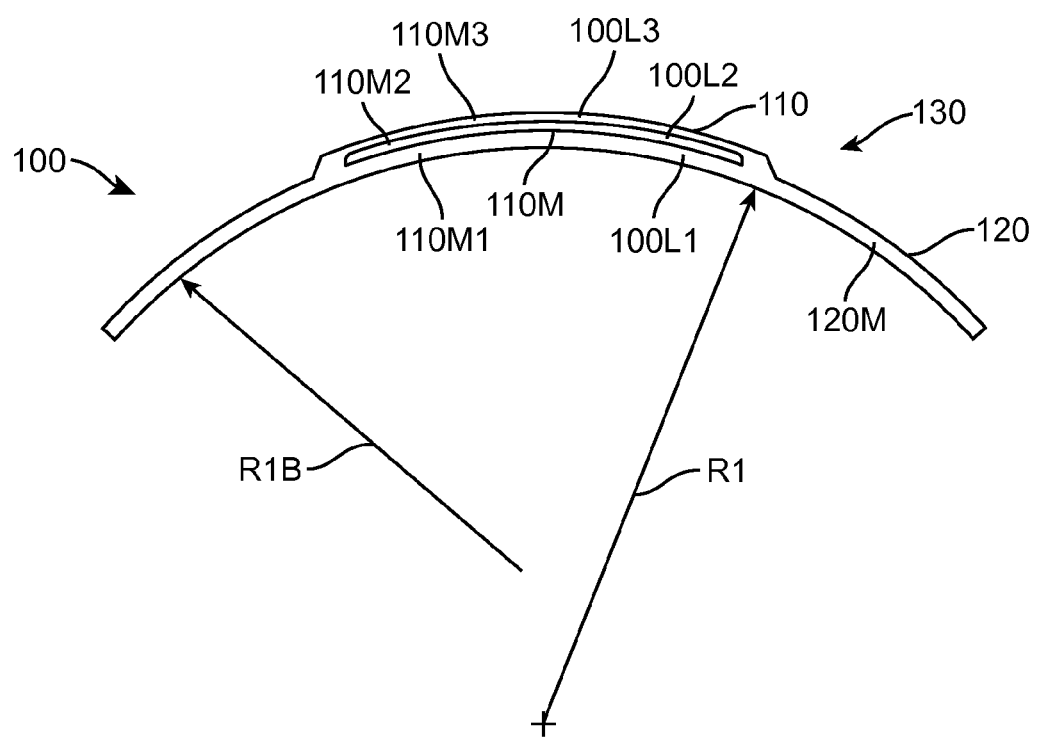
FIG. 1C2

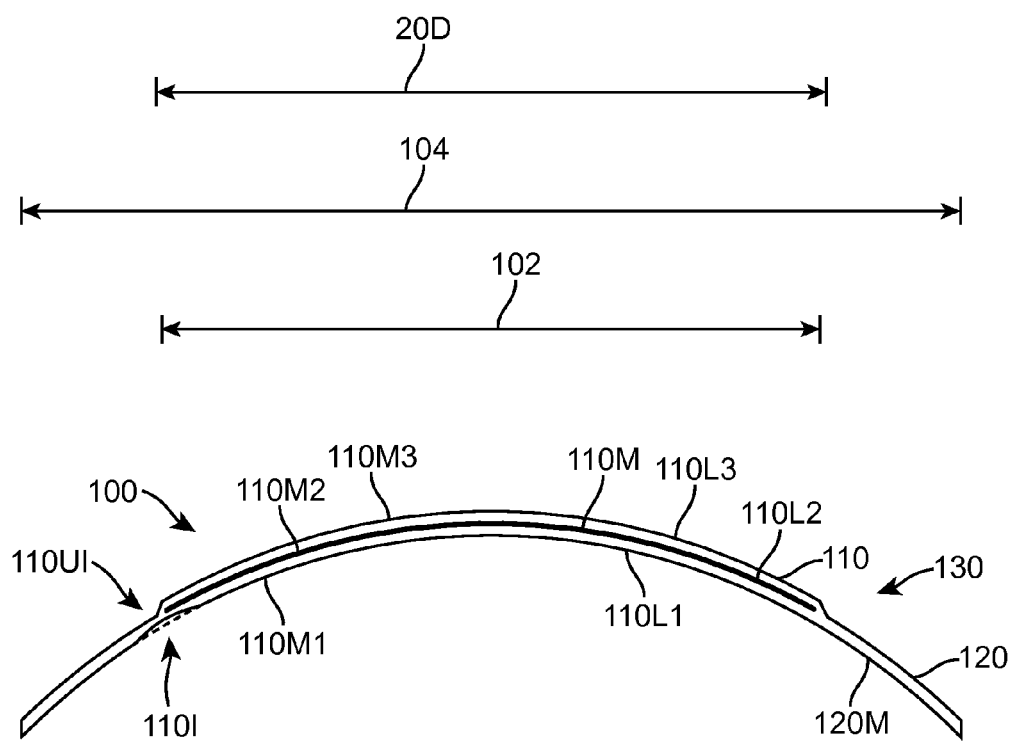
FIG. 1C2A

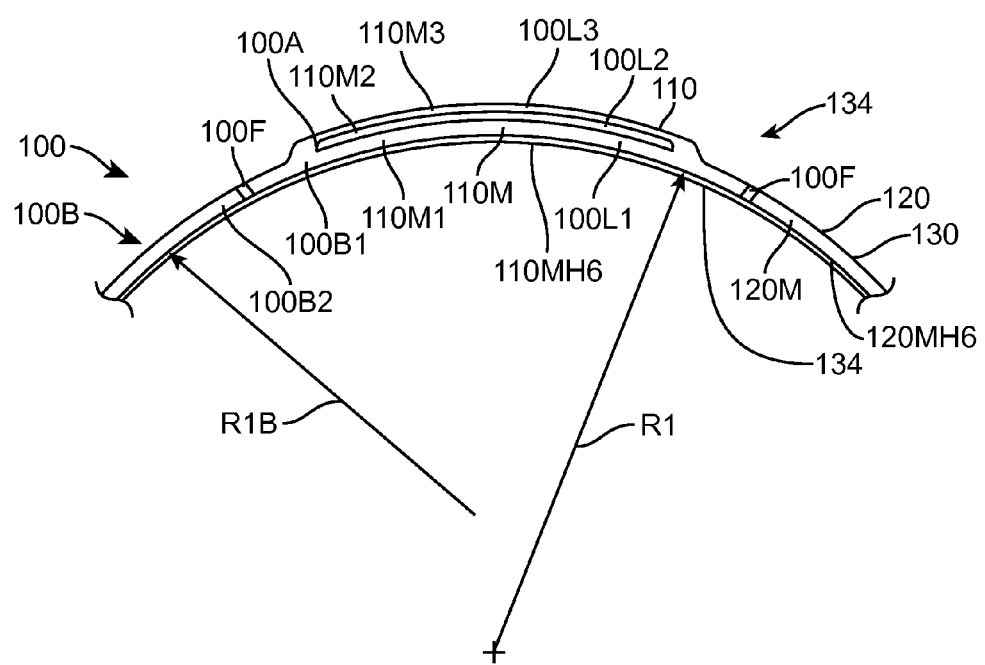
FIG. 1C2A1

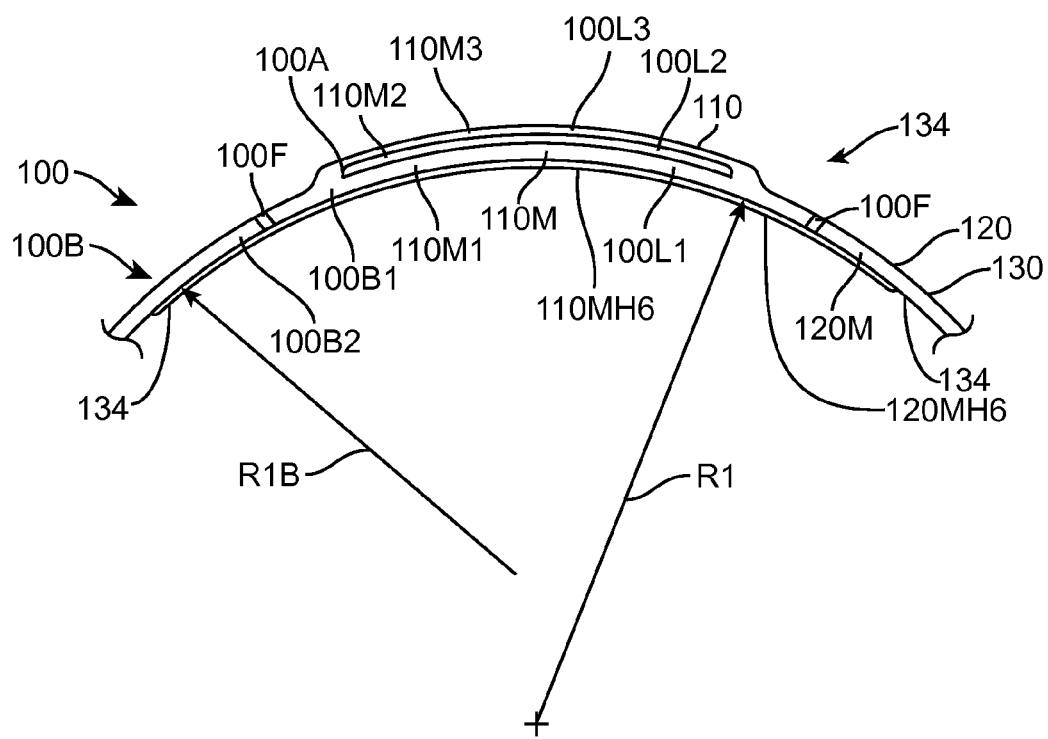
FIG. 1C2B

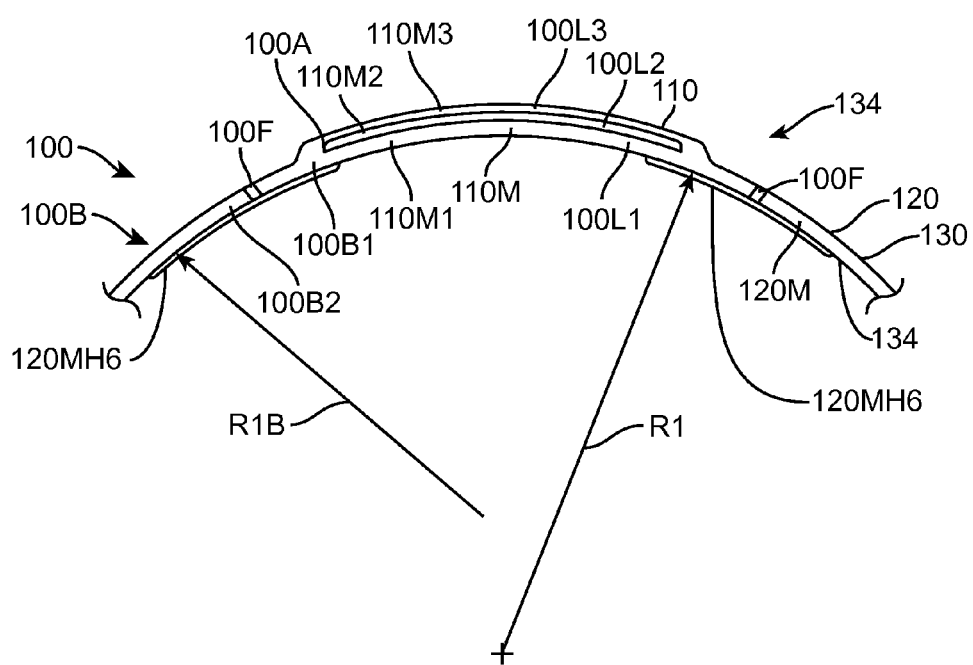
FIG. 1C2C

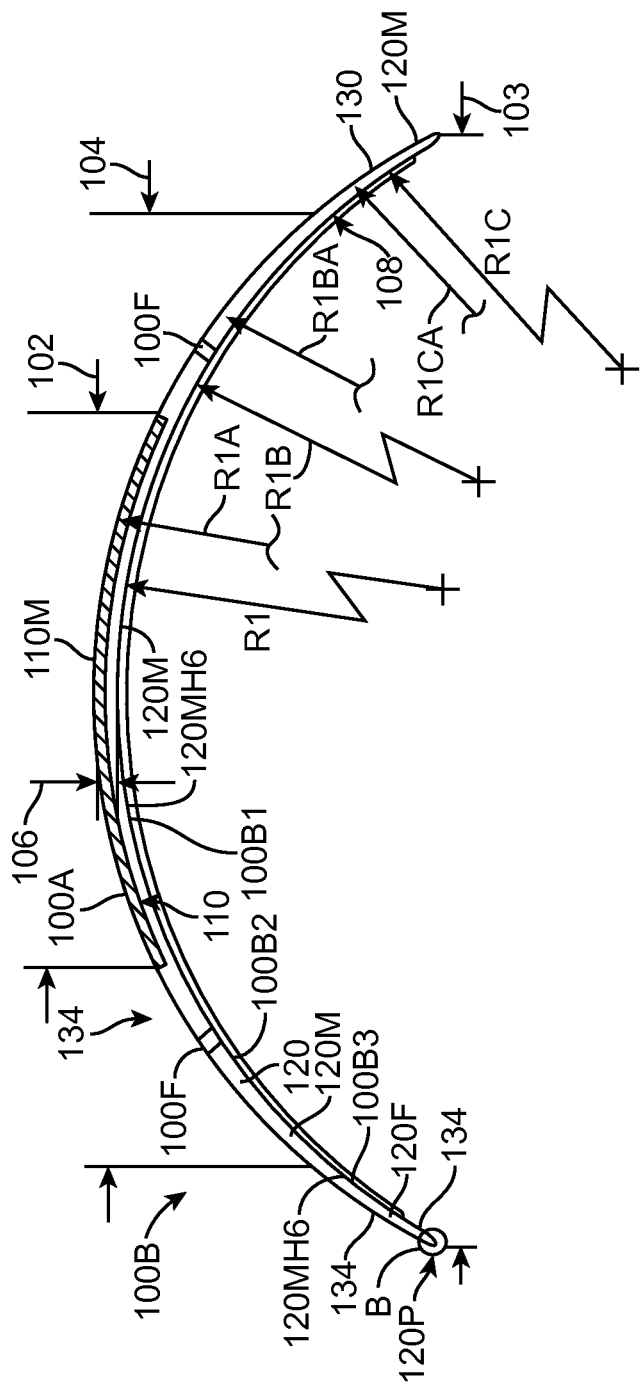
FIG. 1C3

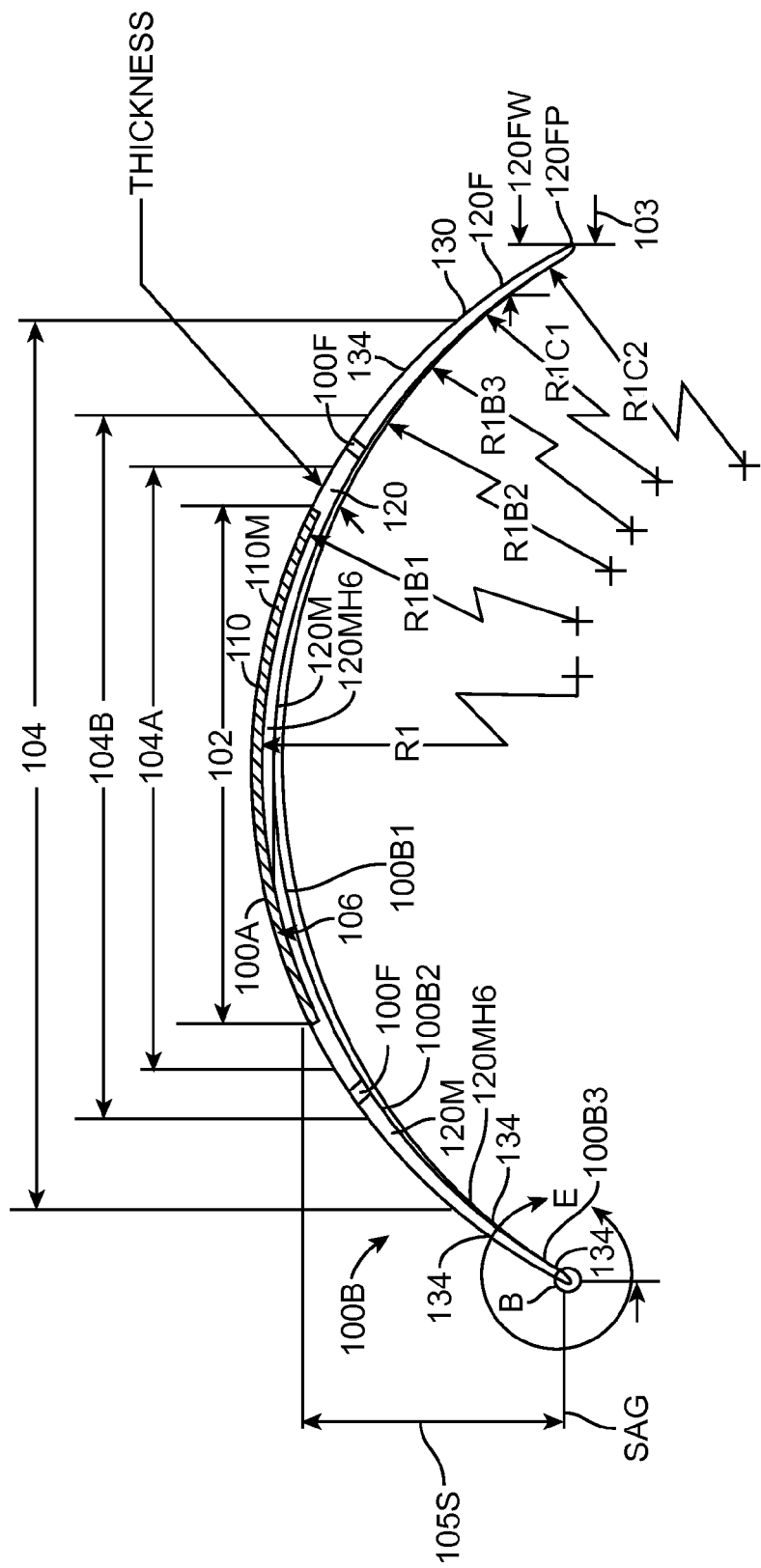
FIG. 1C4

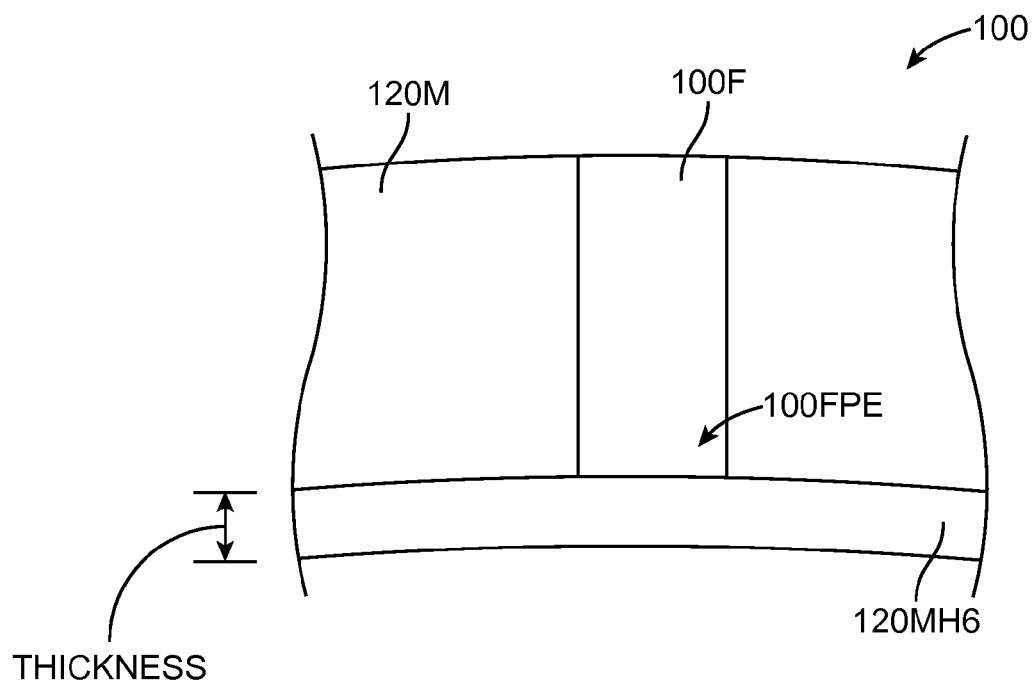
FIG. 1C5
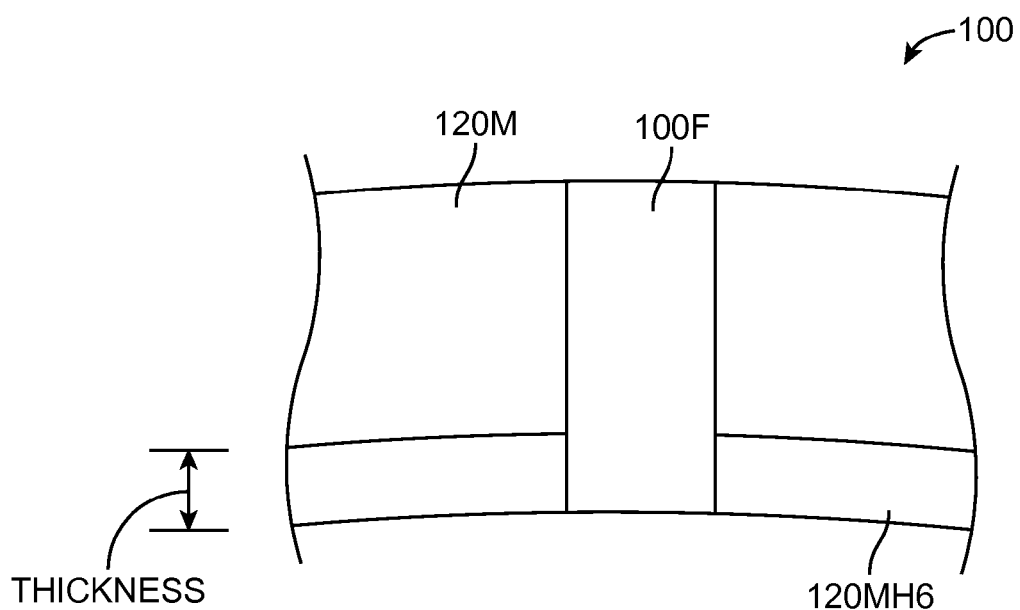
FIG. 1C6

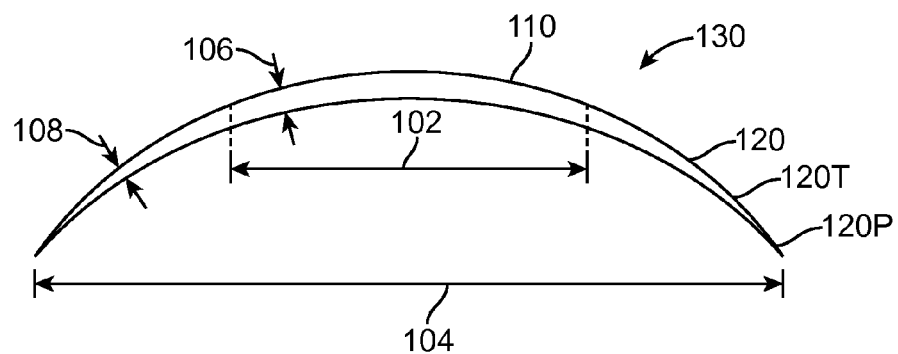
FIG. 1G
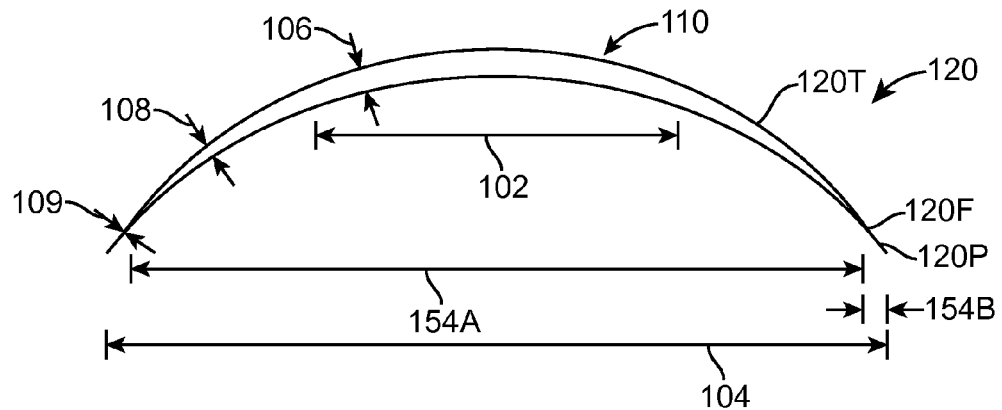
FIG. 1G1

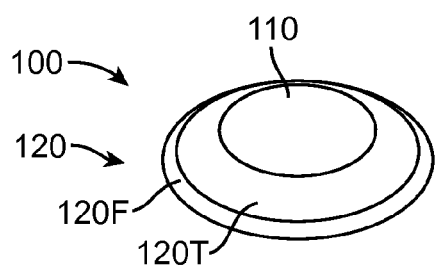
FIG. 1G1A
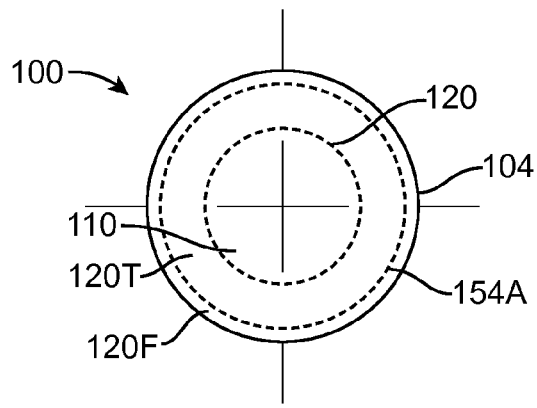
FIG. 1G1B
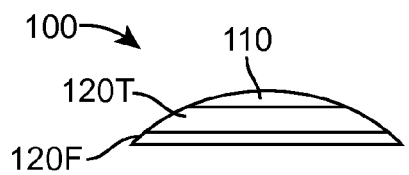
FIG. 1G1C
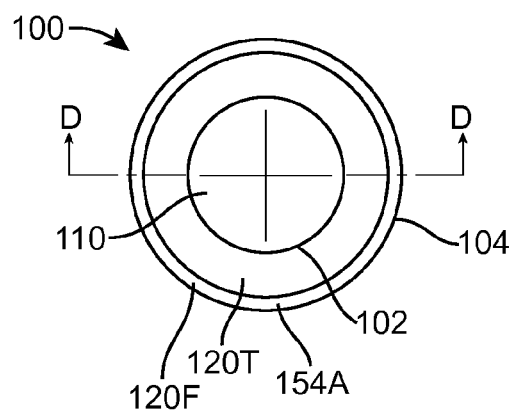
FIG. 1G1D

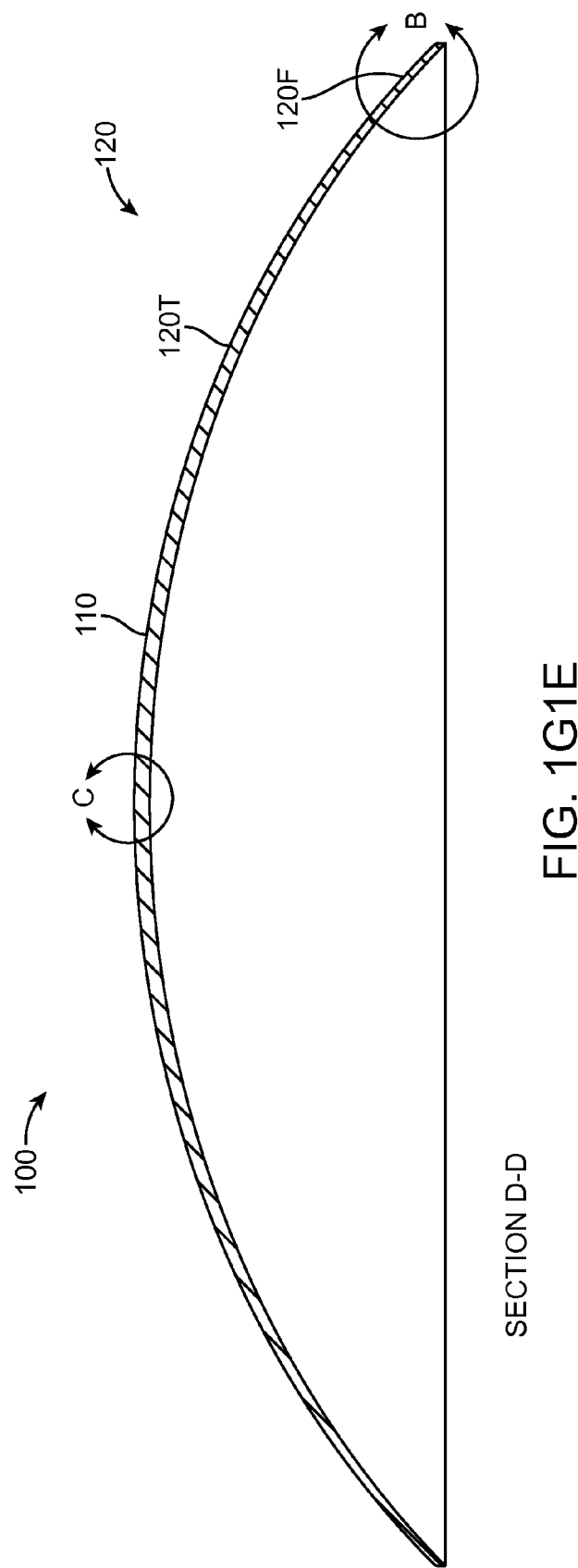
FIG. 1G1E SECTION D-D

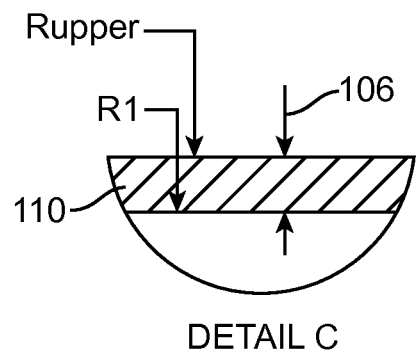
DETAIL C
FIG. 1G1F
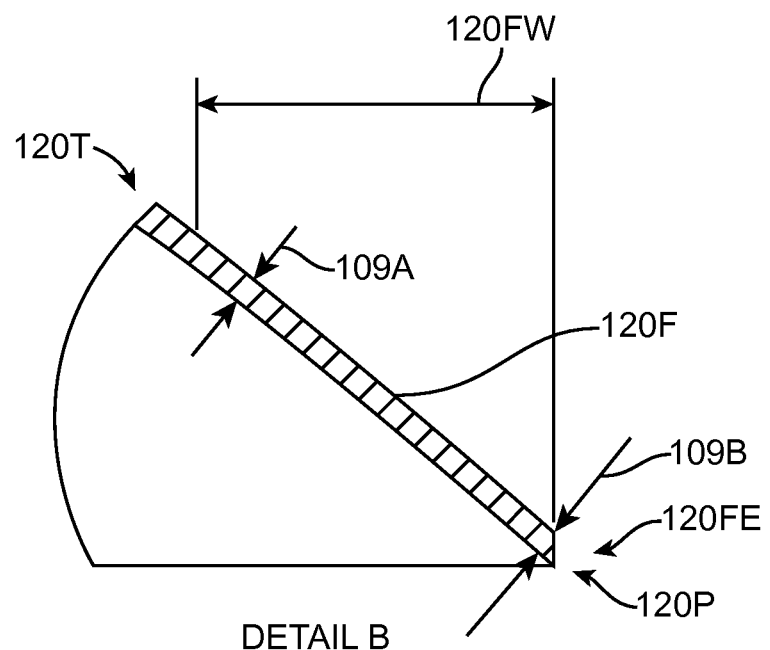
DETAIL B
FIG. 1G1G

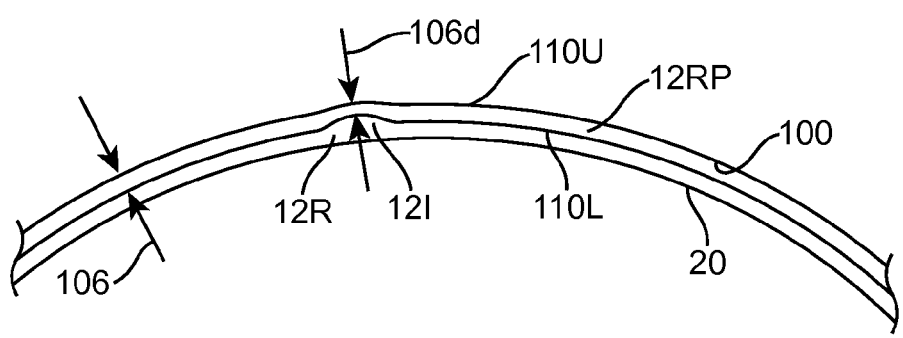
FIG. 1H1

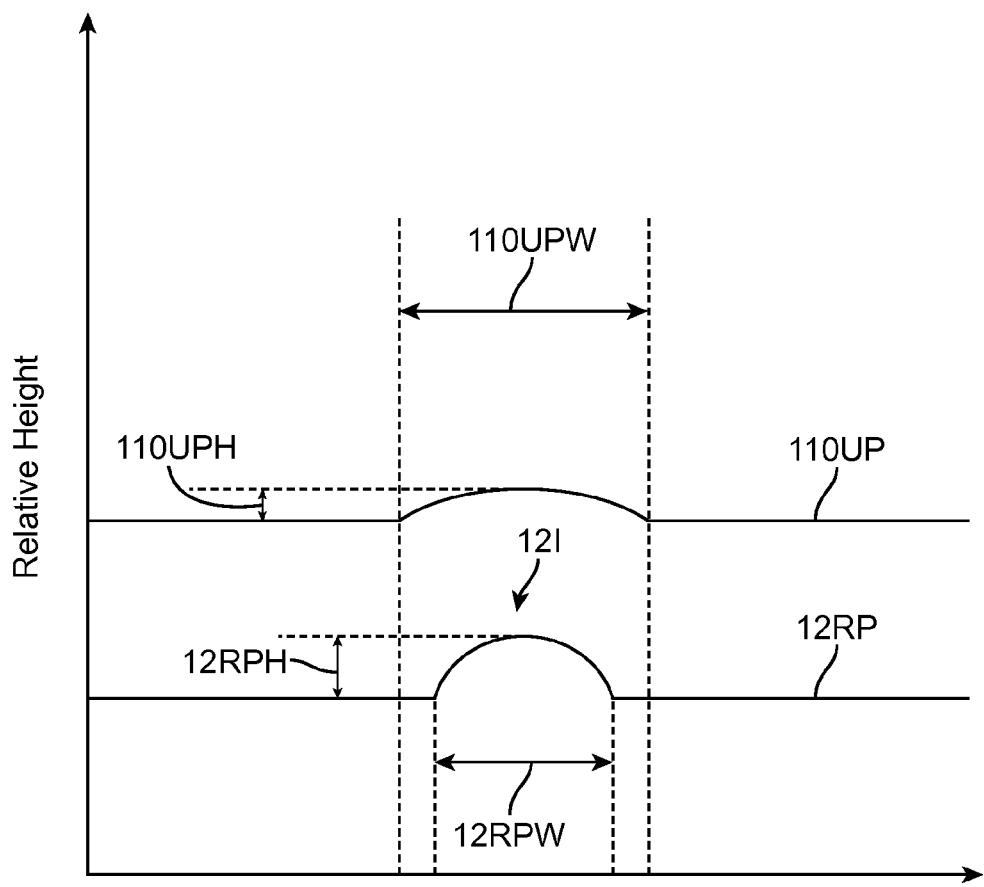
FIG. 1H2

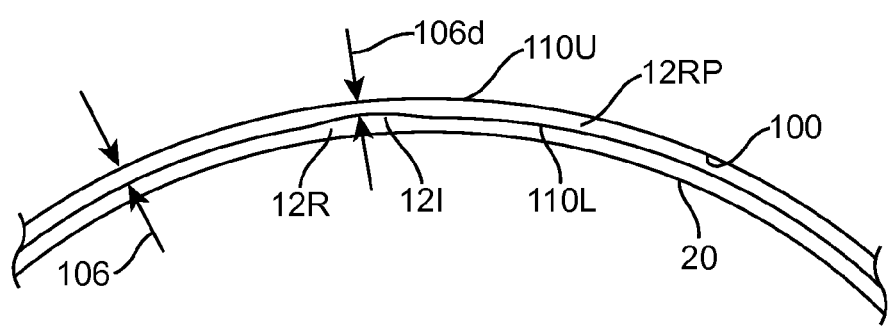
FIG. 1I1

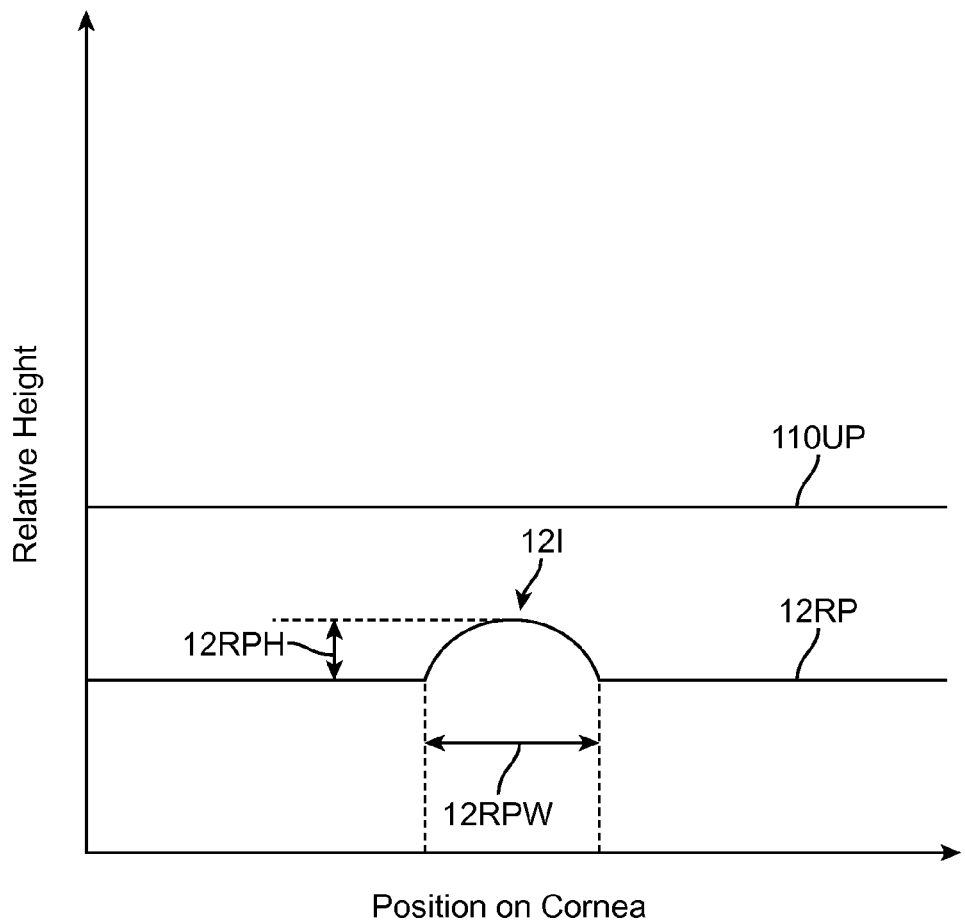
FIG. 1I2
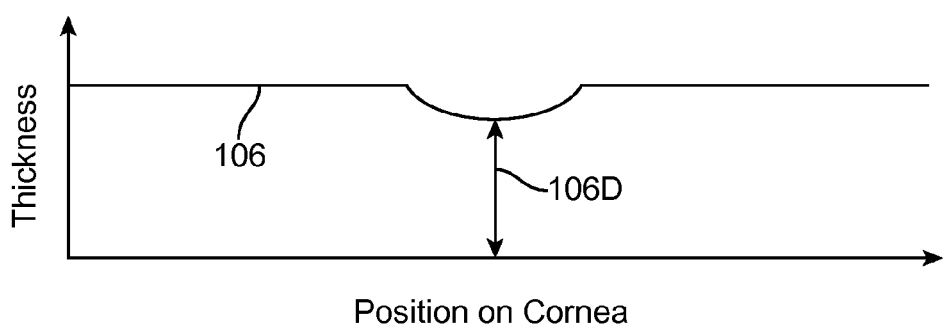
FIG. 1I3

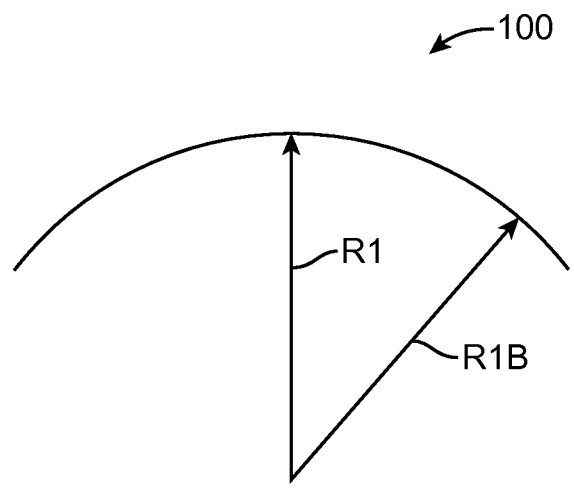
FIG. 1J1
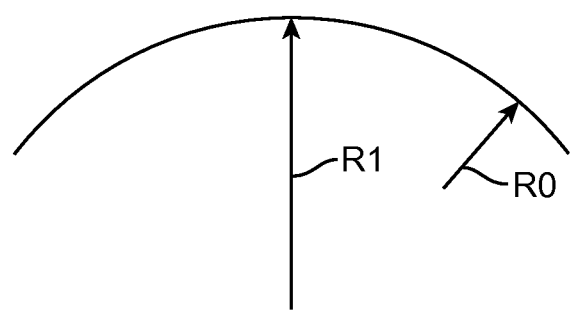
FIG. 1J2

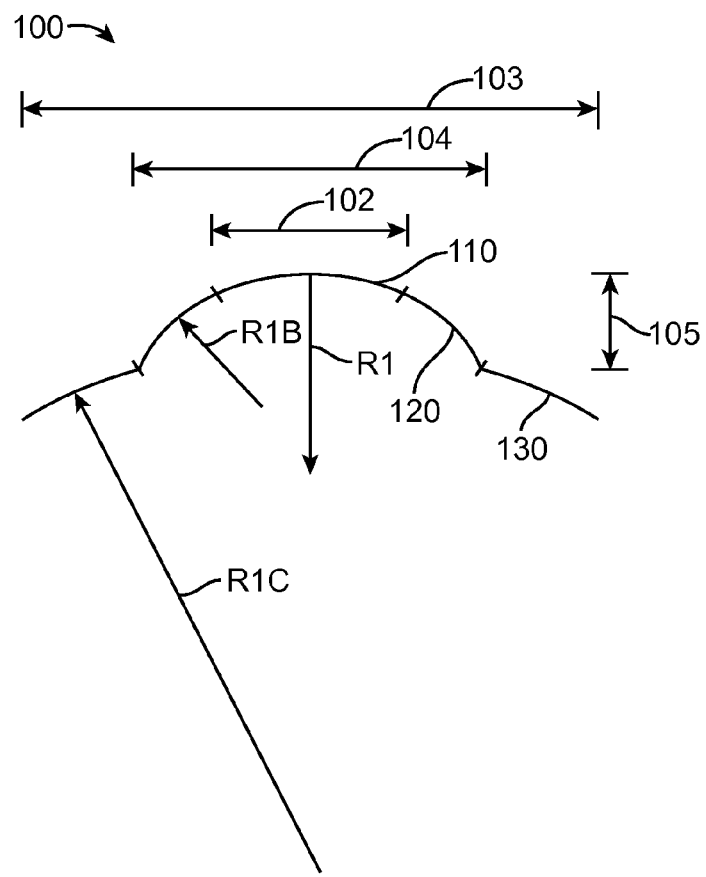
FIG. 1J3
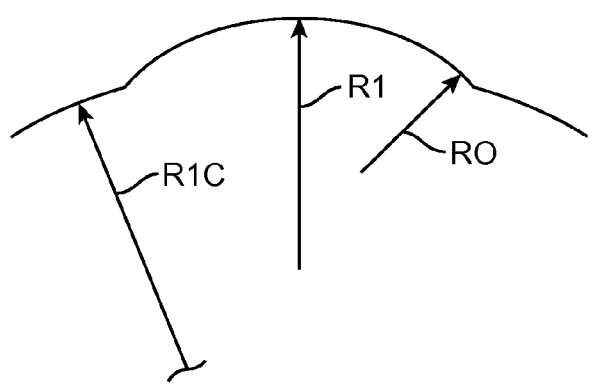
FIG. 1J4

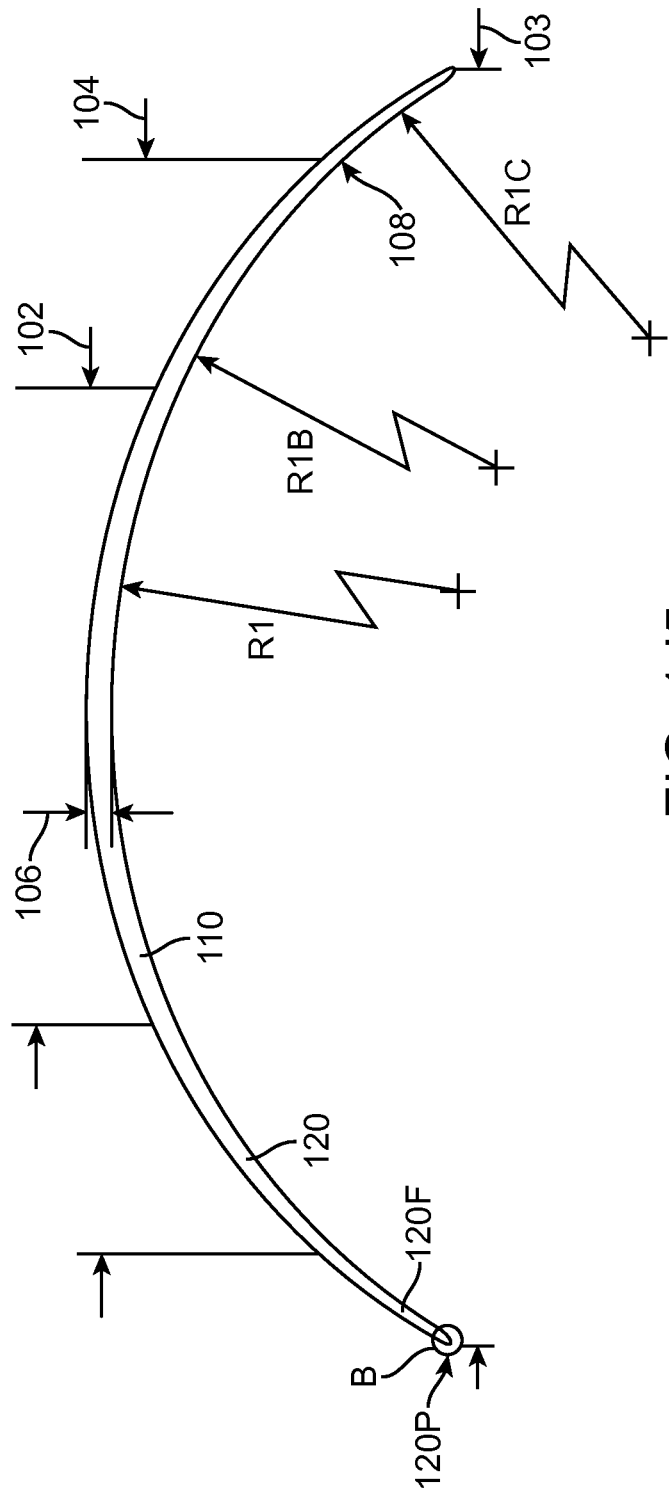
FIG. 1J5

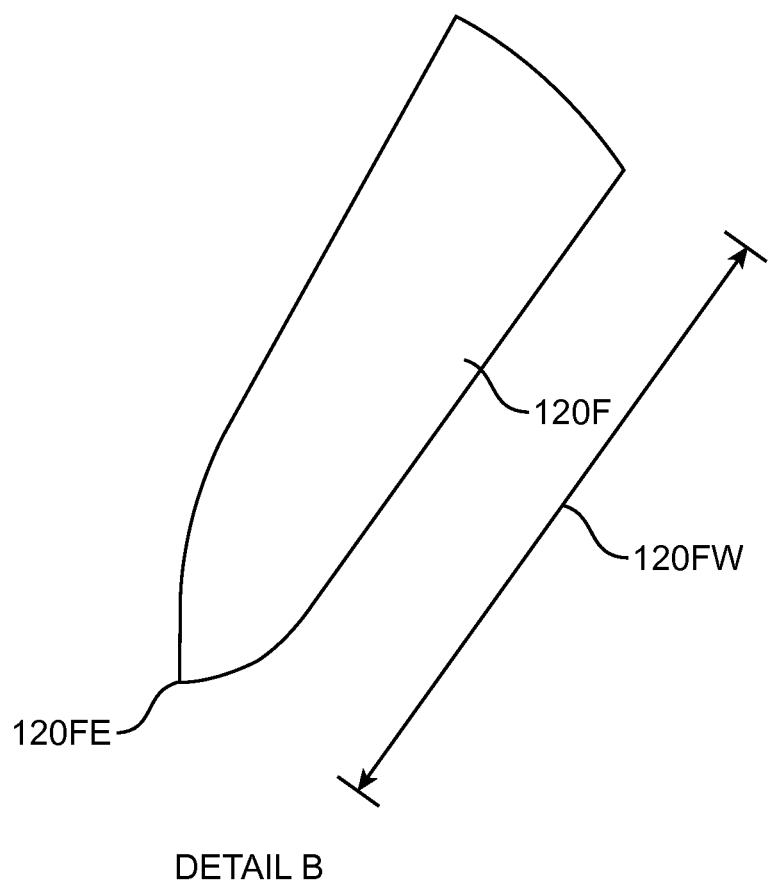
DETAIL B
FIG. 1J6

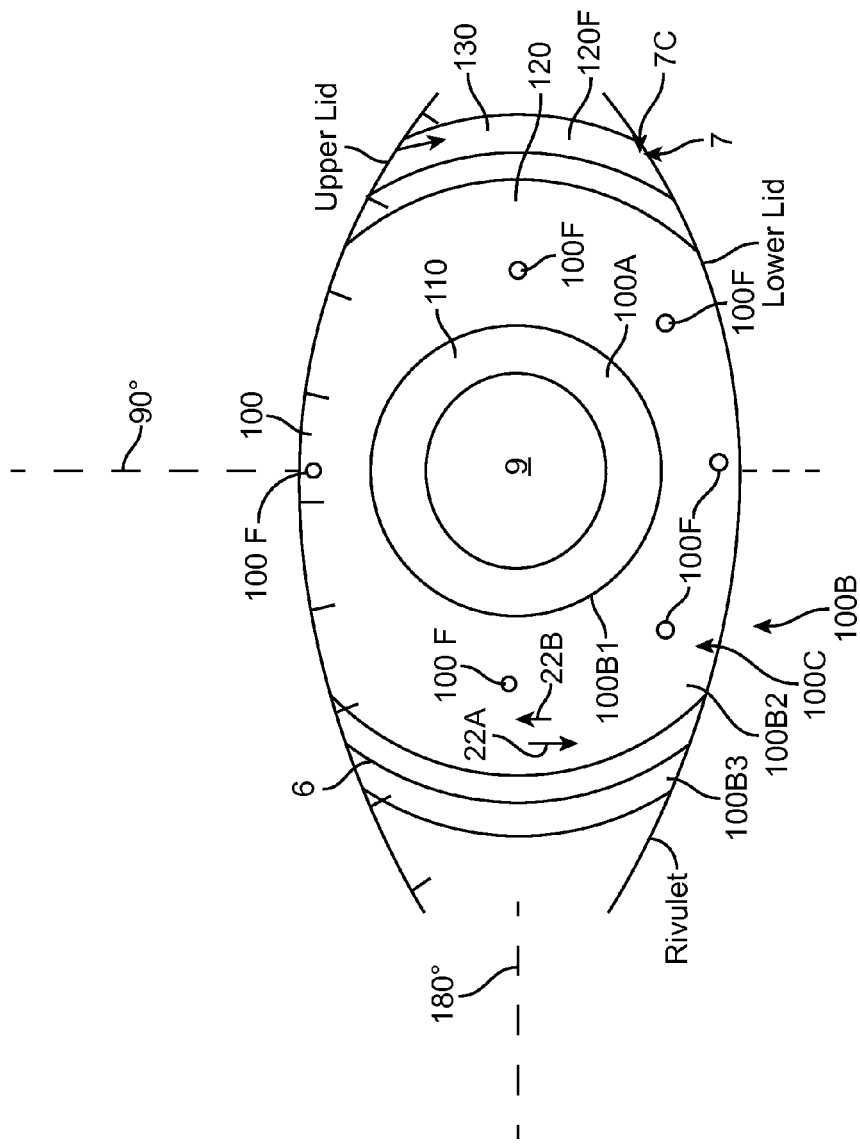
FIG. 2A1

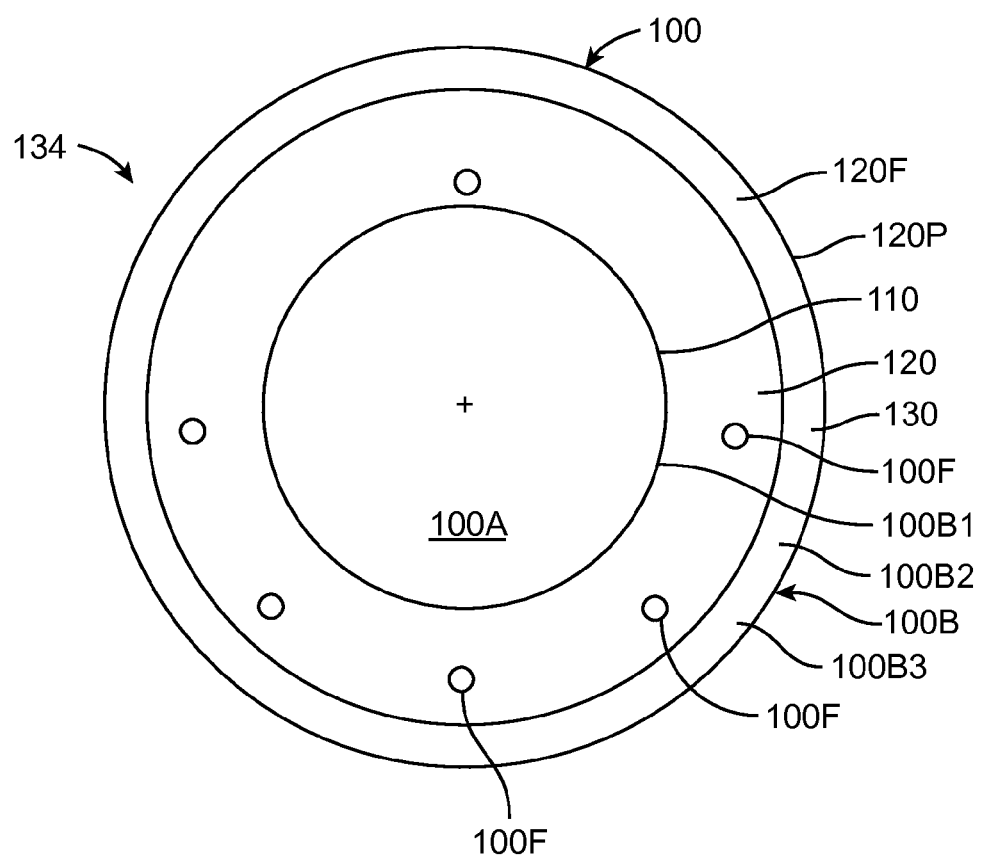
FIG. 2A2

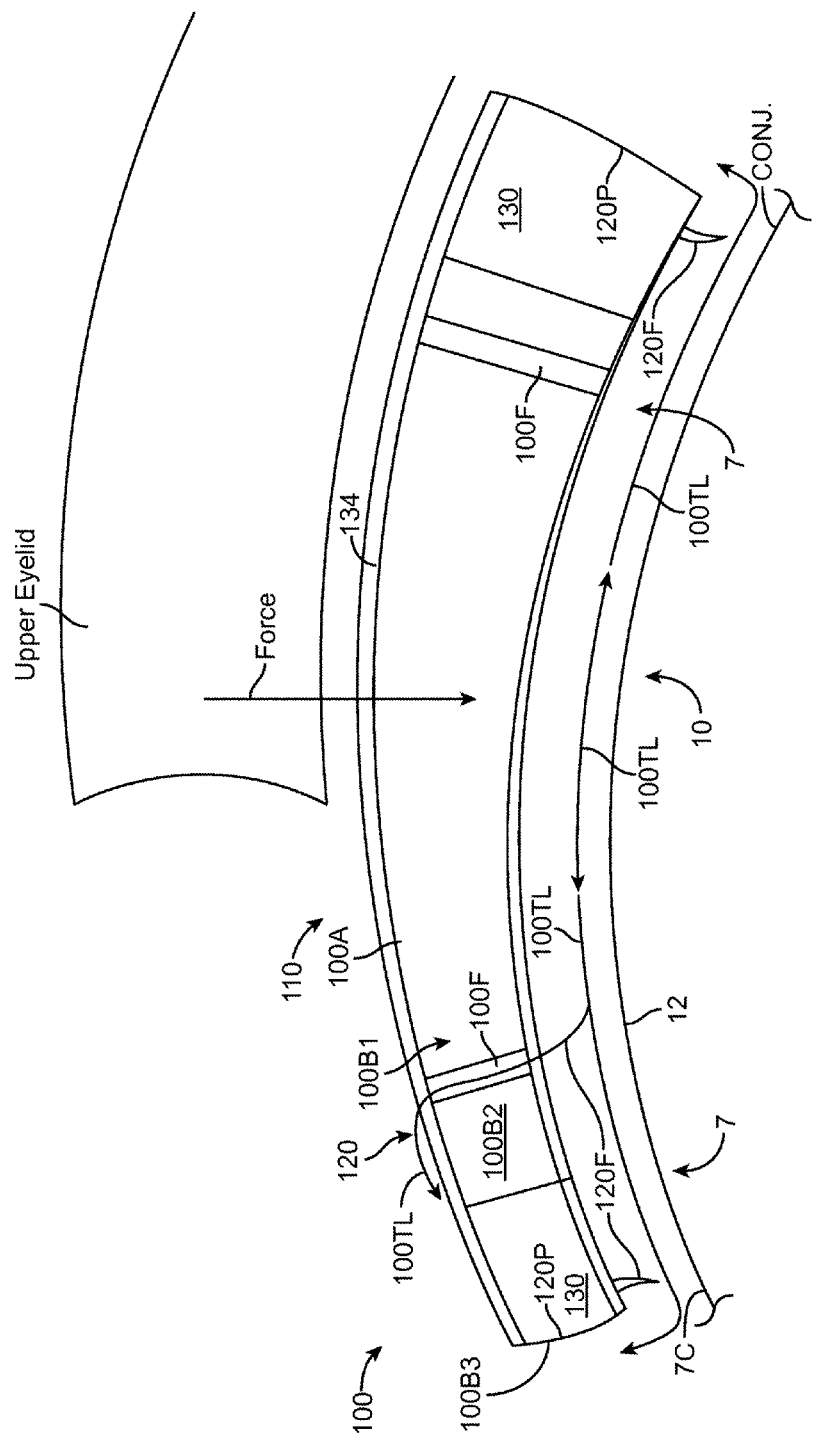
FIG. 2A3

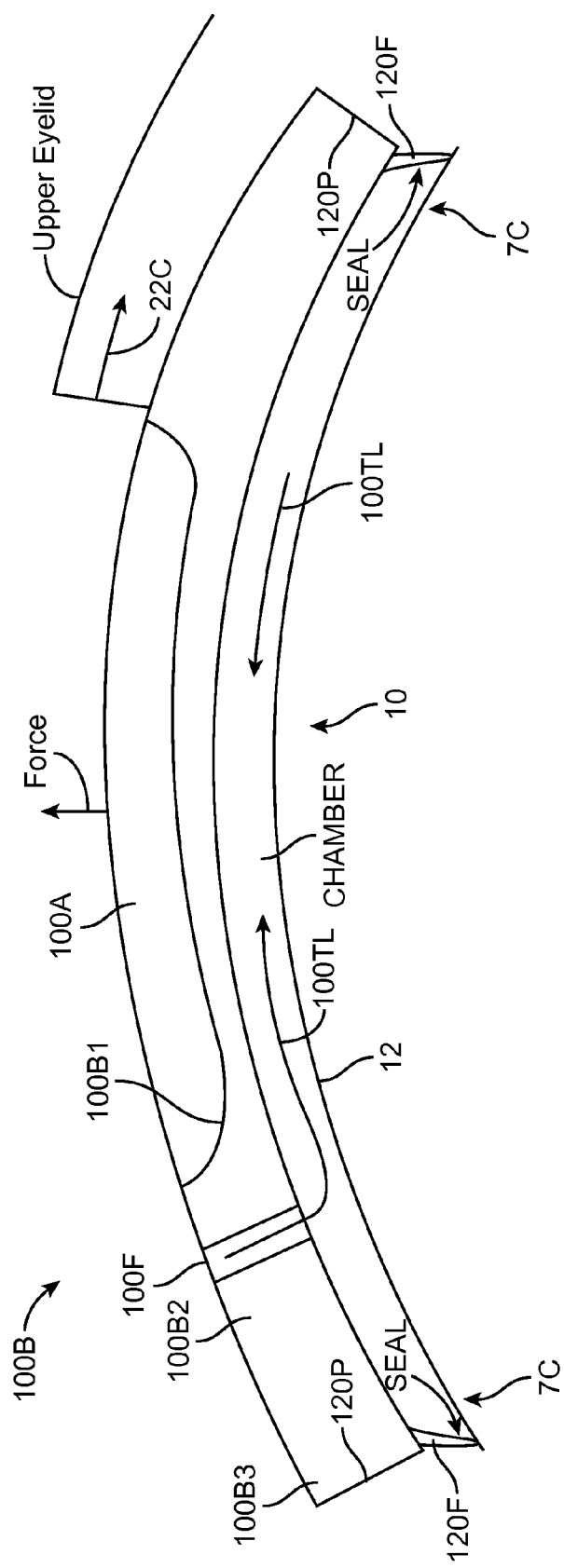
FIG. 2A4

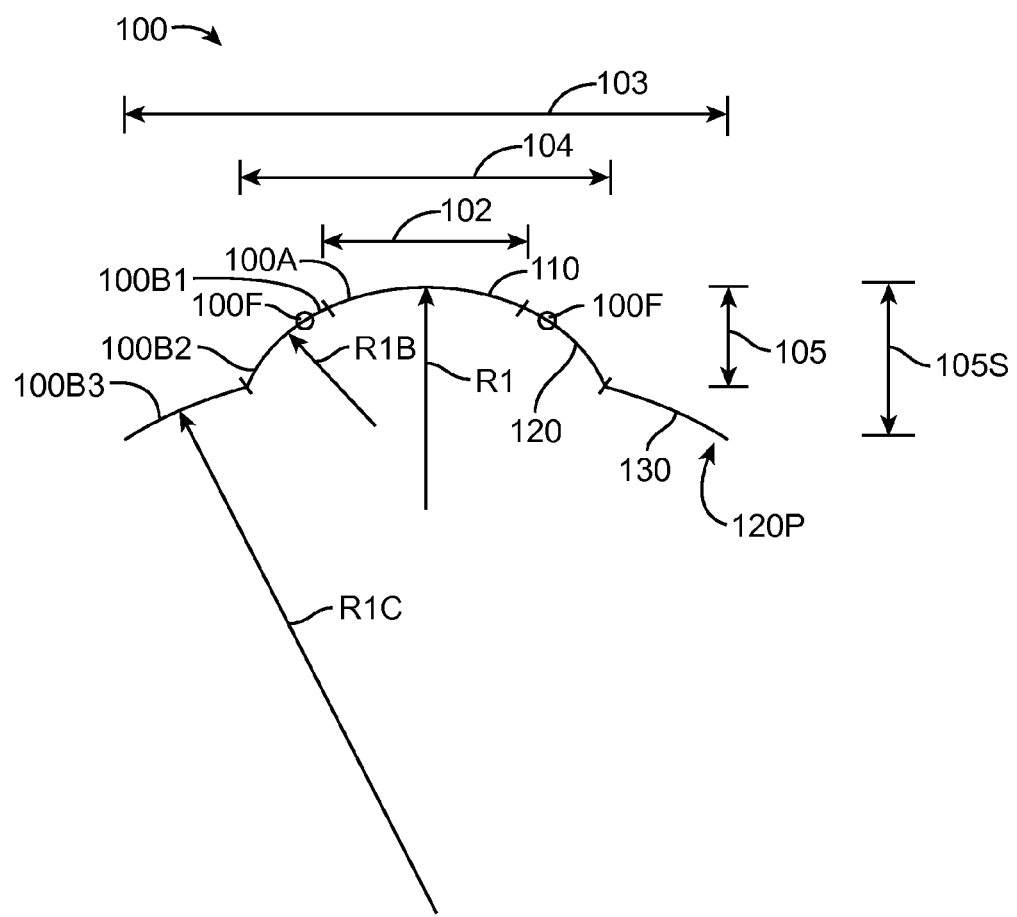
FIG. 2B1

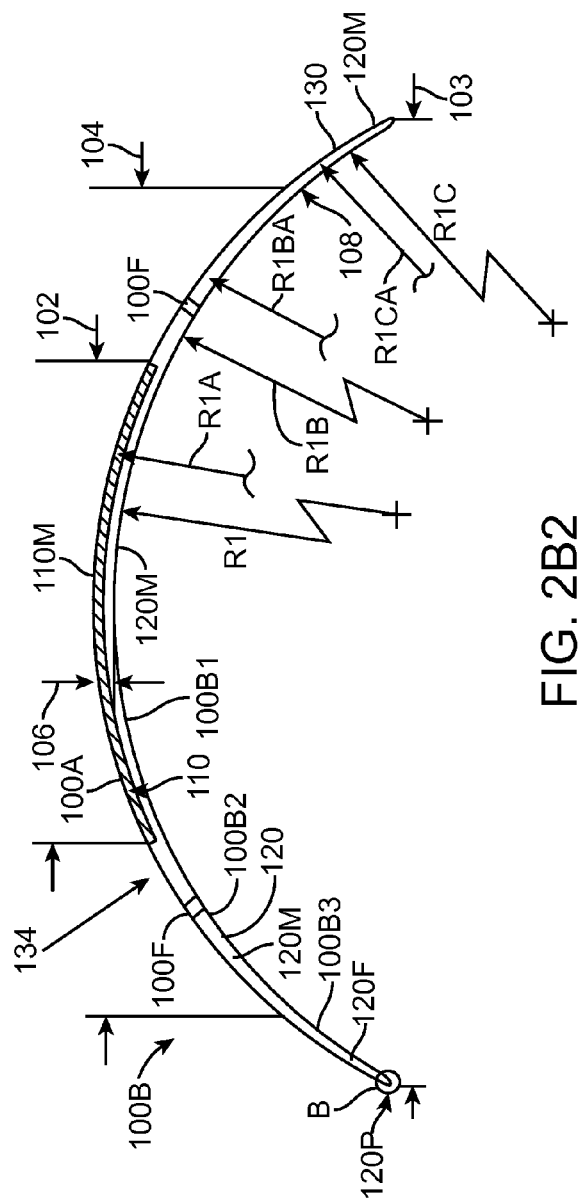
FIG. 2B2
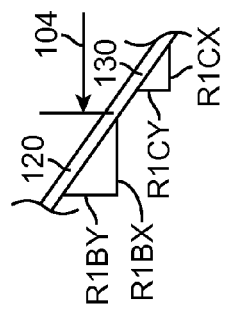
FIG. 2B2-1

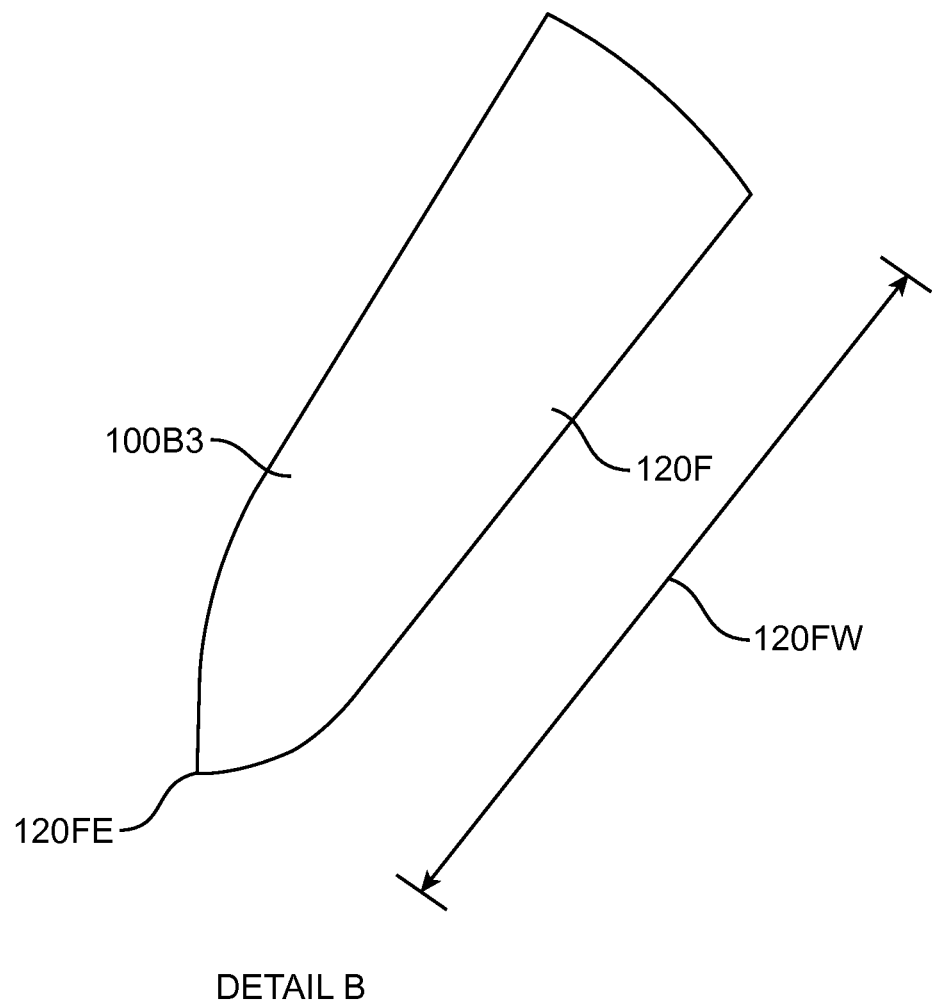
DETAIL B
FIG. 2B3

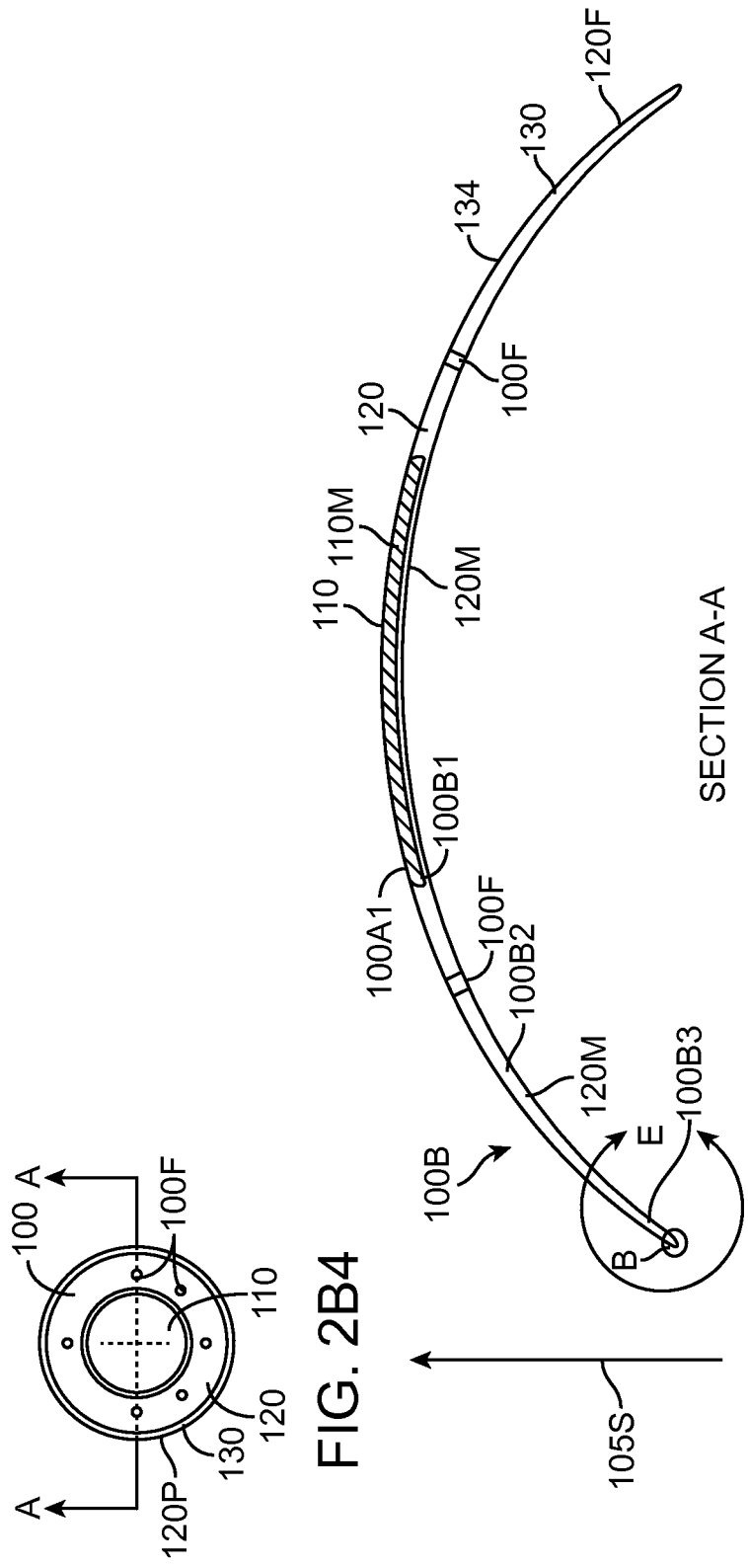

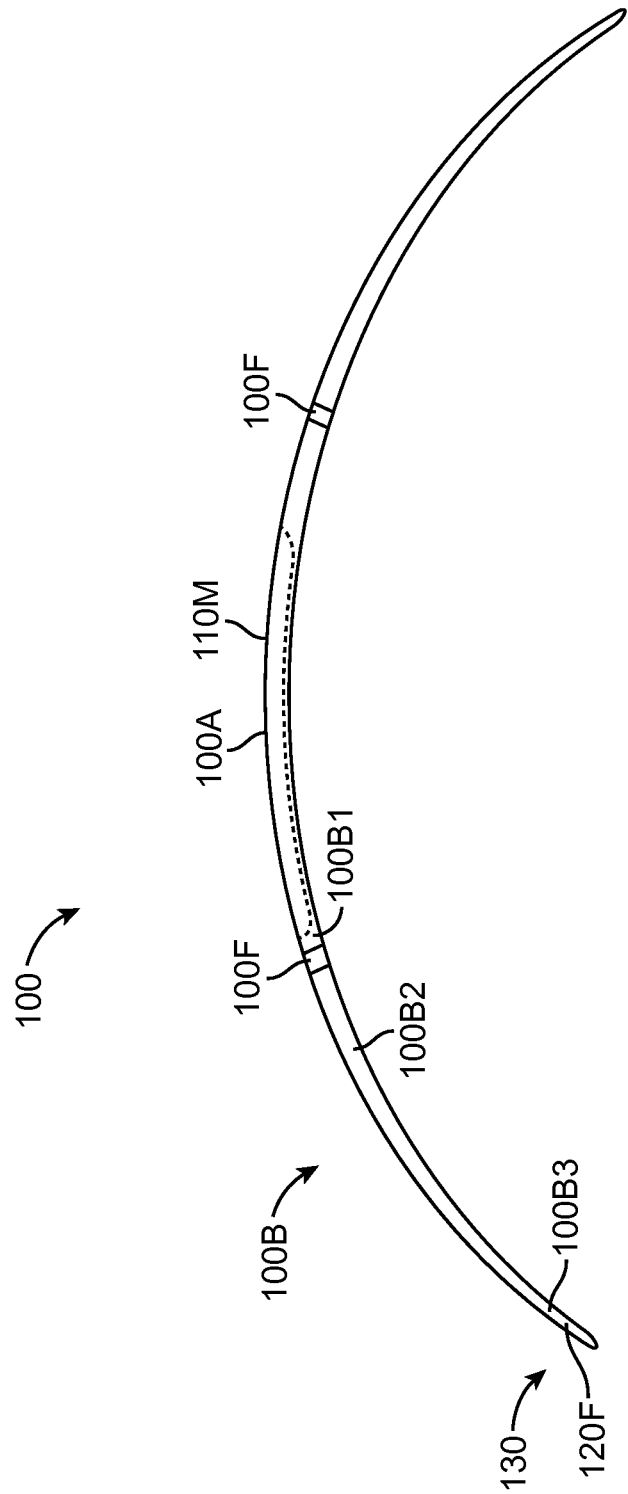
FIG. 2B6

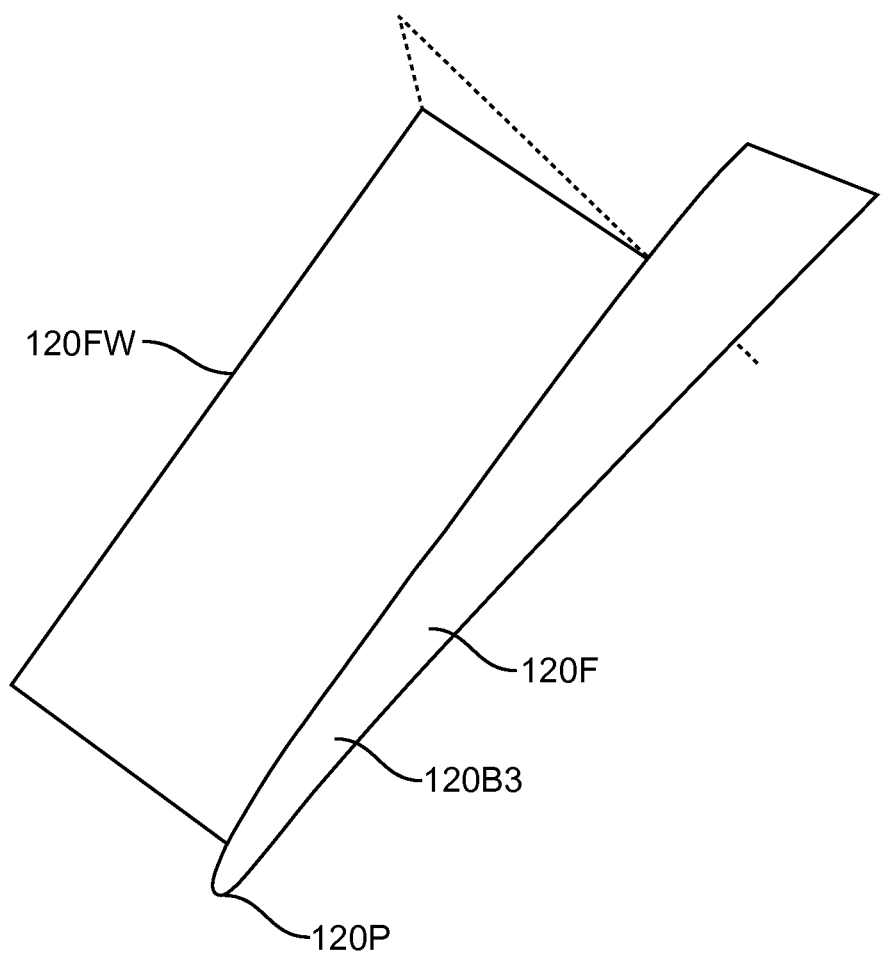
FIG. 2B7

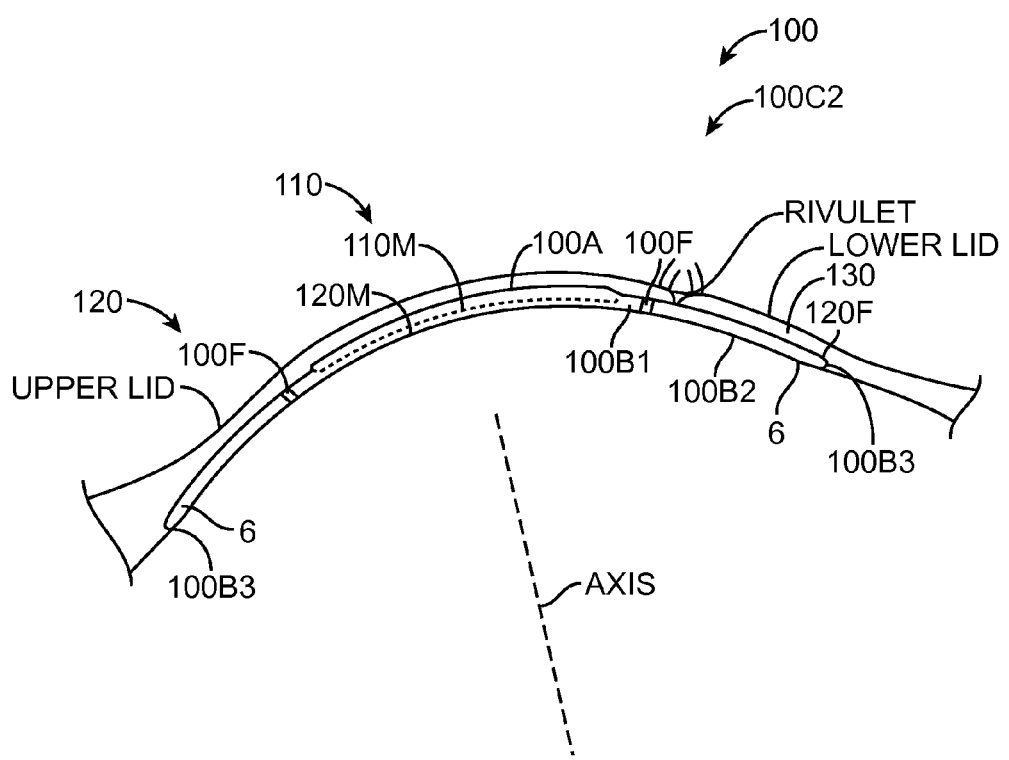
FIG. 3F1

US 9,395,558 B2

METHODS AND APPARATUS TO IDENTIFY EYE COVERINGS FOR VISION

CROSS-REFERENCES TO RELATED APPLICATIONS

The present PCT application claims priority to U.S. App. Ser. Nos. 61/406,504, filed on Oct. 25, 2010, entitled "METHODS AND APPARATUS TO IDENTIFY THERAPEUTIC SHIELDS FOR VISION AND PAIN"; and U.S. App. Ser. No. 61/480,231, filed on Apr. 28, 2011, entitled "METHODS AND APPARATUS TO IDENTIFY EYE COVERINGS FOR VISION"; each assigned to NexisVision, Inc., the full disclosures of which are incorporated herein by reference.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

The present invention is generally directed to vision and treatment of the eye to provide improved vision. Although specific reference is made to coverings for vision correction such as the correction of refractive error and also to treatment of eyes having epithelial defects following photorefractive keratectomy, embodiments of the present invention may comprise extended wear contact lenses that can be used to correct vision in many ways such as with one or more of aberration correction, multifocal correction, presbyopia correction, and astigmatism correction.

The eye includes several tissues that allow patients to see. The cornea of the eye is an anterior tissue of the eye that is clear in healthy eyes and refracts light so as to form an image on the retina. The retina is a posterior tissue of the eye that senses light from the image formed thereon and transmits signals from the image to the brain. The cornea includes an outer layer of tissue, the epithelium, which protects the underlying tissues of the cornea, such as Bowman's membrane, the stroma and nerve fibers that extend into the stroma and Bowman's membrane. The healthy eye includes a tear film disposed over the epithelium. The tear film can smooth small irregularities of the epithelium so as to provide an optically smooth surface. The tear film is shaped substantially by the shape of the underlying epithelium, stroma, and Bowman's membrane, if present. The tear film comprises a liquid that is mostly water and does include additional components, such as mucoids and lipids. The many nerve fibers of the cornea provide sensation to promote blinking that can cover the cornea with the tear film. The nerve fibers also sense pain so that one will normally avoid trauma to the cornea and also avoid direct contact of an object to the cornea so as to protect this important tissue.

Work in relation to embodiments of the present invention suggests that at least some of the prior contact lenses and therapeutic coverings can be less than ideal in at least some instances. Many contact lenses and therapeutic coverings can be left in the eye for less than ideal amounts of time, as the patient removing and replacing the contact lens or therapeutic covering can be somewhat cumbersome and in at least some instances patients may leave the contact lens or therapeutic covering in the eye for amounts of time that can be longer than would be ideal. Although extended wear lenses can be left in the eye for somewhat longer amounts of time, the amount of time such lenses can be left in the eye can be less than ideal. Work in relation to embodiments of the present invention also suggests that tear flow of the prior contact lenses can be less than ideal, and that less than ideal tear flow may be related to the potential complications and can limit the amount of time such lenses can be left in the eye.

In the healthy cornea, the proper amount of hydration of the cornea, sometimes referred to as dehydration of the cornea, is maintained such that the cornea remains clear. The cornea includes a posterior endothelial layer that pumps water from the cornea into the adjacent anterior chamber. The epithelium inhibits flow of water from the tear liquid into the cornea, such that the corneal stroma can be maintained with the proper amount of hydration with endothelial pumping. The endothelial pumping of water from the cornea to maintain the proper hydration and thickness of the eye is often referred to as deturgescence. When the corneal epithelium heals, the layer of cells forming over the defect can be at least somewhat irregular in at least some instances, such that the vision of the patient can be less than ideal.

As the post-ablation cornea may have a complex shape, many of the prior commercially available lenses may not fit the ablated cornea as well as would be ideal, and in at least some instances fitting of lenses can be time consuming and awkward. Rigid gas permeable (hereinafter "RGP") lenses can be uncomfortable for the patient and difficult to fit. Commercially available contact lenses having a rigid central portion and a soft peripheral skirt can be difficult and/or time consuming to fit to the ablated cornea and may not fit very well in at least some instances. The ablated cornea may comprise an abrupt change in curvature near the edge of the ablation, and in at least some instances it can be difficult to fit such lenses near the edge of the ablation. Also, at least some of the commercially available contact lenses may not be suitable for extended wear and may be removed each day, which can be somewhat awkward for a patient and can result in lack of compliance and lenses remaining in the eye longer than would be ideal in at least some instances.

In light of the above, it would be desirable to provide improved contact lenses for vision correction and coverings for treatments related to epithelial defects of the cornea, such as epithelial defects following photorefractive keratectomy (hereinafter "PRK"). Ideally, these contact lenses and coverings would provide treatments that improve tear flow and avoid at least some of the deficiencies of known techniques while providing improved patient comfort and/or vision.

BRIEF SUMMARY OF THE INVENTION

Embodiments of the present invention provide improved methods and apparatus to fit and identify coverings to treat eyes. The treated eye may comprise a natural eye, or an eye having an epithelial defect of the eye, such as an eye ablated with PRK refractive surgery. In many embodiments, the covering can be identified and fit to the eye so as to provide one or more of improved hydration or flow of tear liquid under the covering. The covering can be fit and identified based on an inner corneal curvature and an outer corneal curvature and one or more of a limbus sag height or a conjunctival sag height.

The covering to fit the eye may comprise a contact lens and can provide improved hydration and tear flow such that the covering can be left on the eye to correct vision for extended amounts of time. The covering may comprise one or more structures to provide hydration under the covering such that the covering can remain in the eye and correct vision for an extended amount of time. In many embodiments, the covering comprises a layer of hydrogel extending along a lower surface of the covering to provide hydration to a surface of the eye. Alternatively or in combination, the covering may comprise a material having fenestrations and an outer portion shaped to contact the conjunctiva to pump tear liquid when the eye blinks. The covering may comprise a deflectable outer portion having a resistance to deflection such that a chamber is formed when the covering is placed on the eye and the eye is open with the eyelids separated. The resistance to deflection of the deflectable outer portion is configured such that the outer portion deflects inward toward the cornea when the eyelid closes to pump tear liquid. The fenestrations can draw tear liquid into the chamber located under the covering when the eye opens and the chamber can expand. The outer portion of the covering comprises a sclera coupling portion shaped to contact the conjunctiva to define the chamber when the covering is placed on the eye. The fenestrations and sclera coupling portion of the covering can pass tear liquid away from the chamber when the eye closes and pressure of one or more eyelids urges the covering toward the cornea such that the chamber volume decreases. In many embodiments, opening of the eye so as to separate the eyelids reduces pressure on the outer portion of the covering such that the outer portion of the covering over an outer portion of the cornea can separate from the outer portion of the cornea so as to draw liquid through the fenestrations and into the chamber located under the covering. The sclera coupling portion of covering may contact the conjunctiva to inhibit the flow of tear liquid under the sclera coupling portion when the eye opens and tear liquid is drawn through the fenestrations, for example with formation of a seal where the covering contacts the conjunctiva. When the eye blinks subsequently, the pressure of the one or more eyelids can urge the covering toward the cornea such that tear liquid can pass through the fenestrations, and the sclera coupling portion may separate slightly from the conjunctiva to pass tear liquid under the sclera coupling portion, so as to rinse the cornea, the limbus, the conjunctiva and the underside of the covering with the pumped tear liquid. The covering may comprise a material having high oxygen permeability such as silicone such that the covering may provide improved tear flow and high oxygen permeability. This improved flow of tear liquid can allow the covering such as a contact lens to be worn for extended amounts of time of at least about one week, for example thirty days or sixty days or more. The improved tear flow can improve healing and vision of eyes with epithelial defects, for example epithelial defects following PRK.

In many embodiments, the identified covering comprises an inner optical component for vision, such as a lens, and an outer coupling component to hold the inner component in relation to the pupil to improve vision. The coupling component may comprise a deflectable material that inhibits passage of the tear liquid through the material such that the tear liquid passes through the fenestrations when the eye blinks and an eyelid exerts pressure on the optical component. The outer coupling component may comprise the fenestrations to pass the tear liquid and the outer sclera coupling portion to contact the conjunctiva. The optical component may comprise a first material and first thickness corresponding to a first rigidity. The coupling component may comprise a second material and a second thickness corresponding to a second rigidity. The second material can be softer than the first material and the second thickness can be less than the first thickness such that the coupling component can be deflected with the eyelid, and such that the coupling component can be deflected by an amount greater than the optical component when the eyelids close to cover the first component and the second component. The optical component can be more rigid than the coupling component, such that the optical component can provide vision when the outer portion is deflected with one or more eyelids.

The covering can be identified such that the alignment of the optical component to the pupil provided with the coupling to the conjunctiva and underlying sclera can be beneficial for vision. The optical component can be held at a substantially fixed location in relation to the pupil so as to provide improved vision such as presbyopia correction and vision correction of aberrations that may depend on location of the pupil such as measured wavefront aberrations, spherical aberration, coma and trefoil.

The covering can be identified such that the optical component and coupling component can be helpful to improve vision and regeneration of the epithelium in eyes with epithelial defects. The optical component can smooth the cornea and may smooth irregularities of the epithelium and ablated stroma. The coupling component can support the optical component so as to resist sliding movement of the optical component and provide an environment to promote regeneration of the epithelium. The pumping of the tear liquid may improve tear flow to the regenerating epithelium near the epithelial defect so as to promote regeneration of the epithelium over the defect. The pumping of the tear liquid can also promote delivery of a medicament, for example a steroid, to the ablated region so as to inhibit corneal infiltrates and haze.

In many embodiments, the covering can be identified based on one or more of pre-operative eye data used to determine the ablation, ablation data of the laser such as the amount of ablative correction, and dimensions across the ablated region of the eye. The covering may comprise an inner portion having a lower surface comprising a curvature, and the curvature can be less than a curvature of the ablated profile to improve vision and inhibit formation of one or more irregularities of the epithelium. The one or more irregularities may be located on an inner portion of the ablation comprising a center of the ablation, and the covering may comprise a resistance to deflection to inhibit formation of the one or more irregularities near the center of the ablation. The irregularity may comprise an elevated profile of the epithelium located on the inner portion comprising the center of the ablation, and the inner portion of the covering may comprise resistance to deflection and provide pressure in response to deflection of the inner portion so as to inhibit formation of the one or more irregularities of the epithelium. As the covering can resist deflection, the covering can be identified based on eye measurement data and ablation data so as to provide comfort and improved vision to the patient when the covering is placed on the eye and improves vision. A plurality of coverings having portions sized to fit the patient can be provided. A covering to treat the patient can be identified among the plurality of coverings based on data corresponding to an untreated portion of the eye, data corresponding to a treated portion of the eye, and an array of data corresponding to rigidity of the plurality of coverings. The array of data may comprise the unique identifiers arranged such that the unique identifier can be determined from the array based on the data corresponding to an untreated portion of the eye and the data corresponding to a treated portion of the eye. The identified covering can be placed on the eye and promote regeneration of the epithelium with improved vision and comfort.

In a first aspect, embodiments provide a method of treating an eye of a patient, in which the eye has a cornea. The eye is measured to determine data of the eye corresponding to an inner ablated portion of the cornea and an outer unablated portion of the cornea away from the ablated portion. A covering of a plurality of coverings is identified to treat the eye based on the data of the eye and an array of data corresponding to the plurality of therapeutic coverings.

In many embodiments, the covering is placed on the eye.

In many embodiments, the covering comprises an inner covering portion and an outer covering portion, the inner covering portion contacting the inner ablated portion of the cornea and an outer covering portion contacting an unablated portion when placed on the cornea and wherein the inner covering portion prior to placement on the eye has a covering curvature no more than a curvature of the ablated portion of the cornea and wherein the outer covering portion comprises a curvature prior to placement on the eye no more than the outer unablated portion of the cornea and wherein the covering resists movement of the inner portion when placed on the eye.

In many embodiments, the outer portion of the covering extends to a conjunctiva of the eye and couples to the sclera of the eye to resist movement of the inner portion.

In many embodiments, the inner portion of the covering prior to placement comprises a substantially uniform thickness and an amount of curvature corresponding to less optical power than the optical power of the ablated portion of the cornea, the amount of curvature of the inner portion prior to placement within a range from about −1D to about −3D relative to the ablated portion of the cornea.

In many embodiments, the inner portion of the covering deflects at least about 1D so as to conform at least partially to the ablation and promote smooth epithelial regeneration and vision.

In many embodiments, the inner portion of the covering comprises an amount of rigidity within a range from about 1E-4 to about 5E-4 (Pa*m^3) and the outer portion of the covering comprises an outer amount of rigidity less than the amount of rigidity of the inner portion.

In many embodiments, measuring the eye comprises determining a conjunctiva sag height, in which the conjunctiva sag height corresponds to a portion of a conjunctiva of the eye at a radial location away from a reference axis of the eye. The covering comprises a covering sag height at a covering location corresponding to the radial location of the portion of conjunctiva, and the covering is identified such that the covering sag height is greater than the conjunctiva sag height.

In many embodiments, the covering is deflected at the covering location when the covering is placed on the eye.

In many embodiments, the conjunctiva sag height is determined based on a measurement of a sclera of the eye corresponding to the radial location.

In many embodiments, measuring the eye comprises determining a limbus sag height, the limbus sag height corresponding to a portion of a limbus of the eye at a radial location away from a reference axis of the eye and wherein the covering comprises a covering sag height at a covering location corresponding to the radial location of the portion of the limbus and wherein the covering is identified such that the covering sag height is no more than the limbus sag height.

In many embodiments, the covering is deflected a first amount at a first covering location corresponding to a portion of the conjunctiva when the covering is placed on the eye and wherein the covering is deflected a second amount at a second covering location corresponding to a portion of the limbus when the covering is placed on the eye, the second amount less than the first amount such that pressure from the covering to the limbus is inhibited.

In many embodiments, the covering comprises an inner portion having a hydrogel layer extending along a lower surface to contact the ablated portion and the unablated portion of the cornea and wherein the covering comprises an outer portion comprising a sticky, tacky surface to contact the conjunctiva and inhibit movement of the covering when the inner portion contacts the cornea In another aspect, embodiments provide an apparatus to treat an eye. The apparatus comprises an input to receive data of the eye. The data of the eye corresponds to an inner ablated portion of the cornea and an outer portion of the cornea away from the inner ablated portion. The apparatus comprises an output. At least one processor is coupled to the input and the output. The at least one processor comprises at least one computer readable memory. The at least one computer readable memory has instructions to store an array of data corresponding to a plurality of therapeutic coverings and instructions to identify a covering of the plurality based on the array and the data of the eye corresponding to the inner ablated portion and the outer portion.

In many embodiments, the apparatus comprises the plurality of coverings.

In many embodiments, the instructions are configured to identify a covering having an inner portion comprising a lower surface curvature flatter than the inner ablated portion of the eye to inhibit one or more irregularities of the epithelium.

In many embodiments, the lower surface curvature of the identified covering is flatter prior to placement than the inner ablated portion of the eye by at least about 1D.

In many embodiments, the inner portion of the covering comprises a substantially uniform thickness and the instructions are configured to identify a covering prior to placement corresponding to hyperopia of the eye to improve vision and inhibit an epithelial irregularity located on an inner portion of the ablation and corresponding to nearsightedness of the eye.

In many embodiments, the instructions are configured to identify the covering to inhibit formation of the epithelial irregularity based on one or more of a modulus of the inner portion of the covering, a thickness of the inner portion of the covering, or an amount of rigidity of the inner portion of the covering.

In many embodiments, the array of data comprises a plurality of unique identifiers corresponding to the plurality of coverings.

In many embodiments, the plurality of unique identifiers corresponds to a rigidity of an inner portion of each of the plurality of coverings.

In many embodiments, the covering comprises an amount of rigidity of the inner portion within a range from about 1E-4 Pa*m^3 to about 5E-4 Pa*m^3.

In many embodiments, the plurality of unique identifiers comprises 10 or more unique identifiers corresponding to an amount of rigidity of the inner portion of at least about 3E-4 Pa*m^3.

In many embodiments, the covering comprises an amount of rigidity of the inner portion within a range from about 1E-4 Pa*m^3 to about 5E-4 Pa*m^3.

In many embodiments, the array of data comprises a first dimension corresponding to the inner ablated portion and a second dimension corresponding to the outer portion away from the ablated portion.

In many embodiments, the array comprises a table, the first dimension corresponding to rows of the table, the second dimension corresponding to columns of the table and wherein the plurality of unique identifiers is stored in the rows and the columns of the table.

In many embodiments, the display is visible to the user and the instructions are configured to show the unique identifier on the display.

In many embodiments, the instructions are configured to receive a conjunctiva sag height, the conjunctiva sag height corresponding to a portion of a conjunctiva of the eye at a radial location away from a reference axis of the eye. The instructions are configured such that the identified covering comprises a covering sag height at a covering location corresponding to the radial location of the portion of conjunctiva and wherein the instructions are configured such that the covering sag height is greater than the conjunctiva sag height.

In many embodiments, the covering comprises an inner portion having a hydrogel layer extending along a lower surface to contact the ablated portion and the unablated portion of the cornea, and the covering comprises an outer portion at the covering location comprising a sticky tacky surface to contact the conjunctiva and inhibit movement of the covering when the inner portion contacts the cornea.

In many embodiments, the inner portion of the covering comprises a low water content water inhibiting layer beneath the hydrogel layer, and the outer portion of the covering at the covering location to contact the conjunctiva comprises a soft hydrophobic material.

In many embodiments, the water inhibiting layer comprises silicone elastomer and the hydrogel layer comprises silicone hydrogel.

In many embodiments, instructions are configured such that the identified covering is deflected at the covering location when the covering is placed on the eye.

In many embodiments, the instructions are configured to receive the conjunctiva sag height based on a measurement of a sclera of the eye corresponding to the radial location.

In many embodiments, the instructions are configured to receive a measurement the eye corresponding to a limbus sag height, in which the limbus sag height corresponds to a portion of a limbus of the eye at a radial location away from a reference axis of the eye. The instructions are configured such that the covering comprises a covering sag height at a covering location corresponding to the radial location of the portion of limbus, and the instructions are configured such that the covering sag height is no more than the limbus sag height.

In many embodiments, the instructions are configured to identify the covering such that the identified covering is deflected a first amount at a first covering location corresponding to a portion of the conjunctiva when the covering is placed on the eye, and the instructions are configured to identify the covering such that the covering is deflected a second amount at a second covering location corresponding to a portion of the limbus when the covering is placed on the eye, the second amount less than the first amount such that pressure from the covering over the limbus is inhibited.

In another aspect embodiments provide an apparatus to treat an eye. The apparatus comprises an input, an output and at least one processor. The input is configured to receive data of the eye, and the data of the eye correspond to an inner portion of the cornea and one or more of a limbus or a conjunctiva of the eye. The at least one processor is coupled to the input and the output. The at least one processor comprises at least one computer readable memory. The at least one computer readable memory has instructions to store an array of data corresponding to a plurality of coverings and instructions to identify a covering of the plurality based on the data of the eye and the array of data corresponding to the plurality of coverings, such tear liquid is pumped under the covering when the eye blinks.

BRIEF DESCRIPTION OF THE DRAWINGS

FIG. 1-1A shows an ablated eye immediately following refractive surgery resulting in an epithelial defect, suitable for incorporation in accordance with embodiments of the present invention;

FIG. 1-1B shows an ablated eye about 1 day following refractive surgery resulting in an epithelial defect, suitable for incorporation, in accordance with embodiments of the present invention;

FIG. 1-1C shows an ablated eye when the epithelium has regenerated following refractive surgery resulting in an increased epithelial thickness centrally at about 3 days, suitable for incorporation, in accordance with embodiments of the present invention;

FIG. 1-2A shows a covering positioned on an eye having an epithelial defect, in which the covering abuts the cornea to seal the cornea, in accordance with embodiments of the present invention;

FIG. 1-2B shows a smooth layer of regenerated epithelium substantially cover an ablated profile, in accordance with embodiments of the present invention;

FIG. 1A shows a covering positioned on an eye having an epithelial defect, in which an outer portion of the covering abuts and conforms at least partially to the cornea to seal the cornea, in accordance with embodiments of the present invention;

FIG. 1A1 shows a covering positioned on an eye and blinking of the eye, in accordance with embodiments of the present invention;

FIG. 1B1 shows a covering sized to seal a cornea, in accordance with embodiments of the present invention;

FIG. 1B2 shows the covering conforming to ablated stromal tissue and guiding regeneration of the epithelium over the ablated stroma, so as to promote vision, in accordance with embodiments of the present invention;

FIG. 1B2A shows a covering forming an indentation in the epithelium such that the epithelium extends over at least a portion of the perimeter of the covering, in accordance with embodiments of the present invention;

FIG. 1B2B shows a covering forming an indentation in the epithelium, in accordance with embodiments of the present invention;

FIG. 1B2C shows a covering abutting the cornea to seal the cornea without forming a substantial indentation in the epithelium, in accordance with embodiments of the present invention;

FIG. 1C shows a covering comprising a single piece of material having an inner thickness greater than an outer thickness, in accordance with embodiments of the present invention;

FIG. 1C1 shows a covering as in FIGS. 1-2A to 1B2 having an inner portion comprising an inner thickness and an inner material and an outer portion comprising an outer thickness and an outer material, in which the inner thickness is greater than the outer thickness, in accordance with embodiments of the present invention;

FIG. 1C1A shows a covering as in FIG. 1C1 adhered to the cornea with a smooth upper surface and a lower surface conforming to irregularity of the cornea comprising a central island of the stroma, in accordance with embodiments of the present invention;

FIG. 1C2 shows a covering as in FIGS. 1-2A to 1B2 having an inner portion comprising an inner thickness and an inner material and an outer portion comprising an outer thickness and an outer material, in which the inner thickness is greater than the outer thickness and the outer material extends around the inner material, in accordance with embodiments of the present invention;

FIG. 1C2A shows a covering as in FIG. 1C1 adhered to the cornea with a smooth upper surface and a lower surface conforming to irregularity of the cornea near the edge of the ablation, in accordance with embodiments of the present invention;

FIG. 1C2A1 shows a covering having a layer of hydrogel material on a posterior surface of the covering, in accordance with embodiments of the present invention;

FIG. 1C2B shows a covering having a layer of hydrogel material on a posterior surface of the covering extending less than a maximum distance across the covering such that end portions of the covering are configured to engage the epithelium of the eye away from the hydrogel layer and inhibit movement of the covering when placed on the eye, in accordance with embodiments of the present invention;

FIG. 1C2C shows a covering having an annular layer of hydrogel material on a posterior surface of the covering such that an inner portion of the covering contacts the cornea away from the hydrogel layer and an outer portion of the covering contacts the cornea away from the covering when placed on the eye, in accordance with embodiments of the present invention;

FIG. 1C3 shows a covering having a tricurve profile to fit sclera with slopes of the curved profiles aligned so as to inhibit ridges at the boundaries of the curved portions as in FIG. 1B2 and having a layer of hydrogel material on a lower surface, in accordance with embodiments of the present invention;

FIG. 1C4 shows a side cross-sectional view covering having a tricurve profile to fit the cornea, limbus and sclera with slopes of the curved profiles aligned so as to inhibit ridges at the boundaries of the curved portions and having a hydrogel material on a lower surface extending less than a maximum distance across the covering to engage the conjunctiva with the covering away from the hydrogel material, in accordance with embodiments of the present invention;

FIG. 1C5 shows a fenestration having a posterior end covered with a layer of hydrogel extending along the posterior surface of the covering, in accordance with embodiments of the present invention;

FIG. 1C6 shows a fenestration extending through a layer of hydrogel extending along the posterior surface of the covering, in accordance with embodiments of the present invention;

FIG. 1G shows a covering comprising an inner portion and an outer portion comprising a taper, in accordance with embodiments of the present invention;

FIG. 1G1 shows a covering comprising an inner portion and an outer portion comprising a taper and an outer rim of substantially uniform thickness peripheral to the taper, in accordance with embodiments of the present invention;

FIGS. 1G1A to 1G1G show a covering as in FIG. 1G1 and dimensions suitable for use with experiments, clinical studies, and patient treatment, in accordance with embodiments of the present invention;

FIG. 1H1 shows spatial frequency and elevation smoothing of an epithelial irregularity transferred to a front surface of a covering as in FIG. 1-2A, in accordance with embodiments of the present invention;

FIG. 1H2 shows spatial frequency and elevation smoothing of the epithelial irregularity with a plot of height relative to a reference sphere for the upper surface of the covering and the upper surface of the irregularity, in accordance with embodiments of the present invention;

FIG. 1I1 shows inhibition of transfer of an epithelial irregularity to a front surface of a covering, in accordance with embodiments of the present invention;

FIG. 1I2 shows elevation smoothing of the epithelial irregularity with a plot of height relative to a reference sphere for the upper surface of the covering and the upper surface of the irregularity, in accordance with embodiments of the present invention;

FIG. 1I3 shows a thickness profile of the covering as in FIG. 1I2 so as to smooth the front surface of the covering, in accordance with embodiments of the present invention;

FIG. 1J1 shows a covering having a bicurve profile to fit an ablated cornea, in accordance with embodiments of the present invention;

FIG. 1J2 shows a covering having an oblate profile to fit an ablated cornea, in accordance with embodiments of the present invention;

FIG. 1J3 shows a covering having a tricurve profile to fit sclera and an ablated cornea, in accordance with embodiments of the present invention;

FIG. 1J4 shows a covering having a curved profile to fit sclera and an oblate profile to fit ablated cornea, in accordance with embodiments of the present invention;

FIG. 1J5 shows a covering having a tricurve profile to fit sclera and an ablated cornea similar to FIG. 1J3, in accordance with embodiments of the present invention;

FIG. 1J6 shows a tapered edge of the covering having a tricurve profile to fit sclera and an ablated cornea as in FIG. 1J5, in accordance with embodiments of the present invention;

FIG. 2A1 shows a covering positioned on an eye and blinking of the eye, in accordance with embodiments of the present invention;

FIG. 2A2 shows the covering of FIG. 2A1 that is capable of pumping tear liquid under the covering, in accordance with embodiments of the present invention;

FIG. 2A3 shows a schematic illustration of the covering of FIGS. 2A1 and 2A2 pumping tear liquid when the eye closes, in accordance with embodiments of the present invention;

FIG. 2A4 shows a schematic illustration of the covering of FIGS. 2A1 and 2A2 pumping tear liquid when the eye opens, in accordance with embodiments of the present invention;

FIG. 2B1 shows a covering having a tricurve profile to fit sclera, which covering may be used to fit an ablated cornea, in accordance with embodiments of the present invention;

FIG. 2B2 shows a covering having a tricurve profile to fit sclera with slopes of the curved profiles aligned so as to inhibit ridges at the boundaries of the curved portions, in accordance with embodiments of the present invention;

FIG. 2B2-1 shows alignment of the slope of the lower surface of the corneal contacting portion with the slope of the lower surface of the sclera coupling portion, such that pressure to the limbus is decreased substantially, in accordance with embodiments of the present invention;

FIG. 2B3 shows a tapered edge of the covering of FIG. 2B1, in accordance with embodiments of the present invention;

FIG. 2B4 shows a plan view of the covering having a tricurve profile to fit the cornea, limbus, and sclera with slopes of the curved profiles aligned so as to inhibit ridges at the boundaries of the curved portions, in accordance with embodiments of the present invention;

FIG. 2B5 shows a side sectional view of the covering of FIG. 2B4 and corresponding curved portions to couple to the cornea, limbus and, sclera, in accordance with embodiments of the present invention;

FIG. 2B6 shows a side sectional view of the covering of FIG. 2B4 and corresponding curved portions of the upper surface, in accordance with embodiments of the present invention;

FIG. 2B7 shows a tapered edge of the covering of FIG. 2B4, in accordance with embodiments of the present invention;

FIG. 3F1 shows a side sectional view of the covering of FIG. 3F with rotation of the eye when the lids close such that sliding of the covering along the epithelium is inhibited when tear liquid is pumped, in accordance with embodiments of the present invention;

FIG. 4 shows apparatus and coverings to treat an eye, in accordance with embodiments of the present invention;

DETAILED DESCRIPTION OF THE INVENTION

Figure 1:
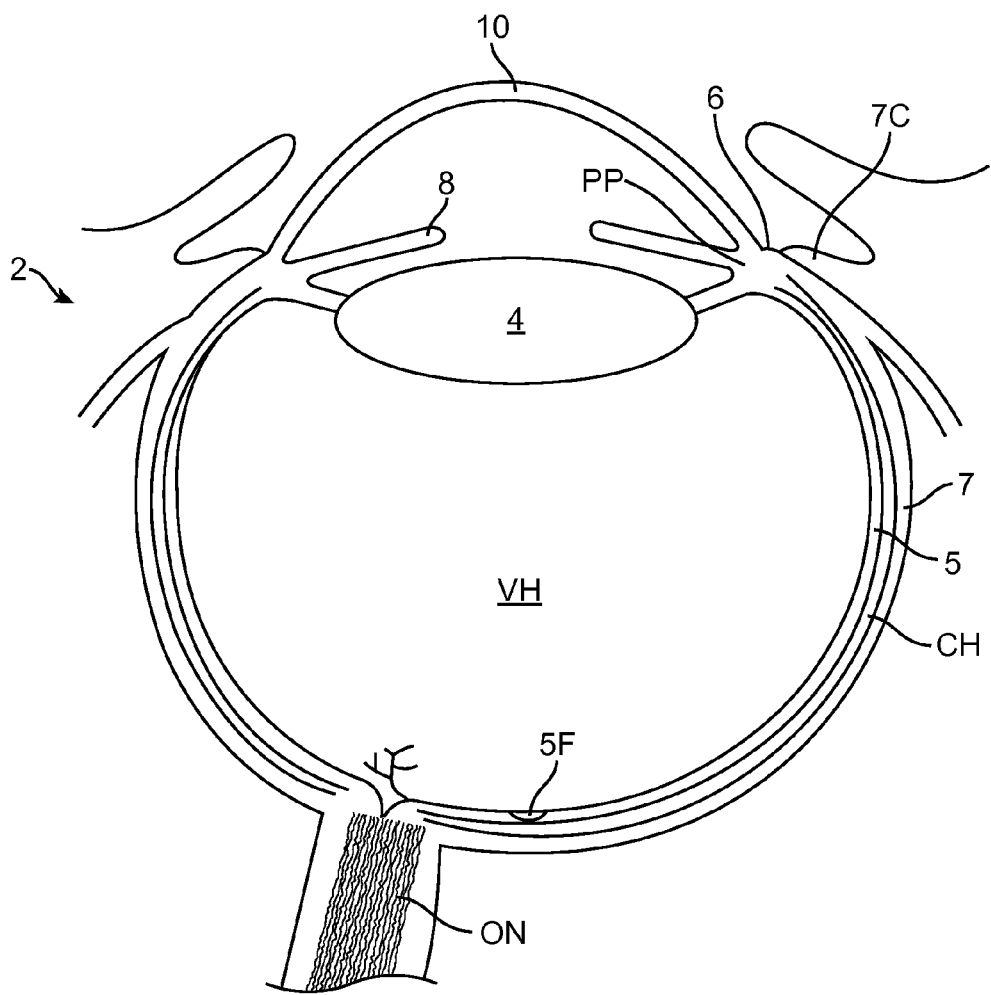
FIG. 1 shows an eye suitable for incorporation of the covering as described herein, in accordance with embodiments of the present invention.

Embodiments of the present invention as described herein can be combined with the therapeutic covering device for pain management and vision as described in U.S. patent application Ser. No. 12/384,659, filed Apr. 6, 2009, entitled "Therapeutic Device for Pain Management and Vision", the full disclosure of which is incorporated herein by reference and suitable for combination in accordance with some embodiments of the present invention as described herein.

The embodiments described herein can be used to treat eyes in many ways with a covering. Although specific reference is made to treating epithelial defects of the eye, the covering described herein can be used for long term vision correction with extended wear contact lenses that inhibit swelling of the cornea when the covering is positioned on the eye for an extended period.

The coverings as described herein can seal the cornea, so as to restore deturgescence of the cornea to decrease pain and improve vision. The covering can be configured in many ways to seal the cornea, and the covering comprises a substantially oxygen permeability to promote growth of the epithelium and to guide the growth of the epithelium such that the epithelium regenerates smoothly for patient vision. The restoration of deturgescence of the cornea can decrease irregularities of the cornea such as ablated stromal irregularities, for example central islands. The sealing of the cornea with the environment to promote epithelial regeneration can result in improved epithelial smoothness and an improved profile of the ablated stromal surface under the regenerating epithelium.

In many embodiments, the covering comprises an at least partially conformable portion, such that the at least partially conformable portion can one or more of match or grossly approximate the corrected corneal curvature so as to provide vision of at least about 20/30, and such that the at least partially conformable portion substantially does not conform to the corneal irregularities caused by epithelial healing and edema, such as irregularities of the epithelium and central islands that may appear post-ablation in ablated eye.

In many embodiments, the at least partially conformable portion of the covering can be configured so as to conform at least partially to the epithelium when the covering is positioned on the epithelium so as to deflect the epithelium.

The epithelium can conform to the covering so as to seal the covering, for example with deformation of the epithelium such as with one or more of indentation or overgrowth of the epithelium around a perimeter of the covering.

In many embodiments, the curvature of the covering can match substantially the profile of the ablated region, so as to provide visions of at least about 20/30 when positioned on the cornea.

As used herein, mathematical equations and scientific notation can be used to values in many ways understood by a person of ordinary skill in the art, for example so as to express data in accordance with notations used in many commercially available spreadsheets such as Excel™ commercially available from Microsoft. As used herein the symbol "E" can be used to express an exponent in base 10, such that 1E1 equals about 10, 2E1 equals about 20, and 4E2 equals about 400. As used herein the symbol "^" can be used to express an exponent, such that A^B equals $A^B$. Units can be expressed in many ways and as would be understood by a person of ordinary skill in the art, for example "m" as meters, "Pa" as the Pascal unit for pressure, and "MPa" as Mega Pascal.

FIG. 1 shows an eye 2 suitable for incorporation of the covering 100 as described herein. The eye has a cornea 10 and a lens 4 configured to form an image on the retina 5, and the image can form on a fovea 5F corresponding to high visual acuity. The cornea can extend to a limbus 6 of the eye, and the limbus can connect to a sclera 7 of the eye. The eye 2 has a pars plana PP located near limbus 6. A conjunctiva 7C of the eye can be disposed over the sclera 7. The lens can accommodate to focus on an object seen by the patient. The eye has an iris 8 that defines a pupil 9 that may expand and contract in response to light. The eye also comprises a choroid CH disposed between the sclera 7 and the retina 5. The eye has a vitreous humor VH extending between the lens and the retina. The retina 5 senses light of the image and converts the light image to neural pulses that are processed and transmitted along an optic nerve ON to the brain of the patient.

Figures 1, 1A:
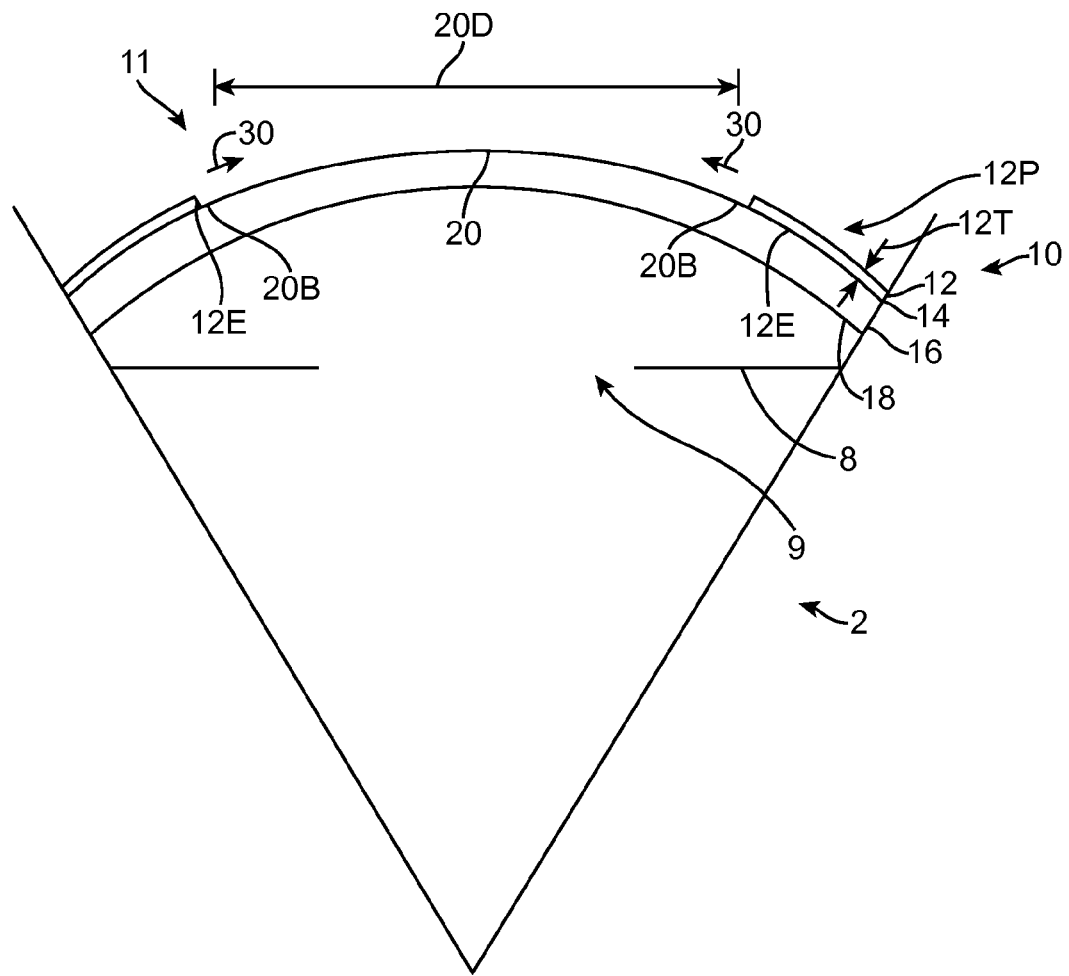

FIG. 1-1A shows an ablated eye immediately following refractive surgery, for example PRK surgery resulting in an epithelial defect. The eye 2 comprises an iris 8 that defines a pupil 9, through which light passes such that the patient can see. Cornea 10 includes an epithelium 12 disposed over a stroma 16. The epithelium 12 comprises an unablated outer-peripheral portion having 12P having a thickness 12T that can be about 50 um. A tear liquid covers the anterior surface of epithelium 12. In at least humans, primates and some birds, a Bowman's membrane 14 is disposed between epithelium 12 and stroma 16. Bowman's membrane 14 comprises an acellular substantially collagenous tissue with a thickness of about 5 to 10 microns. Stroma 16 comprises a substantially collagenous tissue with keratocytes disposed therein. In some animals, Bowman's membrane may be absent and the epithelium may be disposed adjacent to the stromal layer. An endothelium 18 is disposed under stroma 16. Endothelium 18 comprises a layer of cells that pump water from cornea 10 toward iris 8. Tear liquid also covers surfaces of the cornea that are exposed by the epithelial defect, such as an exposed surface of Bowman's membrane and an exposed stromal surface.

In a normal healthy eye, epithelium 12 is disposed across cornea 10 and is a protective layer. Epithelium 12 covers nerves of the cornea and minimizes the flow of water from the tear film of the eye to into the stroma. Epithelium 12 in most human patients can be about 40 to 60 microns thick, for example about 50 microns. When epithelium 12 is intact, endothelium 18 can pump water from stroma 16 and maintain hydration in the cornea at a proper level. The mechanism by which the stroma of the cornea remains properly hydrated can be referred to as deturgescence. Deturgescence of the cornea can be important because excess hydration of the cornea can result in swelling of the cornea and light scattering, or haze, that can degrade vision. The total thickness of normal cornea 10 from endothelium 18 to tear liquid in most human patients can be from about 400 to 600 microns. A healthy cornea with normal hydration comprises about 80 to 85% water. Edema of the cornea due to swelling of the cornea, for example with additional water, can increase the thickness of the cornea.

With refractive surgery, for example PRK, the epithelium can be removed to ablate a refractive correction into Bowman's membrane 14 and/or stroma 16. An initial profile of the anterior surface of stroma and/or Bowman's membrane is ablated to an ablated profile 20 to correct the patient's vision. The profile of tissue removed to correct vision is described in U.S. Pat. No. 5,163,934, entitled "Photorefractive Keratectomy", the disclosure of which may be suitable for combination in accordance with some embodiments of the present invention described herein. Ablated profile 20 generally comprises an optical zone that extends across the cornea to correct refractive error of the eye and may correct aberrations of the eye, for example wavefront aberrations. Ablated profile 20 is bounded by boundary 20B that may circumscribe the ablated profile. The ablation profile 20 comprises a maximum dimension across, for example a diameter 20D.

The epithelium may comprise an inner boundary that moves centripetally inward as indicated by arrows 30

Figures 1, 1B:
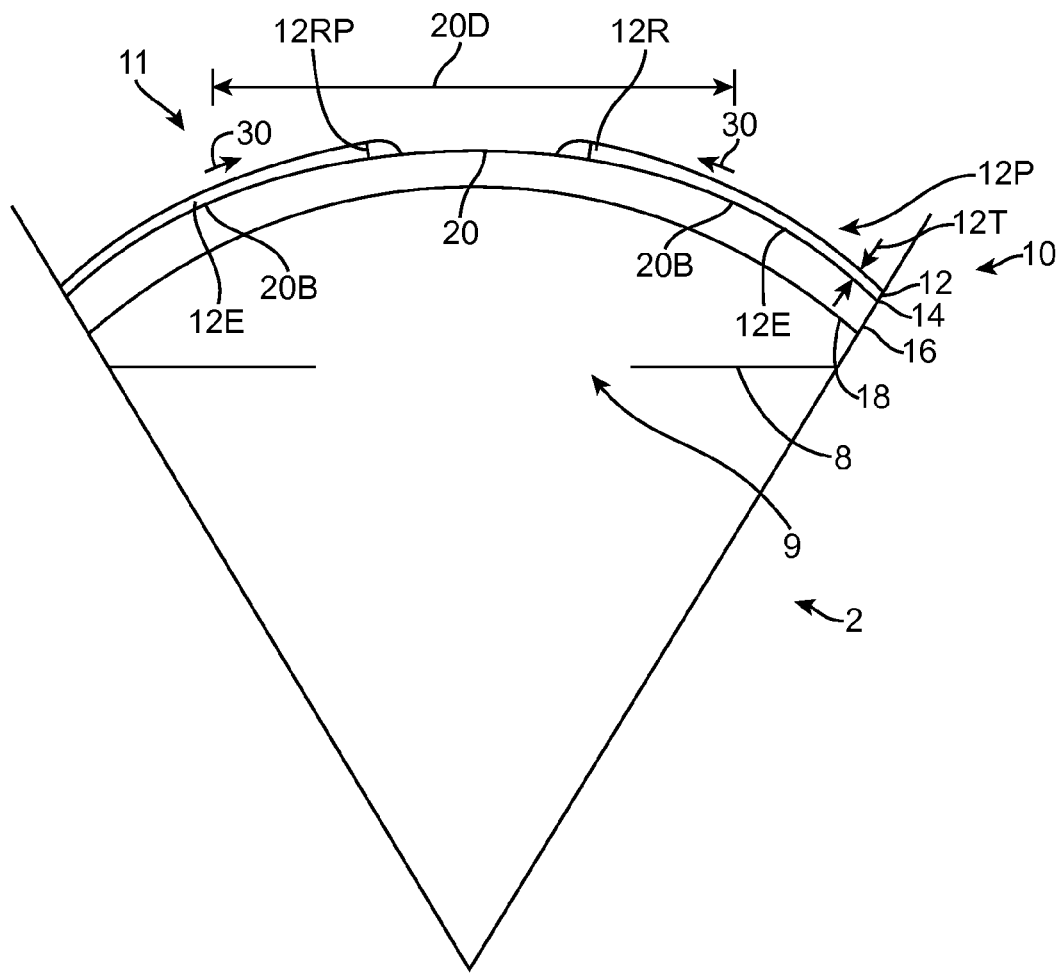

FIG. 1-1B shows an ablated eye about 1 to 2 days following refractive surgery resulting in an epithelial defect. The epithelium has at least partially covered the ablation. The epithelium may comprise irregularities and an inner boundary that moves centripetally inward as indicated by arrows 30. The thickness profile 12RP of the regenerating epithelium 12R can be irregular and degrade vision. The inner portion of the epithelium near the boundary may comprise a height greater than an outer portion of the epithelium away from the boundary of the epithelium. The portion of the ablation not covered with the epithelium and the inner portion of the epithelium near the boundary can result in aberrations, for example aberrations corresponding to a meniscus of the tear and a far sighted portion of the cornea. As variation in epithelial healing among individuals can be observed, the epithelial defect of at least some individuals can be present at 2 and 3 days post-op, with corresponding aberrations.

Figures 1, 1C:
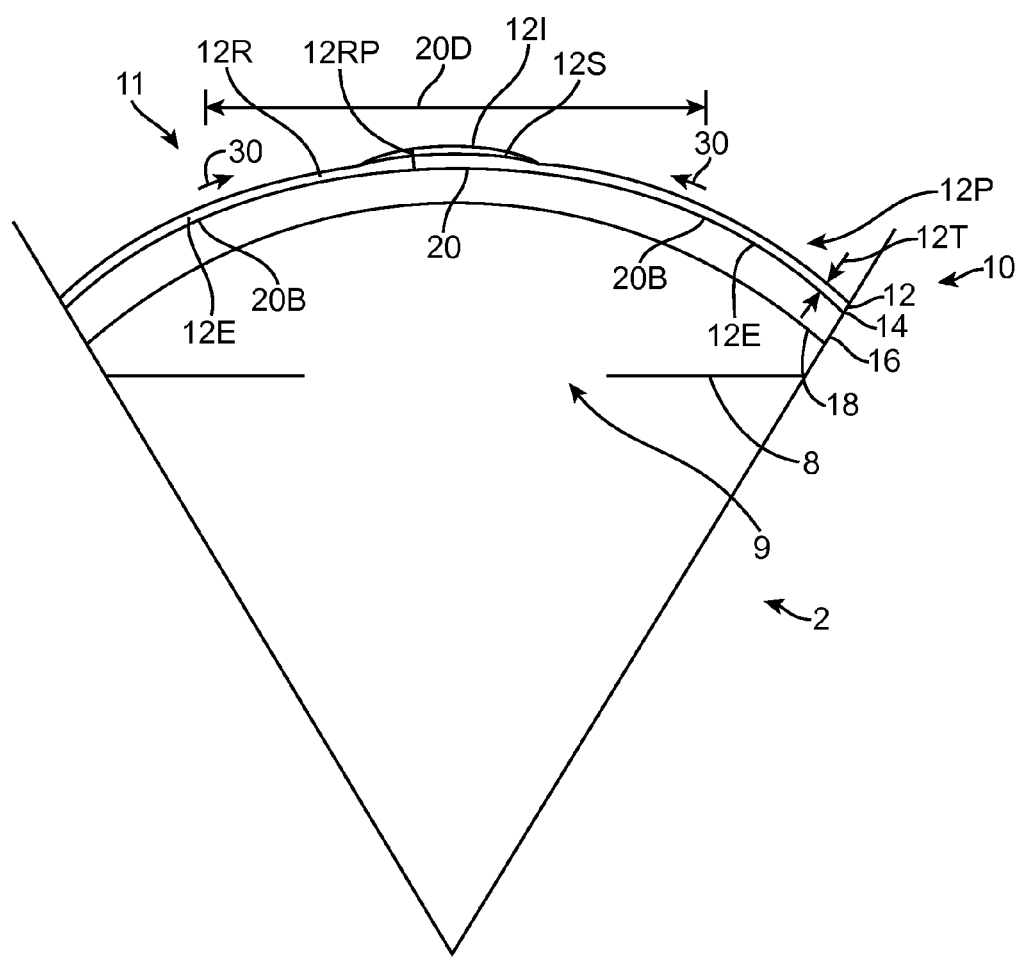

FIG. 1-1C shows an ablated eye when the epithelium has regenerated following refractive surgery resulting in an increased epithelial thickness centrally when the epithelium has regenerated, for example at about 3 days post-op. The regenerating epithelium may have an irregularity 12I, for example corresponding to an increased elevation of an inner portion of the epithelium near the center of the ablation, for example. Work in relation to embodiments as described herein suggests that the natural regeneration of the epithelium can provide an inner portion having an increased central elevation with optical power that may correspond to about 1 to 3 Diopters of additional optical power. The regenerating epithelium comprises a thickness profile 12RP extending along the surface of Bowman's membrane 14 and the ablation 20. With PRK the thickness profile 12RP of the epithelium can regenerate for at least one week, for example one month, such that vision can be degraded when the thickness profile 12RP of the epithelium regenerates, and PRK surgery of the cornea can be combined in accordance with embodiments described herein so as to improve vision.

In many embodiments as described herein, irregularities of the cornea are decreased when the epithelium regenerates so as to provide one or more of improved vision or comfort. The coverings as described herein can be configured so as to decrease an effect on vision of corneal irregularity 12I, decrease the height profile of irregularity 12I, decrease transfer of irregularity 12I to an anterior surface of the covering, smooth irregularity 12I with the covering, regenerate epithelium 12 such that irregularity 12I is decreased, or combinations thereof. In many embodiments, the covering 100 as described herein can be placed on the eye such that a smooth layer 12S of regenerated epithelium 12R substantially covers the ablated profile so as to provide improved vision sooner than would occur without covering, for example at about 3 to 4 days post-op with PRK. In many embodiments, the covering can provide an environment 100E as described herein so as to guide epithelial regeneration and smooth the regenerated epithelium.

In many embodiments, the cornea 10 of an eye 2 has an epithelial defect 11 following refractive surgery such as PRK, and a covering 100 positioned over the epithelial defect 11.

Figures 1, 2, 2A:
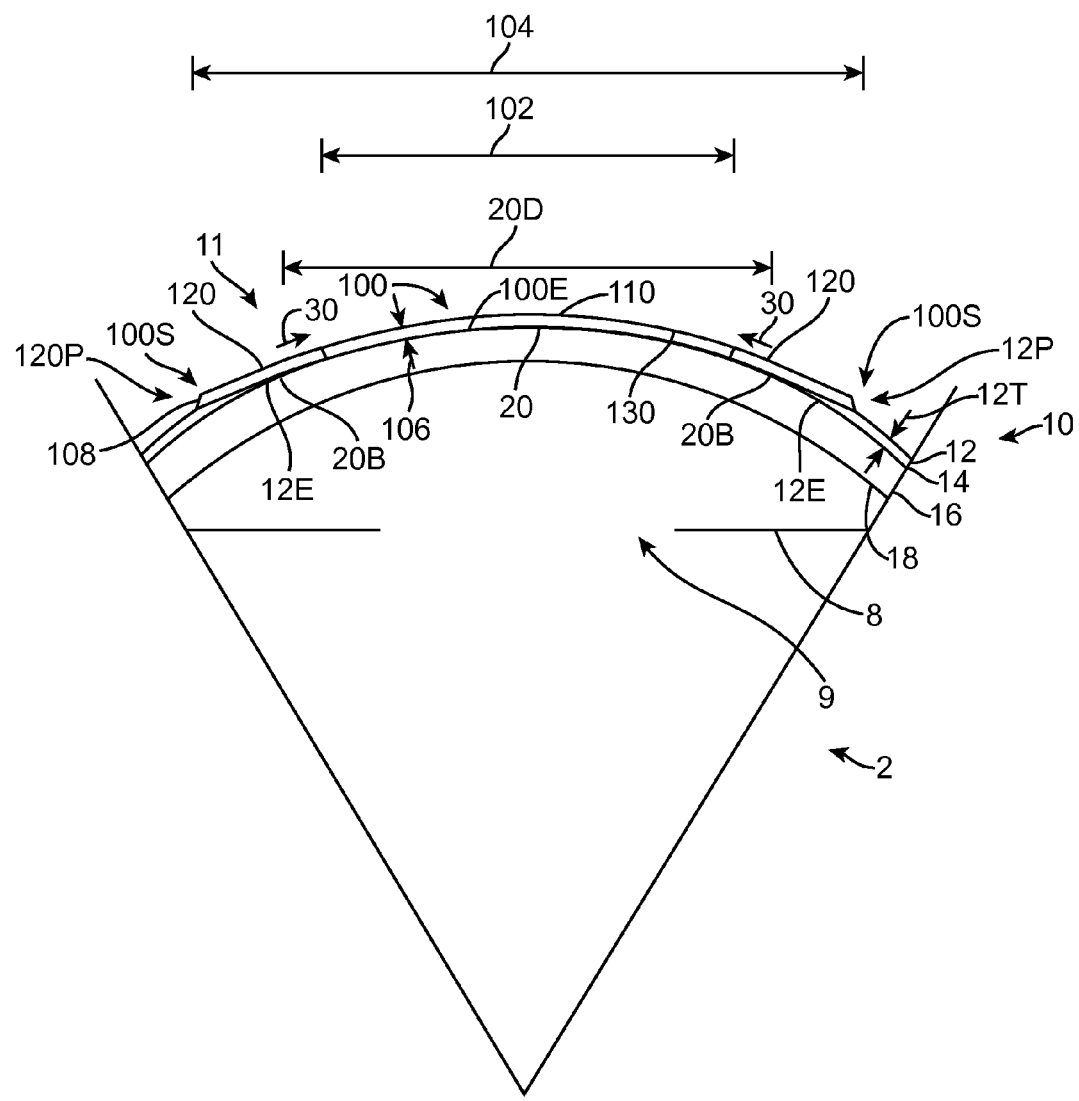

FIG. 1-2A shows a covering 100 positioned on cornea 10 an eye 2 having an epithelial defect 11, in which the covering abuts the cornea to seal the cornea. The covering may comprise a curved body, for example a curved contact lens body shaped to fit the cornea.

The covering 100 can be sized to cover the ablated profile and epithelial defect. The inner portion 110 comprises a dimension across 102 that can be sized to extend across a majority of the ablation, and the outer portion 120 comprises a dimension across 104 sized to extend across at least the epithelial defect and contact the epithelium on opposite sides of the defect.

The dimension 102 extending across a majority of the ablation may extend about 6 to 8 mm, for example, and may be sized larger than the ablation. The dimension 104 may comprise about 12 to 14 mm across, for example so as to extend to the limbus and can be sized to the limbus of the patient for example. Work in relation to embodiments suggests that the covering sized to extend to the limbus and circumferentially around the limbus can be centered on the cornea. The covering may extend such that the outer rim of the covering contacts the conjunctiva disposed above the sclera peripheral to the limbus, for example, and that such configurations may center the lens on the cornea, for example.

The thickness of the covering can be sized and shaped in many ways. The inner portion 110 of the covering comprises a thickness 106 and the outer portion 120 of the covering comprises a thickness 108. The thickness 106 of the inner portion may comprise a substantially uniform thickness such that the inner portion comprises an optical power of no more than about +/−1D prior to placement on the eye, for example when held in front of the eye and separated from the cornea by a distance. Alternatively, the thickness of the inner portion may vary so as comprise optical power, for example optical power to correct vision of the patient.

Figures 1, 2, 2B:
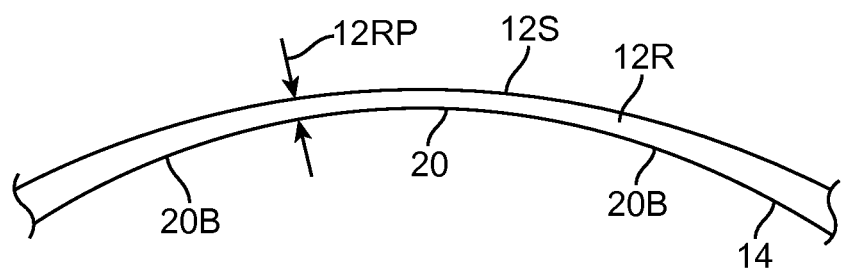
Figure 1A:
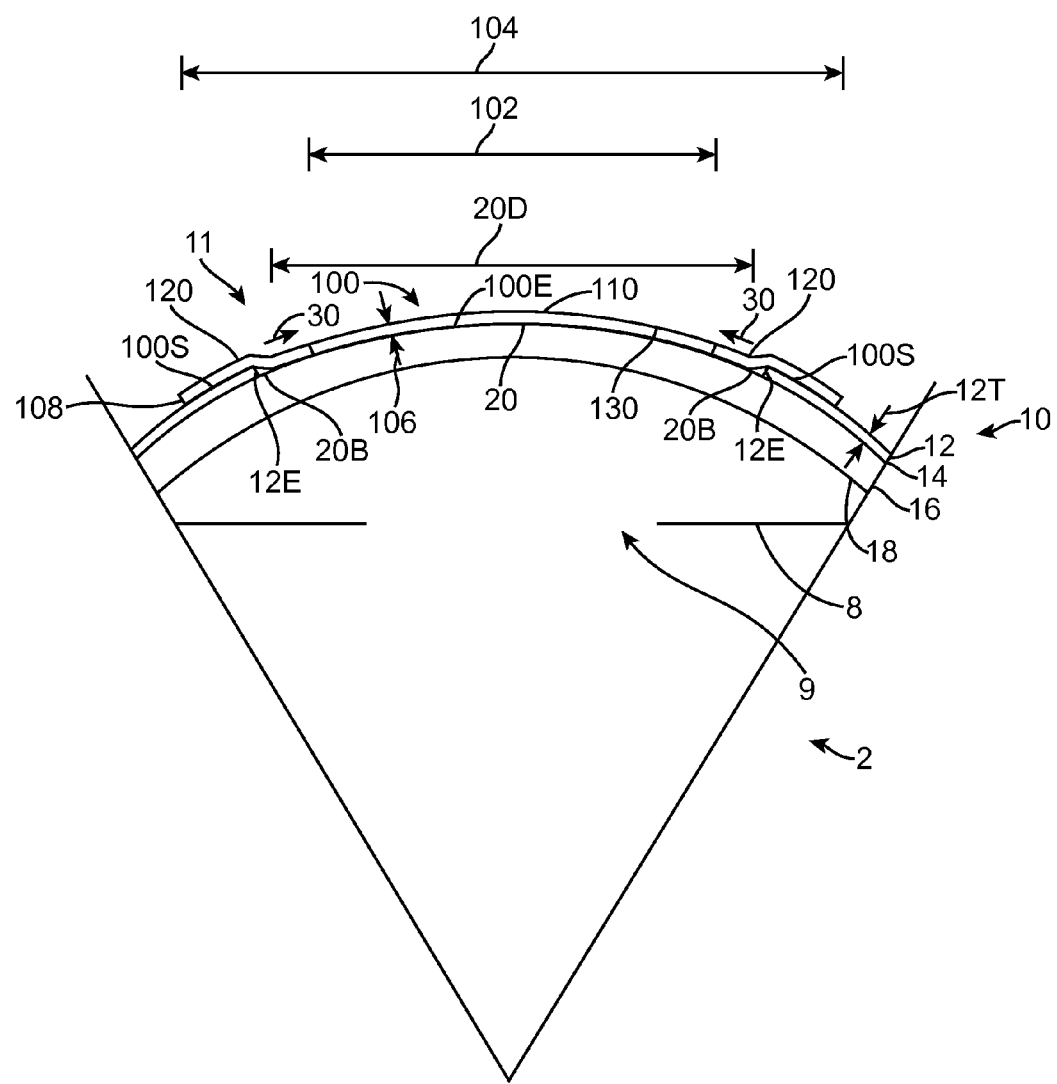

FIG. 1-2B shows a smooth layer 12S of regenerated epithelium 12R substantially covering an ablated profile. The environment 100E is configured to guide epithelial regeneration and smooth the regenerated epithelium. The regenerating epithelium comprises a thickness profile 12RP.

The epithelium grows centripetally from circumscribing boundary 12E toward the center of ablated profile 20 to cover the exposed stroma, as indicated by arrows 30.

The covering 100 may comprise an inner portion 110 and an outer portion 120. The outer portion 120 can be configured to form a seal 100S with the cornea near the edge of the ablation and the epithelial defect, for example with a soft conformable material such as silicone or silicone hydrogel. The inner portion 110 is positioned over the pupil and configured for the patient to see, and may comprise a rigidity greater than the outer portion, so as to smooth irregularities of the epithelium when the cornea heals. Alternatively, the inner portion may comprise a rigidity equal to or less than the rigidity of the outer portion as well. For example, the inner portion may comprise silicone and the outer portion may comprise silicone, and the inner portion may comprise one or more of a more rigid silicone or a greater thickness such that the inner portion can be more rigid than the outer portion so as to smooth the epithelium. Although the inner portion can be more rigid than the outer portion, the inner portion is sufficiently soft, flexible and conformable so as to conform at least partially to the ablated profile 20 in the stroma, such that the patient receives the benefit of the vision correction with the ablation profile 20 when the patient looks through the inner portion and the inner portion smoothes the epithelium. Work in relation to embodiments of the present invention suggests that the regenerating epithelium is softer than the underlying stroma of ablation profile 20, such that the inner portion can be configured to conform to the shape of the ablation profile 20 when the inner portion smoothes the epithelium disposed under the inner portion.

The covering 100 may comprise one or more of many optically clear materials, for example synthetic materials or natural material such collagen based materials, and combinations thereof, such as described in U.S. patent application Ser. No. 12/384,659, filed Apr. 6, 2009, entitled "Therapeutic Device for Pain Management and Vision", U.S. Pub. No. US 2010-0036488 A1, published on 11 Feb. 2010. For example, the lens material may comprise a naturally occurring material, such as collagen based material. Alternatively or in combination, the lens material may comprise a known synthetic material, for example hydroxyethyl methacrylate (HEMA) hydrogel, hydrogel, silicone, for example hydrated silicone and derivatives thereof. For example, the optically clear material may comprise one or more of silicone, silicone hydrogel, silicone comprising resin, silicone comprising silicate, acrylate, orcollagen. The cured silicone may comprise silicone that is two-part heat cured and RTV (room temperature vulcanized). For example, polydimethyl siloxane such as NuSil, or poly(dimethyl) (diphenyl) siloxane may be used to mold the covering, for example with less than 10% water content so as to increase oxygen diffusion through the covering. The covering 100 may comprise perfluoropolyethers or fluorofocal. The lens material can be elastic, for example a stretchable elastic material such as silicone, such that the lens can seal the cornea. The lens material can be cured with a hardness and size and shape such that the covering comprises a modulus within a range from about 4 to about 20 MPa. The material may comprise, for example, silicone elastomer having optically clear silicate disposed therein and a water content of no more than about 10%, for example no more than about 5%, such that the lens covering has a very high Dk exceeding 150, and the silicone lens comprising silicate can be treated to provide a wettable surface. The lens may comprise hydrogel, for example silicone hydrogel, and can be formed with a water content within a range from about 5% to about 35% and a modulus within a range from about 4 to about 20 MPa, such that the covering conforms at least partially to the ablated stroma.

The covering may comprise silicone or silicone hydrogel having a low ionoporosity such that covering seals to the cornea. For example, covering may comprise silicone hydrogel comprising a low ion permeability, and the range of water can be from about 5% to about 35%, such that the Dk is 100 or more. The low ion permeability may comprise an Ionoton Ion Permeability Coefficient of no more than about 0.25× 10-3 cm2/sec so as to seal the cornea, for example no more than about 0.08×10-3 cm2/sec. The low ion permeability comprises an Ionoton Ion Permeability Coefficient of no more than about 2.6×10-6 mm2/min to seal the cornea, for example no more than about 1.5×10-6 mm2/min.

The covering 100 may comprise a wettable surface coating 134 disposed on at least the upper side of the covering, such that the tear film of the patient is smooth over the covering and the patient can see. The wettable surface coating may comprise a lubricious coating for patient comfort, for example to lubricate the eye when the patient blinks. The wettable coating may comprise a contact angle no more than about 80 degrees. For example, the coating may comprise a contact angle no more than about 70 degrees, and the contact angle can be within a range from about 55 to 65 degrees to provide a surface with a smooth tear layer for vision. For example, the wettable coating can be disposed of both an upper surface and a lower surface of the covering. Alternatively, the lower surface may comprise a hydrophobic surface material and the lower hydrophobic surface may comprise the inner portion 110 and the outer portion 120. At least the outer portion 120 may comprise a lower surface composed of a sticky, tacky material, for example a hydrophobic material. The inner portion may also comprise the lower surface comprised of the sticky, tacky, hydrophobic material. The upper surface may comprise the wettable coating extending over at least the inner portion 110.

The wettable coating may comprise one or more of many materials. For example, the wettable coating may comprise polyethylene glycol (PEG), and the PEG coating can be disposed on Parylene™. Alternatively, the wettable coating may comprise a plasma coating, and the plasma coating comprise a luminous chemical vapor deposition (LCVD) film. For example, the plasma coating comprises at least one of a hydrocarbon, for example CH4, O2 or fluorine containing hydrocarbon, for example CF4 coating. Alternatively or in combination, the wettable coating may comprise a polyethylene glycol (PEG) coating or 2-hydroxyethylmethacrylate (HEMA). For example, the wettable coating may comprise HEMA disposed on a Parylene™ coating, or the wettable coating may comprise N-vinylpyrrolidone (NVP) disposed on a Parylene™ coating.

The covering 100 may comprise a lower surface corresponding to one or more of many suitable shapes to fit the covering to the cornea. For example, the lower surface of the covering may correspond to base radius of curvature. With post ablation corneas, the covering may conform substantially to the cornea. The covering may comprise a second curve in combination with a first curve, such that the lower surface comprises a bicurve surface. Alternatively, the lower surface may correspond to an aspheric surface. For example, an aspheric surface may comprise an oblate shape and conic constant to fit a post PRK eye. Also, it may be helpful to fit the covering to the cornea, for example with selection of one covering from a plurality of sizes.

FIG. 1A shows the covering 100 having the thickness 108 of the outer portion sized such that the outer portion can conform to the epithelium. The thickness of the outer portion can be substantially constant, or may vary as described herein below.

FIG. 1A1 shows covering 100 positioned on an eye and blinking of the eye. An upper lid and a lower lid can blink over the eye. Work in relation to embodiments suggests that the upper lid can exert a downward movement 20 and that the lower lid can exert an upper movement 22 on the eye. The downward movement 20 can be greater than the upper movement 22. The wettable coating material as described herein can decrease force and movement transferred from the lids to the covering so as to inhibit motion of the covering. The downward movement 20 greater than the upward movement 22 can affect epithelial growth near the perimeter of covering 100.

FIG. 1B1 shows covering 100 as in FIG. 1-2A prior to placement on the cornea. The covering 100 may comprise a base radius R1 of curvature, and the base radius of curvature may be slightly shorter than the ablated cornea such that the covering can be steeper than the cornea prior to placement on the cornea. The covering 100 comprises a first configuration 100C1 prior to placement on the cornea.

The base radius R1 can be sized to the cornea in many ways. For example, base radius R1 may have a radius corresponding to the outer unablated portion of the cornea. Alternatively or in combination, the base radius R1 may have a radius corresponding to the post ablated eye.

The covering 100 may comprise a modulus within a range from about 4 MPa to about 20 MPa, such that central portion can conform at least partially to the ablated stroma and so that the covering can smooth corneal irregularities and stromal irregularities of the ablated cornea. The covering may comprise an elastomeric stretchable material such that the covering can stretch to fit the cornea, for example. The covering having the modulus within a range from about 4 MPa to about 20 MPa can be formed in many ways as described herein. For example, the covering may comprise a single piece of material having a substantially uniform thickness extending across the ablated cornea and at least a portion of the unablated cornea, and the single piece of material may comprise an elastic material such as a silicone elastomer or a hydrogel. Alternatively, the covering may comprise a single piece of material having a non-uniform thickness extending across the ablated cornea and at least a portion of the unablated cornea. The covering can be shaped in many ways and may comprise a single piece of one material, or may comprise a single piece composed to two similar materials, or may comprise a plurality of materials joined together.

The covering 100 may comprise one or more outer portions extending outside the inner central portion, and these outer portions may seal the cornea when the inner portion conforms at least partially to the ablated stroma. For example, the covering 100 may comprise outer portion additional shapes disposed outward from a central portion as described herein. For example, the covering may comprise a bicurve having a second radius of curvature disposed peripheral to the inner radius R1 of curvature to fit the unablated portion of the cornea. For example, the second and outer radius of curvature may comprise a shorter radius of curvature when the central portion is treated for myopia. The covering may comprise a third radius of curvature longer than the second radius of curvature so as to fit the sclera under the conjunctiva. The covering may comprise an oblate shape to fit the ablated and non-ablated portions of the cornea, and the covering may extend over the sclera with an outer portion, for example.

FIG. 1B2 shows the covering as in FIG. 1B1 conforming to ablated stromal tissue and smoothing the epithelium over the ablated stroma. The cornea comprises an ablated surface 20 to correct vision that may have a corresponding radius of curvature, for example radius R2. The ablated profile 20 may comprise additional, alternative, or combinational shapes with those corresponding to radius R2, such as aberrations ablated into the cornea to correct aberrations of the eye and astigmatism ablated into the cornea, and the inner portion 110 of covering 100 can conform to these ablated profiles of the cornea such that the patient can receive the benefit of the ablative vision correction when the covering is positioned on the cornea. For example, the cornea ablation profile 20 may correspond to radius of curvature R2, and the inner portion 110 can flatten from configuration 100C1 corresponding to radius of curvature R1 prior to placement to a second configuration 100C2 corresponding substantially to the ablated profile 20, such the patient can see with the benefit of ablation profile 20. For example, the second configuration 100C2 can comprise a conforming radius of curvature R12 that corresponds substantially to radius of curvature R2. The profile corresponding to the first configuration 100C1 of the covering 100 is shown positioned over cornea 10 to illustrate the change in profile of the covering from configuration 100C1 prior to placement to conforming second configuration 100C2 of the covering 100 when positioned on the cornea.

The conformable covering 100 comprises sufficient rigidity so as to smooth the epithelium when covering 100 is positioned on the cornea over the ablation profile 20. The epithelium comprises a peripheral thickness 12T that may correspond substantially to a thickness of the epithelium prior to debridement of the epithelium to ablate the cornea. The epithelium also comprises regenerating epithelium 12R disposed over the ablation profile 20. The covering 100 can smooth the epithelium 12R when conforming to the cornea in the second configuration 100C2. For example, irregularities 12I of the regenerating epithelium 12R disposed over the ablation can be smoothed when the epithelium regenerates along the inner portion of covering 100, such that the irregularities 12I of the regenerating epithelium 12R are thinner than the thickness 12T of the peripheral epithelium.

Work in relation to the embodiments as described herein indicates that an at least partially conformable covering having a modulus within a range from about 4 MPa to about 20 MPa can conform at least partially to the ablated stroma and smooth irregularities of the epithelium and stroma so as to improve vision as described herein. The covering having the modulus within the range from about 4 MPa to about 20 MPa can be formed in many ways as described herein.

The conformable covering 100 may comprise a perimeter 120P with rigidity sufficient to indent the epithelium along at least a portion of the perimeter so as to seal the cornea with seal 100S. The portion 12C of the epithelium 12 can extend over the perimeter 120P of the covering 100.

FIG. 1B2A shows a covering as in FIG. 1B2 forming an indentation 12IT in the epithelium such that the epithelium 12 extends over at least a portion of the perimeter 120P of the covering. The covering forms indentation 12IT in the epithelium such that the epithelium comprises an indentation thickness 12T that is less than an outer thickness of the epithelium 12. The indentation of the epithelium with the covering can help to seal the cornea with the perimeter.

FIG. 1B2B shows a covering as in FIG. 1B2 forming indentation 12IT in the epithelium. The covering forms indentation 12IT in the epithelium such that the epithelium comprises an indentation thickness 12T that is less than an outer thickness of the epithelium 12T. The indentation of the epithelium with the covering can help to seal the cornea with the perimeter.

Work in relation to embodiments described herein suggests the indentation of the covering can vary radially around the eye of the patient, in accordance with orientation of the covering on the eye when the covering comprises a substantially constant rigidity of the outer portion, for example a substantially constant rigidity around the perimeter. The inferior portion of the covering may comprise a greater amount of epithelial covering over the perimeter than the superior portion of the covering. For example, FIG. 1B2A may correspond to a first portion of covering 100 at an inferior location of the cornea and FIG. 1B2B may correspond to a second portion of the covering at a superior location of the cornea. Work in relation to embodiments also suggests that there may be variability in covering of the perimeter with the epithelium between the nasal portion of the perimeter, and the temporal portion of the perimeter, although both the nasal and temporal locations can comprise covering intermediate and between the more extensive covering of the inferior portion and the less extensive covering of the superior portion of the perimeter.

FIG. 1B2C shows a covering abutting the cornea to seal the cornea without forming a substantial indentation in the epithelium. The covering may comprise a chamfer to contact and seal the cornea. The rigidity of the outer portion can be determined based on the thickness of the outer portion of the covering, hardness of the material, and chamfer angle so as to contact the epithelium to seal the cornea without substantial deformation of the epithelium.

The covering may comprise a non-uniform rigidity around the outer portion of the covering comprising the perimeter. For example, the covering may comprise a superior portion corresponding to a superior location on the cornea and an inferior portion corresponding to an inferior location on the cornea. The superior portion may comprise a rigidity less than the inferior portion. For example, the superior portion may comprise the rigidity less than the inferior portion, such that deformation of the epithelium is inhibited when the perimeter abuts the cornea is sealed. Alternatively, the superior portion may comprise the rigidity less than the inferior portion such the deformation of the epithelium with the covering comprises a substantially constant amount around the perimeter, for example a deformation of no more than about 10 um, for example 5 um.

FIG. 1C shows a therapeutic covering as in FIG. 1-2A comprising a covering molded with a homogeneous material, in which the outer portion comprises a thickness configured to conform with the cornea and in which the inner portion 110 comprises thickness configured to smooth the epithelium and conform to the ablated profile 20. The outer portion 120 may comprise a thickness of no more than about 100 microns. For example, the outer portion 120 may comprise a thickness of about 50 microns at the boundary with the inner portion 110, and linearly taper from 50 microns at the boundary with the inner portion to about 20 microns at the periphery of the outer portion 120. The inner portion 110 may comprise a thickness of no more than about 250 microns, for example no more than about 200 microns. For example, the inner portion may comprise a thickness of about 100 microns. For example, the thickness of each of the inner portion and the outer portion may comprise no more than about 50 microns so as to provide substantial oxygen transport and epithelial regeneration. Many materials can be used as described herein, and the covering may comprise one or more materials. For example, the covering may comprise a single piece of material such as silicone having a water content within a range from about 0.1% to about 10%, for example no more than about 1%, and a hardness Shore A durometer parameter within a range from about 5 to about 90, for example within a range from about 40 to about 85.

FIG. 1C1 shows a covering 100 having an inner portion 110 comprising an inner thickness and an inner material 110M and an outer portion 120 comprising an outer thickness and an outer material 120M, in which the inner thickness is greater than the outer thickness. The inner material 110M may comprise many materials and may comprise an optically clear silicone, for example silicone with resin. The inner material may comprise silicone positioned in a mold with the outer portion 120 formed around the inner portion. The inner portion may comprise a hardness similar to the outer portion. The outer material 120M of the outer portion 120 may comprise a material similar to the inner portion. For example, the outer material 120M may comprise silicone and the inner material 110M may comprise silicone. This use of similar materials on the inner and outer portions can improve adhesion of the inner portion to the outer portion. The outer material 120M may extend along the inner portion 110, for example along the underside of the inner portion 110, such that the inner material 110M is held in a pocket of the outer material 120M. Alternatively, the inner material 110M may extend substantially across the thickness of the inner portion 110, such that the outer material 120M comprises a substantially annular shape with the inner material 110M comprising a disc shaped portion disposed within the annulus and extending substantially from the upper surface coating to the lower surface coating when present.

FIG. 1C1A shows a covering as in FIG. 1C1 adhered to the cornea with a smooth upper surface, and a lower surface conforming to irregularity of the cornea, for example an irregularity comprising a central island 10CI of the ablated stroma. The central island 10CI may comprise an outward protrusion in the ablated profile of the stroma at least about 1 micron outward and about 2.5 mm across, for example. The upper surface may comprise a substantially rigid material for vision correction, and the lower surface may comprise a soft material so as to deflect to irregularities of the cornea when the upper surface provides optical correction. For example, the lower surface may comprise an indentation 110I when positioned on the irregularity of the cornea. Although the lower surface comprising the soft material can deflect to correspond to the ablation profile 20, the upper surface comprising the rigid material may comprise a predetermined curvature selected by a health care provider so as to fit the ablation profile and correspond to the refractive correction of the patient so as to provide vision correction.

FIG. 1C2 shows a covering as in FIGS. 1-2A to 1B2 having inner portion 110 comprising an inner thickness and inner material 110M and outer portion 120 comprising an outer thickness and outer material 120M, in which the inner thickness can be greater than the outer thickness and the outer material 120M extends around the inner material 110M. The covering 100 may comprise at least a bicurve covering having at least a second radius R1B. The inner portion 110M may comprise three layers of material, a first layer 100L1 of a first material 110M1, a second layer 100L2 of a second material 110M2 and a third layer 100L3 of a third material 110M3. The second material 110M2 may comprise a rigid material, for example one or more of a rigid gas permeable material, a rigid silicone, or a rigid silicon acrylate. The first material 110M1 and the third material 110M3 may comprise a soft material, for example a soft elastomer or soft hydrogel such as one or more of a soft optically clear silicone or a soft silicone hydrogel. The first material, the third material, and the outer material 120M may comprise materials similar materials, such that the second layer of rigid material 110M2 is encapsulated with the first soft material 110M1, the third soft material 110M3 and on the perimeter with the soft outer material 120M. In many embodiments, the second rigid material 110M2 comprises a material similar to each of the first material 110M1, the third material 110M3 and the outer material 120M, for example each may comprise silicone, such that the corresponding portions of the covering 100 can be bonded together with the silicone similar to silicone elastomer material, for example. In many embodiments, the covering 100 can be formed in a mold with rigid second material 110M2 placed in the mold and encapsulated within a single piece of material comprising first material 110M1, third material 110M3 and outer material 120M, such that first material 110M1, third material 110M3 and outer material 120M comprise substantially the same material, for example silicone elastomer. The rigid second material 110M2 may comprise silicone bonded to each of first material 110M1, third material 110M3 and the outer material 120M, for example with curing such that first material 110M1, third material 110M3 and outer material 120M comprise the same soft silicone material bonded to the second material 110M2 comprising rigid silicone.

The soft material comprising soft outer portion 120 composed of soft material 120M, first layer 100L1 composed of soft material 110M1 and third layer 100L3 composed of soft material 120M3 can provide improved comfort and healing for the patient. The soft material can deflect, bend or indent so as to conform at least partially to the tissue of the eye when the rigid portion comprising rigid material 110M2 corrects vision of the patient. The dimension 102 across inner portion 110 can be sized to substantially cover the ablation zone and slightly smaller than the ablation dimensions, such as ablation diameter 20D, so that the epithelium can grow inward and contact the layer 100L1110L1 of soft first material 110M1 without substantial disruption from the rigid material 120M2 when the inner portion 110M corrects vision with the layer of rigid material 110M2. The eyelid can also move over the third layer 100L3 for improved comfort. The soft first material 110M1 and soft third material 110M3 may comprise soft elastomer or soft hydrogel, for example, and may each comprise the same material so as to encapsulate the second layer 100L2 of rigid second material 110M2.

The soft material comprising soft outer portion 120 composed of soft material 120M, first layer 100L1 composed of soft material 110M1 and third layer 100L3 composed of soft material 110M3 can have a modulus within a range from about 1 to 20 MPa, for example within a range from about 1 to 5 MPa.

The material inner material 120M and 110M2 of second layer 100L2 can have a modulus within a range from about 5 to about 35 or more, for example as set forth in Table A below. For example, when material 120M comprises silicone elastomer or layer 100L2 of material 110M2 comprises silicone elastomer, the modulus can be within a range from about 5 to about 35 MPa, for example within a range from about 20 to about 35 MPa.

The layers of covering 100 can comprise dimensions so as to provide therapeutic benefit when placed on eye 2. The thickness of layer 100L1 can be from about 5 um to about 50 um, for example, within a range from about 10-30 um, such that the layer 100L1 can provide a soft at least partially conformable material to receive the lens. The middle layer 100L2 can be from about 20 um to about 150 um, for example, and material 110M2 can have a modulus greater than first material 110M1 of first layer 100L1, so as to deflect the epithelium of the eye when the middle layer is deflected. The third layer 100L3 can be within a range from about 5 um to 50 um, for example within a range from about 10 um to about 30 um, and can cover second layer 100L2 so as to retain the second layer in the inner portion 110 of the covering 100.

FIG. 1C2A shows a covering as in FIG. 1C1 placed on the cornea with a smooth upper surface and a lower surface conforming to irregularity of the cornea near the edge of the ablation. As the epithelium can be about 50 um thick, in many embodiments the dimension 102 is sized so as to cover substantially the ablated cornea for vision correction and smaller than the ablation zone, such that the outer portion 120 can conform at least partially to the epithelium. The outer portion 120 may extend to the sclera, and comprise a tri-curve covering 100 as described herein, with the inner portion 110 having first layer 100L1 of first material 110M1, second layer 100L2 of second material 110M2, and third layer 100L3 of third material 110M3.

FIG. 1C2A1 shows a covering having a layer of hydrogel material on a posterior surface of the covering. The covering 100 may comprise a wettable surface coating 134 disposed on at least the upper side of the covering as described herein. The layer of hydrogel material may comprise an inner portion of the layer of hydrogel material 110MHG and an outer portion of the layer of hydrogel material 120MHG. The layer of hydrogel material extends to the fenestration so as to couple the hydrogel material to the fenestration. The hydrogel material can be coupled to the fenestration in many ways. For example, the layer of hydrogel material may cover the fenestration, or the fenestration 100F may extend through the hydrogel material. The fenestration 100F extending through the layer of hydrogel material can encourage pumping of the tear liquid as described herein. Alternatively or in combination, the layer of hydrogel material covering a posterior surface of the fenestration 100F to couple the fenestration 100F to the hydrogel layer may encourage movement of a therapeutic agent along the hydrogel layer toward a central portion of the cornea for example. The hydrogel may extend along a deflectable portion of the covering so as to exert at least some pressure on the hydrogel layer to encourage movement of one or more of tear liquid or the therapeutic agent along the hydrogel layer when the patient blinks, for example.

The hydrogel layer as described herein may encourage regeneration of the epithelium and may provide a soft surface to contact the epithelium regenerating over the ablation so as to encourage epithelial regeneration under the optical component as described herein, and the optical component can resist deformation so as to protect the epithelium and provide an environment to encourage regeneration of the epithelium.

The hydrogel material may comprise one or more of the hydrogel materials as described herein. The hydrogel material extending along the lower surface can increase comfort of the covering when placed on the eye. The hydrogel material may comprise a substantially uniform thickness within a range from about 1 um to about 100 um, for example from about 2 um to about 50 um and in many embodiments within a range from about 5 um to about 20 um. The hydrogel material extending along the posterior surface may comprise on or more of the hydrogel materials as described herein combined with one or more of materials 110M, 110M1, 110M2, 110M3 or 120M as described herein. For example the one or more of materials 110M, 110M1, 110M2, 110M3 or 120M may comprise silicone such as silicone elastomer comprising siloxane, and the hydrogel may comprise a hydrogel such as silicone hydrogel material as described herein.

FIG. 1C2A shows a covering having a layer of hydrogel material on a posterior surface of the covering. The covering 100 may comprise a wettable surface coating 134 disposed on at least the upper side of the covering as described herein. The layer of hydrogel material may comprise an inner portion of the layer of hydrogel material 110MHG and an outer portion of the layer of hydrogel material 120MHG. The layer of hydrogel material extends to the fenestration so as to couple the hydrogel material to the fenestration. The hydrogel material can be coupled to the fenestration in many ways. For example, the layer of hydrogel material may cover the fenestration, or the fenestration 100F may extend through the hydrogel material. The fenestration 100F extending through the layer of hydrogel material can encourage pumping of the tear liquid as described herein. Alternatively or in combination, the layer of hydrogel material covering a posterior surface of the fenestration 100F to couple the fenestration 100F to the hydrogel layer may encourage movement of a therapeutic agent along the hydrogel layer toward a central portion of the cornea for example. The hydrogel may extend along a deflectable portion of the covering so as to exert at least some pressure on the hydrogel layer to encourage movement of one or more of tear liquid or the therapeutic agent along the hydrogel layer when the patient blinks, for example.

The hydrogel layer as described herein may encourage regeneration of the epithelium and may provide a soft surface to contact the epithelium regenerating over the ablation so as to encourage epithelial regeneration under the optical component as described herein, and the optical component can resist deformation so as to protect the epithelium and provide an environment to encourage regeneration of the epithelium.

The hydrogel material may comprise one or more of the hydrogel materials as described herein. The hydrogel material extending along the lower surface can increase comfort of the covering when placed on the eye. The hydrogel material may comprise a substantially uniform thickness within a range from about 1 um to about 100 um, for example from about 2 um to about 50 um and in many embodiments within a range from about 5 um to about 20 um. The hydrogel material extending along the posterior surface may comprise on or more of the hydrogel materials as described herein combined with one or more of materials 110M, 110M1, 110M2, 110M3 or 120M as described herein. For example the one or more of materials 110M, 110M1, 110M2, 110M3 or 120M may comprise silicone such as silicone elastomer comprising siloxane, and the hydrogel may comprise a hydrogel such as silicone hydrogel material as described herein.

FIG. 1C2B shows a covering having a layer of hydrogel material on a posterior surface of the covering extending less than a maximum distance across the covering such that end portions of the covering are configured to engage the epithelium of the eye away from the hydrogel layer and inhibit movement of the covering when placed on the eye. In many embodiments, the material 120M can couple to the surface of the eye, for example the epithelium so as to inhibit movement of the covering. The material 120M may comprise a sticky tacky hydrophobic material such as silicone to engage the epithelium to inhibit movement, and the material 120M may be coated with one or more coatings as described herein, for example with vapor deposition. The hydrogel material can be coupled to the fenestration in many ways. For example, the layer of hydrogel material may cover the fenestration, or the fenestration 100F may extend through the hydrogel material.

FIG. 1C2C shows a covering 100 having an annular layer of hydrogel material 120MHG on a posterior surface of the covering such that an inner portion of the covering contacts the cornea away from the hydrogel layer and an outer portion of the covering contacts the cornea away from the covering when placed on the eye. Work in relation to embodiments suggests that the annular hydrogel layer can provide an environment to encourage growth of the epithelium along the posterior surface of inner material 110M1 as described herein, and the lower surface of material 110M1 can be coated with a material having a thickness less than the hydrogel, for example.

FIG. 1C3 shows a shows a covering having a tricurve profile to fit sclera with slopes of the curved profiles aligned so as to inhibit ridges at the boundaries of the curved portions as in FIG. 1B2 and having a layer of hydrogel material 120MHG on a lower surface. The hydrogel material 120M may extend substantially across the posterior surface of the covering. The covering may extend along the lower surface a distance less than a distance across the covering so as to provide a portion of the covering without the hydrogel to engage the eye, for example the epithelium of the eye that may comprise one or more of the corneal epithelium or the conjunctival epithelium. Alternatively, the covering may extend substantially along the posterior surface of the covering corresponding to the distance across the covering so as to provide the hydrogel covering over the outer portion of the covering that engages the eye.

Figure 4:
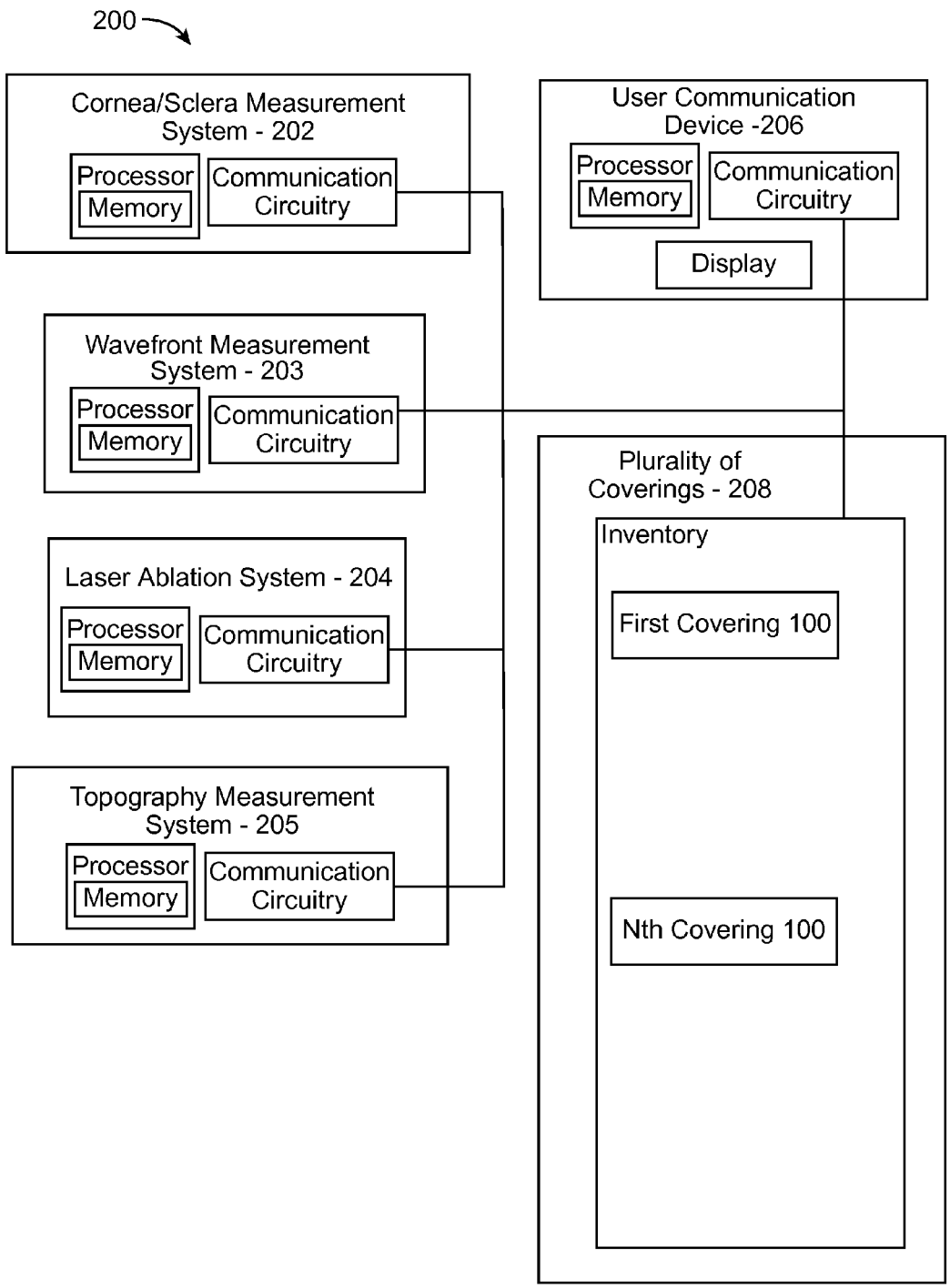

FIG. 1C4 shows a plan view covering having a tricurve profile to fit the cornea, limbus and sclera with slopes of the curved profiles aligned so as to inhibit ridges at the boundaries of the curved portions and having a hydrogel material on a lower surface extending less than a maximum distance across the covering to engage the conjunctiva with the covering away from the hydrogel material. Alternatively, the covering may extend substantially along the posterior surface of the covering corresponding to the distance across the covering so as to provide the hydrogel covering over the outer portion of the covering that engages the eye. The hydrogel covering may comprise an annular shape extending along the lower surface as described herein.

Figure 1D:
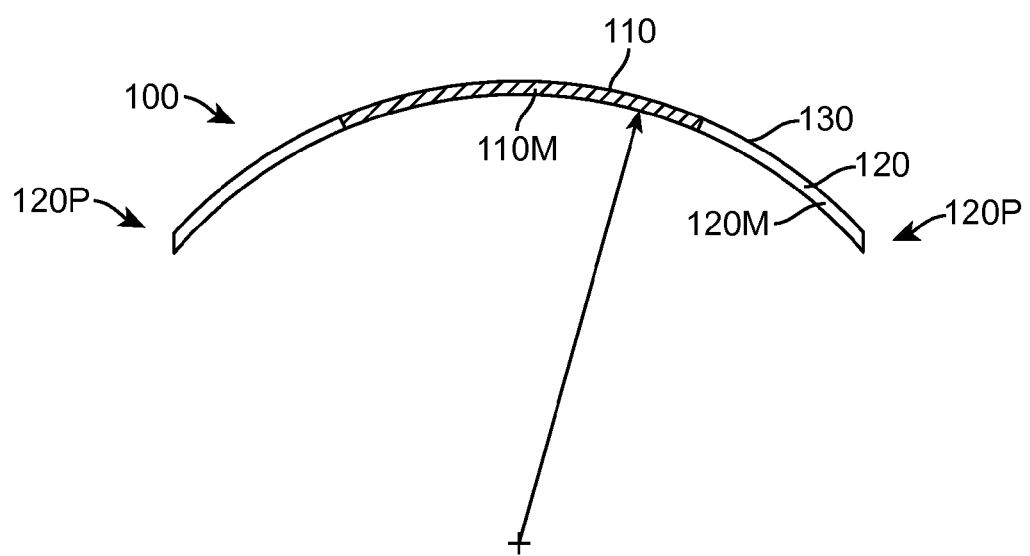
FIG. 1D shows a covering as in FIGS. 1-2A to 1B2 having an inner portion comprising an inner thickness and an inner material and an outer portion comprising an outer thickness and an outer material, in which the inner thickness is substantially similar to the outer thickness, in accordance with embodiments of the present invention.

FIG. 105 shows a fenestration 100F having a posterior end 100FPE covered with a layer of hydrogel material 29MHG extending along the posterior surface of the covering 100, in accordance with embodiments of the present invention;

FIG. 106 shows a fenestration 100F extending through a layer of hydrogel material 120MHG extending along the posterior surface of the covering 100, in accordance with embodiments of the present invention;

FIG. 1D shows a therapeutic covering 100 comprising a first inner material 110M and a second outer material 120M, in which the outer portion 120 comprises a hardness configured to conform with epithelium of the cornea and in which the inner portion 110 comprises second hardness configured to smooth the epithelium and conform to the ablated profile 20. The outer material 120M may comprise many materials as herein. The Shore A hardness of each of the inner portion and the outer portion can be within a range from about 5 to about 90. For example, the outer material 120M may comprise silicone having a hardness Shore A durometer parameter from about 20 to about 50, for example from about 20 to about 40, and the inner material 110M may comprise silicone having a hardness durometer parameter from about 40 to about 90, for example from about 50 to about 90. The outer portion comprises a perimeter 120P, and the perimeter may comprise a peripheral and circumferential edge structure to abut the epithelium to form the seal with the epithelium, for example when the base radius of the covering is less than the cornea. The peripheral and circumferential edge structure can be shaped in many ways to define an edge extending around the perimeter to abut the epithelium, for example with one or more of a taper of the edge portion extending to the perimeter, a bevel of the edge portion extending to the perimeter or a chamfer of the edge portion extending to the perimeter. The inner portion 110 may comprise inner thickness and inner material 110M and the outer portion 120 may comprise an outer thickness and outer material 120M, in which the inner thickness is substantially similar to the outer thickness.

The peripheral edge structure to abut the epithelium can be used with many configurations of the inner portion as described herein. For example, the inner portion may comprise an RGP lens material having a lower rigid surface to contact and smooth the cornea and an upper rigid optical surface. Alternatively, the inner portion may conform to the cornea as described herein. The outer portion may comprise a skirt, and the skirt may comprise the peripheral edge structure to abut and seal the cornea, such as the chamfer. The rigidity of the outer portion comprising the edge structure can be determined to seal the cornea with one or more of hardness and thickness, as described herein.

Figure 1E:
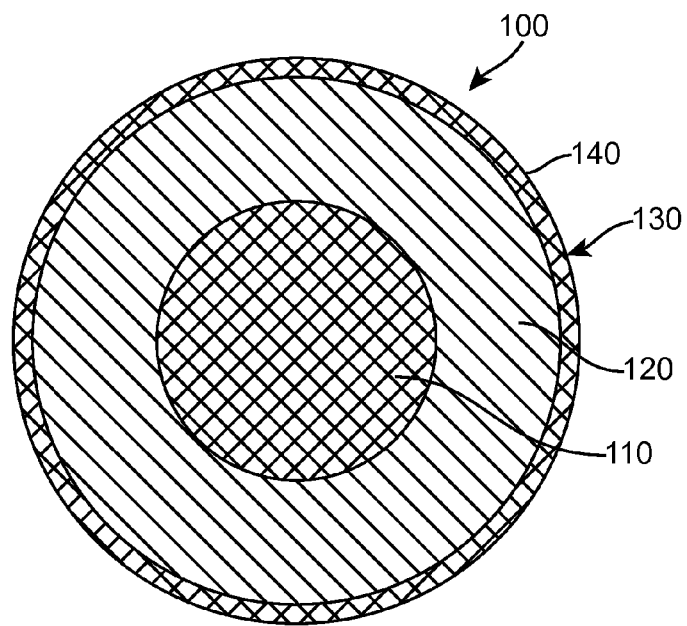
FIGS. 1E and 1F show top and side views, respectively, of a covering comprising an inner portion and an outer portion, as in FIGS. 1A to 1B2 and a peripheral rim portion disposed around the outer portion, in accordance with embodiments of the present invention.
Figure 1F:
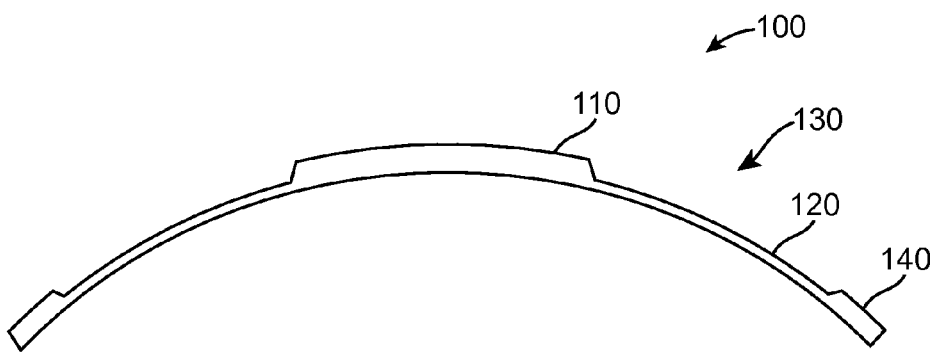

FIGS. 1E and 1F show top and side views, respectively, of covering 100 comprising inner portion 110, outer portion 120, and a peripheral rim portion 140 disposed around outer portion 120. The peripheral portion 140 can be more rigid than outer portion 120. Work in relation to embodiments suggests that in some instances the lower sticky, tacky surface of outer portion 120 can stick to itself during deployment onto the eye, and the peripheral portion 140 can improve handling when the covering is placed on the eye. The covering may comprise a single piece of material or may comprise multiple pieces adhered together, for example molded together. For example, the covering may comprise an inner thickness of inner portion 110 and an outer thickness of outer portion 120, in which the inner thickness is greater than the outer thickness. The peripheral portion 140 may comprise a thickness, and the thickness of the peripheral portion 140 can be greater than the thickness of outer portion 120 such that the peripheral portion 140 is more rigid than the outer portion 120. The thickness of the inner portion 110 and the thickness of the peripheral portion 140 can be substantially similar, and these portions may comprise substantially the same thickness and rigidity.

FIG. 1G shows covering 100 comprising inner portion 110 and outer portion 120, such that outer portion 120 comprises a taper 120T of thickness 108 extending between the perimeter of the inner portion 110 and the perimeter of the outer portion 120. The taper may comprise a substantially linear change in thickness 108 extending between the perimeter of the inner portion and the perimeter of the outer portion.

FIG. 1G1 shows a covering 100 comprising inner portion 110 and an outer portion 120 comprising the taper as in FIG. 1G, and an outer rim or flange 120F of substantially uniform thickness peripheral to the taper 120T. The outer taper may extend from the dimension across 102 of the inner portion 110 to the dimension across 154A that is less than the dimension across 104 of the outer portion. The rim of substantially uniform thickness may comprise an annular shape having a thickness within a range from about 10 um thick to about 40 um thick, and may comprise a width 154B within a range from about 0.05 to about 0.8 mm, for example about 0.5 mm. The rim, for example flange 120F, may comprise a thickness of no more than about 50 um, such that the flange comprises a thickness no more than the epithelium.

The covering 100 can be dimensioned in many ways. The total diameter across can be from about 6 mm to about 12 mm, for example about 10 mm. The inner portion may comprise a diameter within a range from about 4 mm to 8 mm, for example about 6 mm. The annular rim comprising flange 120F can extend around the perimeter of the covering with a thickness of about within a range from about 5 um to about 50 um, for example about 35 um. The annular rim comprising flange 120F may comprise an inner diameter of within a range from about 5 mm to about 11 mm, for example about 9 mm and an outer diameter within a range from about 6 mm to about 12 mm, for example about 10 mm and corresponding to the perimeter of the covering. The annular rim may comprise a width of within a range from about 0.1 mm to about 1 mm, for example 0.5 mm, extending circumferentially around the covering. The outer portion 120 may comprise the rim with flange 120F and a taper 120T that extended from inner portion 110 to the rim comprising perimeter 120P. The taper in thickness can be substantially uniform between the outer diameter of the inner portion and the inner diameter of the rim, and the boundaries of the taper can be rounded and smoothed near the inner portion and the rim. The central portion may comprise a substantially uniform thickness within a range from about 50 um to about 150 um, for example about 50 um. The base radius of curvature of the lower surface of the covering can be within a range from about 7 mm to about 8 mm. The lower surface may comprise an aspheric surface or a bicurve surface and combinations thereof. The upper surface of the covering can comprise a radius of curvature along the inner portion within about 0.1 mm curvature of the lower surface, such that the covering is substantially uniform with no substantial refractive power, for example refractive power within about +/−1D.

FIGS. 1G1A to 1G1H show a covering as in FIG. 1G1 and dimensions suitable for use in accordance with embodiments as described herein such as with experiments, clinical studies and patient treatment. FIG. 1G1A shows an isometric view of covering 100 having the inner portion 110, the outer portion 120, the taper 120T and rim comprising flange 120F. FIG. 1G1B shows a bottom view of covering 100. FIG. 1G1C shows a side view of the covering 100. FIG. 1G1D shows a top view of the covering 100. FIG. 1G1E shows a side cross sectional view of covering 100 along section D-D. FIG. 1G1F shows detail C of cross-section D-D, including the radius of curvature R1 of the lower surface of the inner portion 110, and the upper radius of curvature Rupper of the inner portion 110. The upper radius of curvature Rupper may correspond substantially to the lower radius of curvature R1 prior to placement on the eye, for example to within about +/−1D of optical power, such that the inner portion 110 prior to placement may comprise no substantial optical power. Detail C shows a side cross sectional view of covering 100 of the inner portion. FIG. 1G1G shows detail B of cross-section D-D. Detail B shows a side cross sectional view of the rim comprising flange 120F. The flange 120F has a thickness 109. Flange 120F may comprise a taper extending along a width 102FW, for example from a first thickness 109A of about 35 um to second thickness 109B of about 25 um extending along width 120FW near the chamfer. Flange 120F comprises a chamfered edge 120FE to contact the cornea or conjunctiva along perimeter 120P of the covering.

FIG. 1H1 shows spatial frequency and elevation smoothing of an epithelial irregularity 12I transferred to a front surface 110U of covering 100 as in FIG. 1-2A. The regenerating epithelium 12R comprises an irregularity 12I. The covering 100 conforms substantially to the shape ablated in the stroma when positioned on the eye as noted above. The covering 100 comprises a rigidity so as to conform substantially to the ablation profile 20 over about at least about 3 to 4 mm of the ablated stroma such that the patient can see and receive optical correction with the ablated surface. The regenerating epithelium comprises a thickness profile 12RP that includes irregularity 12I. The conformable covering comprises a thickness profile of thickness 106 that encompasses a deformation thickness over the irregularity 106D. The thickness of the covering can vary over the epithelium to smooth the irregularity transmitted to the front surface of the covering so as to improve patient vision consistent with the ablation profile 20 when the covering conforms to the ablation profile 20. For example thickness 106D over the irregularity can be less than thickness 106 away from the irregularity. The irregularity may comprise an indentation and the covering may be thinner over the indentation. The silicone elastomer and hydrogel materials as described can be at least somewhat compressible so as to conform at least partially to the cornea and form an indentation so as to receive a portion of the cornea comprising one or more of epithelium or ablated stroma and decrease aberrations.

Experimental studies of optical coherence tomography (hereinafter "OCT") images and Pentacam™ images and topography images, noted below, indicate that the thickness of the inner portion of the covering 100 can vary so as to decrease optical aberrations along the upper surface when the covering is adhered to the cornea. This variation in thickness can be related to one or more of stretching of the covering over the irregularity or compression of the covering over the irregularity.

The irregularities of the epithelium generally comprise spatial frequencies that are greater than the spatial frequencies of the vision correcting portion of the ablation. The covering can provide spatial filtering of the frequencies of the underlying surface so as to inhibit relatively higher spatial frequencies of epithelial irregularities and pass relatively lower spatial frequencies corresponding to vision correction, such as lower spatial frequencies corresponding to sphere and cylinder. The spatial frequencies ablation profile 20 that are useful to correction vision can be lower than the spatial frequencies of the irregularities, and the spatial dimensions of the vision correction greater than the dimensions of the irregularities. For example, the spatial frequencies of the vision correction can correspond to periods of oscillation less than the periods of oscillation of the irregularities.

FIG. 1H2 shows spatial frequency and elevation smoothing of the epithelial irregularity with a plot of relative height relative for the upper surface of the covering and the upper surface of the irregularity. The irregularity of the regenerating epithelium 12R may comprise a profile height 12RPH and profile width 12RPW. The upper surface of the covering may comprise a profile 110UP. The irregularity of the upper surface corresponding comprises a width 110UPW and a height 110UPH. Height 110UPH is less than height 12RPH so as to correspond to smoothing of the irregularity. Width 110UPW is greater than width 12RPW so as to correspond to smoothing of the irregularity. Profile 110UP of the upper surface of the covering corresponds to lower frequencies than profile 12RP, such that the covering comprise a low pass spatial frequency filter. This can be seen with the Pentacam™ and topography data shown below in conjunction with OCT images showing that the covering and cornea conform without a substantially gap disposed therebetween. Alternatively or in combination, the covering can smooth the cornea when a gap is present, for example when a portion of the cornea is smoothed with contact to the covering and the gap provides an environment for the epithelium to grow smoothly over the ablation.

Based on the teachings described herein, a person of ordinary skill in the art can conduct studies to determine empirically the rigidity of the inner portion so as to pass substantially vision correction spatial frequencies of the ablation to the upper surface of the covering and inhibit spatial frequencies of the irregularities of the ablated stroma and epithelium, for example with Pentacam™ and topography studies as described in the experimental section.

Work in relation to the embodiments as described herein indicates that a covering comprising a modulus within a range from about 4 MPa to about 20 MPa can provide smoothing with low pass spatial frequency filtering as described with reference to FIGS. 1H1 and 1H2. The covering may comprise an elastically stretchable material, for example an elastomer or a hydrogel, such that the lens can conform at least partially to the ablated stroma and exert at least some pressure on the ablated stroma and epithelium when at least partially conformed so as to smooth irregularities of the epithelium and irregularities of the stroma. The covering can comprise a thickness and a hardness so as to provide the spatial frequency filtering to improve vision in post-PRK patients with the modulus within the range from about 4 MPa to about 20 MPa. For example, the lens thickness can be increased to increase the modulus, decreased to decrease the modulus. The hardness of the material can be increased to increase the modulus and decreased to decrease the modulus. The modulus within the range from about 4 MPa to about 20 MPa can attenuate substantially higher spatial frequencies corresponding to irregularities of the epithelium and stroma so as to smooth the high spatial frequencies corresponding to the irregularities that can degrade vision, and can conform substantially to lower spatial frequencies that correspond to the vision correction so as to pass the lower spatial frequencies corresponding to vision correction so that the patient can experience an improvement in vision when the epithelium regenerates under the covering. For example, the high spatial frequencies may correspond to frequencies greater than about ⅙ (0.17) cycles per mm, and the low spatial frequencies may correspond to frequencies less than about ⅙ (0.17) cycles per mm. A person of ordinary skill in the art can determine the modulus and corresponding spatial frequencies to attenuate and pass, in accordance with the teachings as described herein. For example, the modulus of the covering can be measured with known methods and apparatus to measure the modulus of a contact lens, and measurements with Pentacam™ images as described herein can be used to determine the relationship of the modulus of the measured lens coverings to smooth irregularities, conformation of the lens coverings to the ablation, and vision.

FIG. 1I1 shows an inhibition of transfer of a corneal irregularity to a front surface of a covering, for example one or more of a stromal irregularity or an epithelial irregularity. The front surface of the covering comprises an optical surface for vision without substantially transfer of the irregularity to the front surface of the covering.

FIG. 1I2 shows elevation smoothing of the epithelial irregularity with a plot of height relative to a reference sphere for the upper surface of the covering and the upper surface of the irregularity. The plot shows a substantially spherical front surface of the covering, such that the transfer of the irregularity to the front surface is inhibited.

FIG. 1I3 shows a thickness profile of the covering as in FIG. 1I2 so as to smooth irregularities transferred to the front surface of the covering. The thickness profile can vary in response to the underlying surface, for example with a decrease in thickness corresponding to an elevation in the surface profile of the cornea.

FIG. 1J1 shows covering 100 having a bicurve profile to fit an ablated cornea. The bicurve profile may comprise an inner portion having a lower surface comprising a radius of curvature R1 and an outer portion having a radius of curvature R1B. The inner portion may comprise a radius selected to fit approximately the post-ablated cornea, for example to within about +/−2D. The outer portion may comprise the radius of curvature R1B sized to correspond to the outer unablated cornea, for example to within about +/−2D. The covering may comprise an elastic material with a modulus within a range from about 4 MPa to about 20 MPa, such that the covering can conform at least partially to the cornea and smooth irregularities of the cornea as described herein. R1 can be longer than R1B, for example with PRK ablation to treat myopia. R1 can be shorter than R2, for example with PRK ablation to threat hyperopia.

FIG. 1J2 shows covering 100 having an oblate profile to fit an ablated cornea, for example a cornea ablated for myopia. The covering may comprise an apical radius of curvature corresponding to R1 near a center of the covering, and a peripheral radius of curvature, based on the conic constant of the oblate profile of the lower surface of covering 100. Alternatively, the lower covering 100 may comprise a prolate ellipsoid shape to fit a PRK ablation to treat hyperopia.

FIG. 1J3 shows covering 100 having a tricurve profile to fit sclera and an ablated cornea. The tricurve covering may comprise an inner portion with an inner lower surface having radius of curvature R1 and an outer portion comprising an outer lower surface having radius of curvature R1B, as described above. The covering may comprise a third portion 130 disposed outside the outer portion and having a third radius of curvature R1C sized to fit the sclera and contact the conjunctiva disposed over the sclera. Work in relation to embodiments suggests that coupling to the sclera may improve alignment of the lens on the cornea.

The covering 100 having the tricurve profile may comprise dimensions sized to fit the cornea and sclera of the eye 2. The covering 100 having the tricurve profile may comprise an inner portion 110 and an outer portion 120 as described herein. The outer portion 120 may comprise the third scleral portion 130S having curvature R1C shaped to fit the sclera of the eye, for example shaped so as to contact the conjunctiva of the eye such that the conjunctiva is located between the sclera and the scleral portion 130S. The inner portion 110 may comprise a dimension 102 and the outer portion 120 may comprise a dimension 104 as described herein. The covering 100 may comprise a sag height 105 extending between an upper location of the inner portion 110 and the outer boundary of outer portion 120 shaped to fit the cornea. The third portion 130 may comprise a dimension across 103.

The dimension 102, the dimension 104 and the dimension 103 can be sized to the eye based on measurements of the eye. The dimension 103 may correspond to an annular region of the sclera extending from the limbus to the outer boundary of the third portion across a distance within a range from about 1 to 4 mm, for example within a range from about 1.5 to 2 mm. The size of the limbus of the eye can be measured so as to correspond to dimension 104, for example, and can be within a range from about 11 to 13 mm. The ablation zone can correspond to dimension 102, and dimension 102 corresponding to the rigid inner portion can be sized about 0.5 to about 2 mm less than the dimension across the ablation zone, such that the soft outer portion 120 contacts the eye near the edge of the ablation and the epithelial debridement.

The radius of curvature R1C of portion 130 can be determined so as to fit the eye, and can be within a range from about 12 mm+/−3 mm. The outer portion can be fit to within about +/−0.5 mm, for example to within about +/−0.25 mm.

The dimensions of the covering 100 can be determined in many ways, for example with topography measurements of the cornea and sclera. The corneal and scleral topography can be measured with many instruments, such as with the Orbscan™ topography system commercially available from Bausch and Lomb, and the Pentacam™ Scheimpflug camera system commercially available from Oculus. The ablation profile can be combined with the topography to determine the shape of the eye.

The dimensions of covering 100 can be sized to one or more of the cornea and sclera based on tolerances that may be determined clinically.

The outer portion 120 and the third portion 130 may comprise openings such as fenestrations as described herein, for example when the material comprises silicone.

The outer portion 120 and third portion 130 may comprise a hydrogel material, for example a silicone hydrogel material, and the inner portion 110 may comprise the rigid material 110M, for example second layer 100L2 and second material 110M2 between first layer 100L1 of first material 110M1 and third layer 100L3 of third material 110M3 as described herein.

As the tricurve covering may couple to the sclera so as to provide environment 100E to promote epithelial regeneration without substantially sealing the cornea, the outer portion 120 of the covering and the third portion 130 of the covering may comprise substantially water permeable material, for example when the inner portion 110 comprises the rigid material as described herein.

FIG. 1J4 shows covering 100 having a curved profile to fit sclera and an oblate profile to fit ablated cornea. The covering comprises the inner portion having the lower surface with the oblate profile having radius of curvature R1 comprising an apical radius of curvature and radius of curvature RO, and an outer portion comprising a lower surface having radius R1C to couple to the sclera as described herein. The apical radius of curvature may comprise a first radius of curvature and the radius of curvature R0 may comprise a second radius of curvature corresponding to a conic constant of the oblate profile.

The portions of the coverings as described herein, for example the inner portion and the outer portion, may comprise a junction wherein a first portion connects with a second portion, and the junction may have the modulus as described herein. The covering may comprise a contact lens having a central lens portion having a center stiffness of at least about 2 psi*mm2 coupled to an outer lenticular junction portion having a lenticular junction stiffness of at least about 5 psi*mm2.

FIG. 1J5 shows a covering 100 having the tricurve profile to fit sclera and the ablated cornea similar to FIG. 1J3. The modulus and thickness of the sclera contacting portion can be configured in many ways to fit many eyes with comfort and so as to resist movement of the inner portion 120. The modulus of sclera coupling portion 130 may be no more than about 5 MPa and the thickness no more than about 200 um so as to stretch substantially for comfort and resist movement of the inner portion when placed on the sclera.

The dimension 103 of sclera contacting portion 130 may correspond to an annular region of the sclera extending from the limbus to the outer boundary of the third portion across a distance within a range from about 1 to 4 mm, such that the dimension 103 can be from about 12 mm to about 16 mm, for example from about 14 mm to about 16 mm.

The radius of curvature R1C, thickness and modulus of the portion 130 can be configured so as to fit the eye to resist movement of inner portion 120 and with comfort. The radius of curvature R1C can be sized less than the radius of curvature of the sclera and conjunctiva. For example, the radius of curvature R1C can be no more than about 10 mm, for example no more than about 9 mm when the curvature of the scleral portion of the eye is at least about 12 mm for example. The third relative rigidity may comprise no more than about 4E-5 Pa*m^3 so as to stretch substantially for comfort and resist movement of the inner portion when the outer portion is placed on the sclera.

The thickness of the third portion having radius of curvature R1C can vary, for example from a thickness of about 200 um to a tapered edge.

FIG. 1J6 shows a tapered edge of the covering having a tricurve profile to fit sclera and an ablated cornea as in FIG. 1J5. The third portion 130 may comprise a flange 120F having a narrowing taper extending a distance 120FW to a chamfer 120FE. The chamfer 120FE can be defined along an outer rim where a first convexly curved lower surface joins a second convexly curved upper surface. The convex surfaces along the outer rim allow the covering to slide along the conjunctiva and the narrowing taper permits the third portion of the covering to stretch substantially and couple to the sclera and conjunctiva with decreased resistance for comfort.

The dimensions of the covering 100 can be determined in many ways, for example with topography measurements of the cornea and sclera. The corneal and scleral topography can be measured with many instruments, such as with the Orbscan™ topography system commercially available from Bausch and Lomb, and the Pentacam™ Scheimpflug camera system commercially available from Oculus. The ablation profile can be combined with the topography to determine the shape of the eye.

Figure 1K:
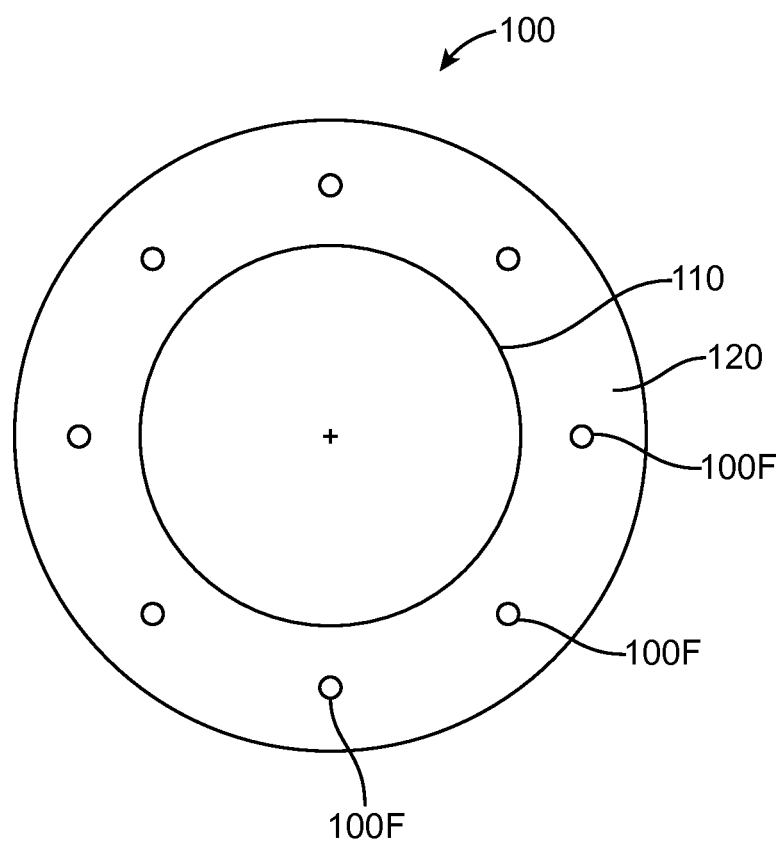
FIG. 1K shows a covering having fenestrations on an outer portion to pass a medicament when the cornea is sealed, in accordance with embodiments of the present invention.

FIG. 1K shows covering 100 having inner portion 110 and outer portion 120, and fenestrations 100F extending through the thickness of the covering on the outer portion so as to pass a medicament when the cornea is sealed. The medicament may comprise an anesthetic, an analgesic, or other medication, for example. The covering sealed to the cornea can inhibit the egress of the medicament toward the epithelial defect so that reepithelialization is not delayed. For example, an anesthetic such as proparacaine, lidocaine can be used to inhibit pain when the epithelium regenerates.

Figure 1L:
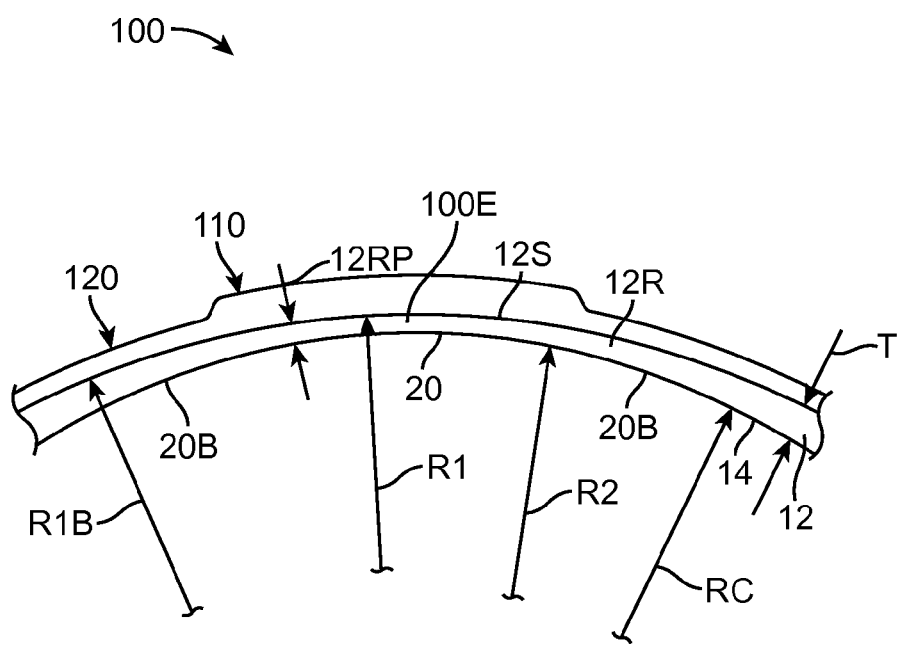
FIG. 1L shows fitting of a covering to a cornea, in accordance with embodiments of the present invention.

FIG. 1L shows fitting of a covering 100 to a cornea. The covering may comprise a base curvature, for example first radius of curvature R1 of inner portion 110 that may correspond to a radius of curvature when the covering comprises first configuration 100C1 prior to placement on the cornea. The covering may comprise a second radius of curvature R1B. The ablated cornea may comprise a second radius of curvature R2. The outer unablated portion of the curvature may comprise a corneal radius of curvature RC. The second radius of R2 of the outer portion 120 can be sized to fit the outer unablated portion of the cornea having radius of curvature RC, for example to within about +/−1D corresponding to within about +/−0.2 mm for RC of about 8 mm.

The first radius of curvature R1 can be greater than the ablated radius curvature R2 such that the curvature of the inner portion of the covering is less than the curvature of the cornea. As the curvature is inversely related to the radius of curvature, the inner portion 110 has a curvature less than the curvature of the ablation profile 20 of the cornea when the base radius of curvature R1 of the inner portion is greater than the radius of curvature R2 of the ablated cornea. The covering having substantially uniform thickness as described herein with the curvature less than the ablated cornea can correct visual aberrations that may be related to epithelial irregularity 12I, for example so as to correct temporary myopia related to irregularity 12I.

Work in relation to embodiments indicates that environment 100E to promote epithelial regeneration can be enhanced when the curvature of the inner portion 110 is less than the curvature of the ablated cornea corresponding to radius R2. The epithelium 12 may comprise a thickness T extending between an anterior surface of the epithelium and a posterior surface of the epithelium, and the thickness T can vary across the surface of the cornea. The base radius of curvature R1 sized greater than the radius of curvature R2 of the ablated profile 20 can define environment 100E with a concave meniscus profile such that pressure near the boundary of inner portion 110 is decreased to encourage epithelial migration inward as indicated by arrows 30 and pressure near a center of inner portion 110 is increased so as to inhibit formation of irregularity 12I and provide smooth regeneration of the epithelium. For example, the inner portion of the covering can have a curvature corresponding to about 1 to about 2.5 D less optical power than the ablated profile 20. This amount of lesser curvature of the covering can correct temporary myopia related to epithelial irregularity 12I and may also smooth the irregularity based on the deflection pressure as described herein, for example.

While the outer portion 120 can be fit in many ways, the outer portion 120 may comprise radius of curvature R1B corresponding to about 0 to 2D less optical power than the corresponding optical power of the unablated cornea having curvature RC. For example, the unablated portion of the cornea may have an optical power of about 43D, and the outer portion 120 may have a curvature R1B corresponding to about 41 to 43D, such that the covering is fit on the cornea with a fit ranging from matched to loose. Such fitting can be used with tri-curved coverings as described herein.

The tri-curve and oblate covering profiles as described herein can be sized similarly to the bicurve surface so as to provide inner portion 110 with a decreased curvature and increased radius of curvature relative to ablation profile 20 so as to promote epithelial regeneration. For example inner portion 110 may comprise an increased apical radius of curvature relative to the radius of curvature of the ablation profile 20 of the cornea.

The amount of decreased curvature of inner portion 110 can be characterized in many ways, for example with Diopters of the cornea and Diopters of the front or back surface of the inner portion of the covering. In many embodiments the covering may comprise an inner portion having radius of curvature R1 that can be about 2D less than the optical power of the ablated cornea. For example, when the cornea is ablated from about 43D to about 40D, the base radius of curvature R1 of covering 100 correspond about 38D, two Diopters flatter than the ablated cornea so as to provide environment 100E.

The deflectable coverings having the amount of relative rigidity within the ranges as described herein can be fit to the ablated cornea in many ways. As the covering deflects, the patient can be fit with a covering that can be flatter or steeper than the ablation prior to placement on the eye, and when the covering is placed on the eye the covering can deflect substantially in response to the shape of the ablation so that the patient can see and receive the visual benefit of the ablation profile.

In many preferred embodiments, the amount of the difference in curvature between the front surface of the ablation profile and the covering prior to placement on the eye can be within a range from about 0D to about 3D so as to promote vision and epithelial regeneration. For example, the covering prior to placement with configuration 100C1 can be flatter than the cornea by an amount within a range from about 1D to about 3D, and when placed on the eye the covering deflects so as to conform at least partially to the ablated cornea. The epithelium may comprise a thickness of about 50 um. The covering prior to placement with configuration 100C1 having a curvature flatter than the cornea can decrease pressure to the epithelium near the edge of the covering as the covering with the flatter curvature may be deflected less when the inner portion conforms to the ablation. The covering prior to placement with configuration 100C1 having a curvature flatter than the cornea can increase pressure to the epithelium along the inner portion of the ablation as the covering may be deflected less when the inner portion conforms to the ablation.

In many embodiments the inner portion 110 has a substantially uniform thickness and no substantial optical power such that the optical power of the covering corresponding to the index of refraction of the covering, the upper surface of the covering, and the lower surface of the covering, comprises no more than about +/−1.5D, for example no more than +/−1D. When the covering having the substantially uniform thickness is placed on the eye and deflected so as to conform at least partially to the ablation and smooth the inner 2-3 mm of the cornea, the covering corresponds substantially to the ablation profile such that the patient can see.

Figure 1M:
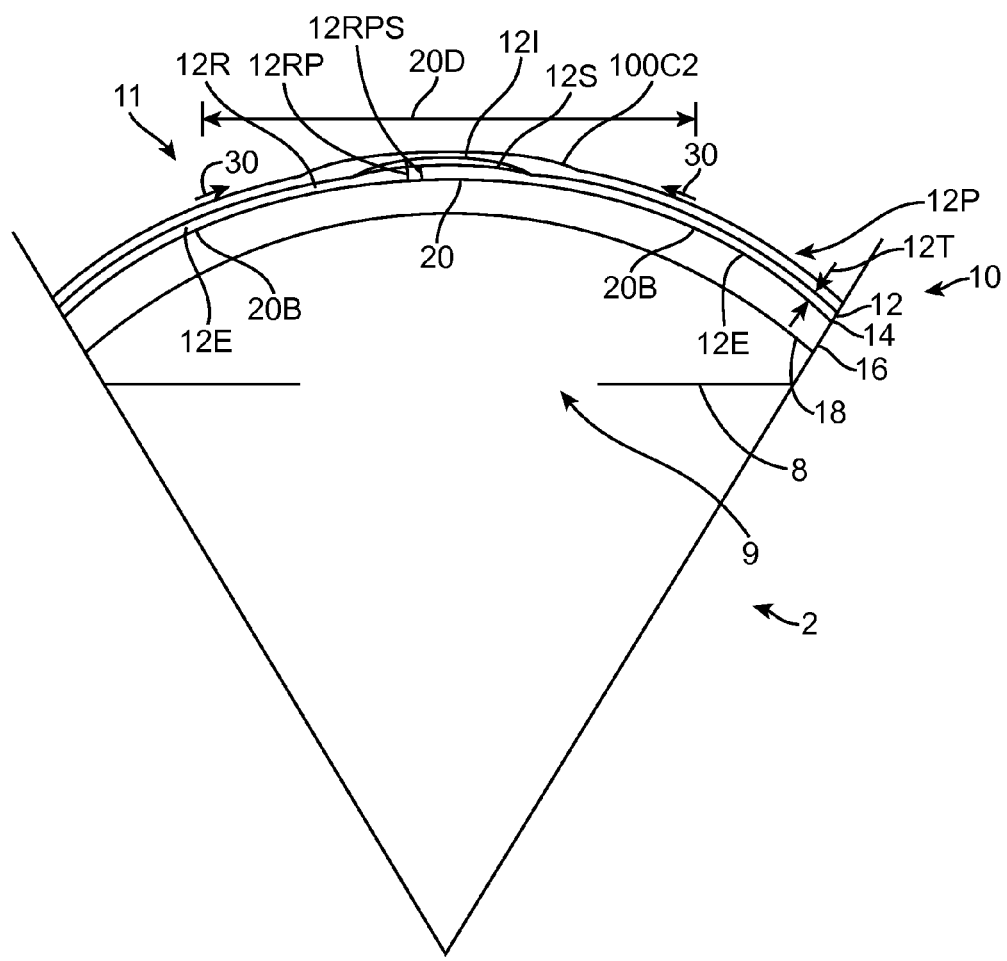
FIG. 1M shows deflection of a portion of a covering in response to an epithelial irregularity so as to smooth the irregularity, in accordance with embodiments as described herein.

FIG. 1M shows deflection of a portion of a covering in response to an epithelial irregularity so as to smooth the irregularity. The regenerating epithelium comprises a smoothed regeneration profile 12RPS and a smoothed irregularity 12S. For reference, the regeneration profile 12RP without the covering and irregularity 12I without the covering are shown. The covering can smooth the epithelium with pressure corresponding to deflection of the covering as described when the covering 100 comprises a second configuration 100C2 as described herein.

Figure 1N:
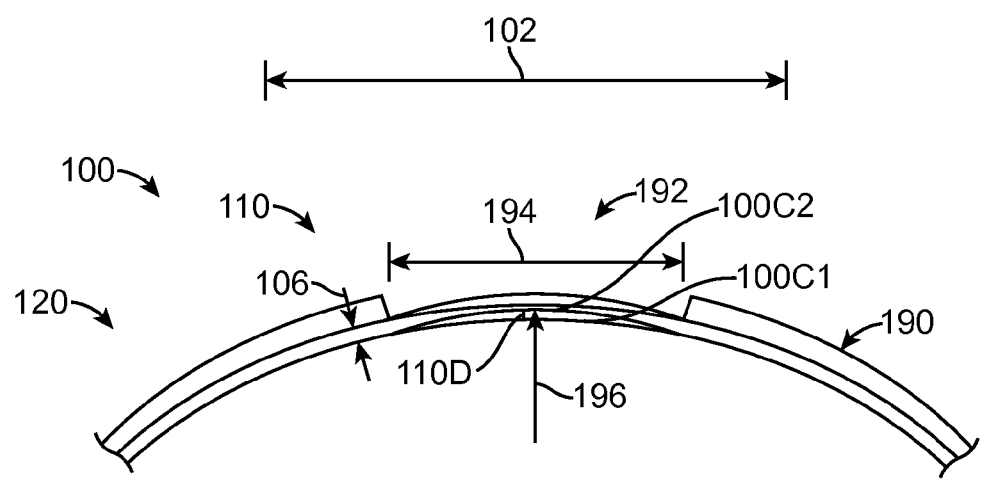
FIG. 1N shows a test apparatus to measure deflection of a portion of a lens in response to a load, in accordance with embodiments as described herein.

FIG. 1N shows a test apparatus 190 to measure deflection of a portion of a lens in response to a load. The test apparatus 190 may comprise a rigid support having an aperture 192, such that deflection of the covering 100 through the aperture 192 can be measured. The aperture 192 has a dimension across 194 that can be sized smaller than the dimension across inner portion 110, so as to measure a deflection 110D of the inner portion 110 in response to a load 196. The deflection 110D may comprise a peak deflection, for example a distance. The load 196 may comprise a point load or a load distributed over an area corresponding to diameter 104, for example a pressure from a gas or liquid on the lower side of the covering. The covering may comprise a first configuration 100C1 corresponding to the shape of the covering prior to placement on the eye, and the covering may comprise a second configuration 100C2 when placed on the eye, and the amounts of force and/or pressure to deflect covering 100 can be determined such that covering 100 can be deflected without substantially degrading vision and so as to smooth the epithelium. For example, the covering may deflect slightly so as to decrease vision no more than about 1 or 2 lines of visual acuity and such that the covering can smooth the epithelium and provide environment 100E as described herein.

The modulus and thickness of the covering can be used to determine an amount of relative rigidity of the covering 100, the corresponding amount of force to deflect the covering 100 across a distance, and the corresponding amount of pressure to smooth the epithelium with the deflected covering as described herein.

The amount of relative rigidity can be determined based on the modulus multiplied with cube of the thickness. The amount of deflection corresponds to the $6^{th}$ power of the deflected span across the covering, the modulus, and the cube of the thickness. The approximately fourth order relationship of the span to the deflection can allow the coverings as described herein to conform at least partially to the ablation profile within a range from about 4 to 6 mm, and inhibit substantially irregularities having diameters of about 3 mm or less, for example.

The deflection can be approximated with the following equation:

$$\text{Deflection} \approx (\text{constant}) * (\text{Load} * \text{Span}^4) / (\text{Modulus} * \text{thickness}^3)$$

The above approximation can be useful to understand the properties of covering 100, for example with a substantially uniform thickness of the inner portion. The substantially uniform thickness may comprise a thickness that is uniform to within about +/−25%, for example to within about +/−10%, such that the covering can conform substantially to at least a majority of the surface area of an ablation zone and inhibit irregularities over a smaller portion of the ablation zone corresponding to no more than a minority of the surface area of the ablation. In many embodiments, the covering conforms over an area having diameter of at least about 4 mm and inhibits irregularities over an area having a diameter of no more than about 4 mm, for example less inhibits irregularities over an area of no more than about 3 mm. For example, based on the above equations, the deflection is related to the fourth power of the span, such that for a comparable load, a 2 mm span will have about $1/16^{th}$ the deflection of a 4 mm span. Similarly, a 3 mm span will have a deflection that is about $1/16^{th}$ the deflection of a 6 mm span. As the deflection is related to the cube of the thickness, doubling the thickness can decrease the deflection by about a factor of 8. The above approximations can be combined with clinical testing to determine thicknesses and moduli suitable for incorporation in accordance with embodiments as described herein.

The equations for deflection of an unsupported circular span of a material having a substantially uniform thickness are:

$$E_c = E_1\left(\frac{t_1}{t_1 + t_2}\right) + E_2\left(\frac{t_2}{t_1 + t_2}\right)$$

curved surface and a person of ordinary skill in the art can determine the deflection load and relative rigidity empirically based on the teachings described herein, for example with finite element modeling.

TABLE A1

Material, modulus, thickness, relative rigidity Dk/and deflection load of inner portions of coverings as described herein.

| Button Material | Uniform Button Thickness (um) | Button Thickness (m) | Flexural Modulus (MPa) | Flexural Modulus (Pa) | Relative Rigidity (Pa*m^3) | Material Dk | Dk/t |
|---|---|---|---|---|---|---|---|
| Rigid Silicone | 250 | 2.50.E−04 | 35 | 35000000 | 5.47E−04 | 600 | 240 |
| Rigid Silicone | 200 | 2.00.E−04 | 35 | 35000000 | 2.80E−04 | 600 | 300 |
| Rigid Silicone | 150 | 1.50.E−04 | 35 | 35000000 | 1.18E−04 | 600 | 400 |
| Rigid Silicone | 100 | 1.00.E−04 | 35 | 35000000 | 3.50E−05 | 600 | 600 |
| Rigid Silicone | 50 | 5.00.E−05 | 35 | 35000000 | 4.38E−06 | 600 | 1200 |
| Exemplary Silicone | 293 | 2.93.E−04 | 20 | 20000000 | 5.03E−04 | 600 | 205 |
| Exemplary Silicone | 272 | 2.72.E−04 | 20 | 20000000 | 4.02E−04 | 600 | 221 |
| Exemplary Silicone | 250 | 2.50.E−04 | 20 | 20000000 | 3.13E−04 | 600 | 240 |
| Exemplary Silicone | 215 | 2.15.E−04 | 20 | 20000000 | 1.99E−04 | 600 | 279 |
| Exemplary Silicone | 200 | 2.00.E−04 | 20 | 20000000 | 1.60E−04 | 600 | 300 |
| Exemplary Silicone | 175 | 1.75.E−04 | 20 | 20000000 | 1.07E−04 | 600 | 343 |
| Exemplary Silicone | 150 | 1.50.E−04 | 20 | 20000000 | 6.75E−05 | 600 | 400 |
| Exemplary Silicone | 100 | 1.00.E−04 | 20 | 20000000 | 2.00E−05 | 600 | 600 |
| Exemplary Material | 50 | 5.00.E−05 | 20 | 20000000 | 2.50E−06 | 600 | 1200 |
| enflufocon A (Boston ES) | 25 | 2.50.E−05 | 1900 | 1900000000 | 2.97E−05 | 18 | 72 |
| enflufocon A | 50 | 5.00.E−05 | 1900 | 1900000000 | 2.38E−04 | 18 | 36 |
| enflufocon A | 150 | 1.50.E−04 | 1900 | 1900000000 | 6.41E−03 | 18 | 12 |
| hexafocon B (Boston XO2) | 25 | 2.50.E−05 | 1160 | 1160000000 | 1.81E−05 | 141 | 564 |
| hexafocon B | 50 | 5.00.E−05 | 1160 | 1160000000 | 1.45E−04 | 141 | 282 |
| hexafocon B | 150 | 1.50.E−04 | 1160 | 1160000000 | 3.92E−03 | 141 | 94 |

-continued

"Relative" Rigidity $= E_c(t_1 + t_2)^3$ $$y = \frac{3wR^4}{16Et^3}(5 + v)(1 - v)$$

$$w = \frac{y16Et^3}{(5 + v)(1 - v)3R^4}$$

where:
W=evenly distributed load over the surface, Pressure (Pa)
R=span of unsupported material (m)
E=Young's Modulus (Pa)
t=Thickness (m)
v=Poisson's Ratio (unit-less, assumed to be constant among materials)
y=Deflection (m)

Equations for deflection is described in *Theory and Analysis of Elastic Plates*, Junuthula Narasimha Reddy, p. 201 equation 5.3.43 (1999).

Although the above equations describe relative rigidity for a substantially flat surface, the equations can approximate a As shown in Table A1, an RGP material such as an enflufocon or hexafocon having a thickness of about 50 um can have a relative rigidity suitable for epithelial smoothing and so as to conform at least partially to the ablated stroma. The rigid silicone having a modulus of about 20 MPa and a thickness of about 250 um will provide a relative rigidity 3E-4 and deflection under load similar to the RGP material having a thickness of about 50 um and modulus of about 1900 MPa so as to provide a relative rigidity of about 2.4E-4. Commercially available RGP lens materials as shown in Table A1 can be combined in accordance with embodiments as described herein so as to provide covering 100. Based on the teachings described herein, a person of ordinary skill in the art can determine the thickness of the covering based on the modulus and the intended relative rigidity.

Work in relation to embodiments in accordance with clinical studies as described herein has shown that the inner portion 110 of the covering 100 having the relative rigidity of about 3E-4 ($3\times10^{-4}$ Pa*m^3) can be effective so to improve vision and conform at least partially of the eye so as to provide at least some comfort and improve fitting. Many eyes have been measured with many coverings and work in relation to embodiments indicates that an inner portion 110 having a relative rigidity within a range from about 1E-4 to about 5E-4 (Pa*m^3) can allow the covering to conform to the ablation and smooth the epithelium as described herein. For example, inner portion 110 may have a relative rigidity within a range from about 2E-4 to about 4E-4, and the eye can be fit accordingly based on the deflection of the covering 100.

The relative rigidity can be related to the amount of deflection of the covering 100 on the eye. Work in relation to embodiments indicates that a relative rigidity of inner portion 110 about 3E-4 can deflect about +/−2D when placed on the eye so as to conform to an ablation to within about +/−2D across the approximately 5 or 6 mm ablation diameter when an inner diameter of about 2 or 3 mm is smoothed. A covering 100 having a relative rigidity of about 1.5 E-4 can deflect about +/−4D when placed on the eye so as to conform to an ablation to within about +/−4D across an approximately 5 or 6 mm diameter when an inner diameter of about 2 or 3 mm is smoothed.

The outer portion of the covering may comprise a relatively rigidity less than the inner portion to fit an outer portion of the eye such as an outer portion of the cornea or to fit the sclera when placed on the conjunctiva.

The coverings as described herein may comprise a relative rigidity corresponding to a range within two or more values of many of the coverings of Table A1, for example a relative rigidity within a range from about 2.50E-06 to about 6.41E-03(Pa*m^3), and two or more intermediate values for example within a range from about 6.75E-05 to about 5.47E-04(Pa*m^3). Based on the teachings described herein the covering can have a relative rigidity within one or more of many ranges such as within a range from about 0.5E-3 to about 10E-3 (Pa*m^3), for example a range from about 1E-3 to about 6E-3, for example. Based on the teachings described herein, a person of ordinary skill in the art can conduct clinical studies to determine empirically the thickness and modulus corresponding to a relative rigidity of the inner portion 110 for the covering 100 so as to smooth irregularities and conform substantially to the ablation zone.

TABLE A2

Pressure for 5 um deflection at diameters of 3, 4, 5 and 6 mm for coverings of Table A1.

| Button Material | Button Thickness (um) | Relative Rigidity (Pa*m^3) | Pressure Required to obtain 5 um deflection (Pa) | | | |
|---|---|---|---|---|---|---|
| | | | 3 mm span | 4 mm span | 5 mm span | 6 mm span |
| Rigid Silicone | 250 | 5.47E−04 | 1002.2 | 317.1 | 129.9 | 62.6 |
| Rigid Silicone | 200 | 2.80E−04 | 513.1 | 162.4 | 66.5 | 32.1 |
| Rigid Silicone | 150 | 1.18E−04 | 216.5 | 68.5 | 28.1 | 13.5 |
| Rigid Silicone | 100 | 3.50E−05 | 64.1 | 20.3 | 8.3 | 4.0 |
| Rigid Silicone | 50 | 4.38E−06 | 8.0 | 2.5 | 1.0 | 0.5 |
| Exemplary Silicone | 293 | 5.03E−04 | 921.9 | 291.7 | 119.5 | 57.6 |
| Exemplary Silicone | 272 | 4.02E−04 | 737.6 | 233.4 | 95.6 | 46.1 |
| Exemplary Silicone | 250 | 3.13E−04 | 572.7 | 181.2 | 74.2 | 35.8 |
| Exemplary Silicone | 215 | 1.99E−04 | 364.3 | 115.3 | 47.2 | 22.8 |
| Exemplary Silicone | 200 | 1.60E−04 | 293.2 | 92.8 | 38.0 | 18.3 |
| Exemplary Silicone | 175 | 1.07E−04 | 196.4 | 62.2 | 25.5 | 12.3 |
| Exemplary Silicone | 150 | 6.75E−05 | 123.7 | 39.1 | 16.0 | 7.7 |
| Exemplary Silicone | 100 | 2.00E−05 | 36.7 | 11.6 | 4.8 | 2.3 |
| Exemplary Silicone | 50 | 2.50E−06 | 4.6 | 1.4 | 0.6 | 0.3 |
| enflufocon A (Boston ES) | 25 | 2.97E−05 | 54.4 | 17.2 | 7.1 | 3.4 |
| enflufocon A | 50 | 2.38E−04 | 435.2 | 137.7 | 56.4 | 27.2 |
| enflufocon A | 150 | 6.41E−03 | 11751.3 | 3718.2 | 1523.0 | 734.5 |
| hexafocon B (Boston XO2) | 25 | 1.81E−05 | 33.2 | 10.5 | 4.3 | 2.1 |
| hexafocon B | 50 | 1.45E−04 | 265.7 | 84.1 | 34.4 | 16.6 |
| hexafocon B | 150 | 3.92E−03 | 7174.5 | 2270.1 | 929.8 | 448.4 |

The data of Table A1 and A2 show that the pressure to deflect a 3 mm zone a distance of 5 um can be about three times the pressure to deflect a 4 mm zone the distance of 5 um, and about 15 times the pressure to deflect the 6 mm zone the 5 um distance. For example, for the relative rigidity of about 3.13E-4 (Pa*m^3), the 5 um deflection pressures are 572.7, 181.2, 74.2, 35.8 (Pa) for diameters of 3, 4, 5 and 6 mm, respectively, such that the central 3 mm of inner portion 110 can provide a compressive force to irregularities of about 570 Pa when the inner portion 110 conforms to the ablation across a 6 mm span with a pressure of about 35 Pa, for example.

The relative rigidity and deflection pressures can be determined for many coverings based on the teachings described herein, for example for coverings having a plurality of layers having a plurality of materials.

TABLE A3

Relative Rigidity of Layered Coverings

| Total Thickness | Layered Material | Material 1 (Rigid) | | Material 2 (Soft) Flexural | | Composite | | Composite Relative Rigidity (Pa*m^3) |
|---|---|---|---|---|---|---|---|---|
| | | Thickness (m) | Modulus (Pa) | Thickness (m) | Modulus (Pa) | Thickness (m) | Modulus (Pa) | |
| 270 um thick | Exemplary Silicone Shield | 2.40E−04 | 2.00E+07 | 3.00E−05 | 2.00E+06 | 2.70E−04 | 1.80E+07 | 3.54E−04 |

TABLE A3-continued

Relative Rigidity of Layered Coverings

| | | Material 1 (Rigid) | | Material 2 (Soft) | | Composite | | |
|---|---|---|---|---|---|---|---|---|
| | | | | | Flexural | | Composite | Relative |
| Total Thickness | Layered Material | Thickness (m) | Modulus (Pa) | Thickness (m) | Modulus (Pa) | Thickness (m) | Modulus (Pa) | Rigidity (Pa*m^3) |
| | Soft and Hard are Equal | 1.35E−04 | 2.00E+07 | 1.25E−04 | 2.00E+06 | 2.70E−04 | 1.13E+07 | 1.99E−04 |
| 150 um thick | Exemplary Silicone Shield | 1.20E−04 | 2.00E+07 | 3.00E−05 | 2.00E+06 | 1.50E−04 | 1.64E+07 | 5.54E−05 |
| | Soft and Hard w/ Equal thickness | 7.50E−05 | 2.00E+07 | 7.50E−05 | 2.00E+06 | 1.50E−04 | 1.10E+07 | 3.71E−05 |

When two or more materials are combined so as to provide two or more layers, the relative rigidity of each layer can be combined so as to determine a total composite rigidity. For example, the combined rigidity can be determined for a covering having first layer 100L1 of first material, a second layer 100L2 of second material 110M2 and third layer 100L3 of third material 100L3, in which the first and third materials can be the same material.

A weighted average system can be used to treat the two layers as one material. The relative amounts of each material and the moduli of the two materials can be combined to determine a composite modulus based on the weight average of the thickness of each layer. For example, with 90 um of 20 Mpa material layer and a 10 um of 5 MPa material layer can be combined so as to determine the composite modulus as 20 MPa*0.9+5 MPa*0.1=18.5 MPa The equations described herein accommodate many layers of different materials and thicknesses.

Based on the composite modulus, one can multiply the composite modulus by the overall thickness cubed, in the present example 18.5 MPa*100^3. Although these calculations can be based on approximations, a person of ordinary skill in the art can conduct simulations, for example finite element modeling simulations, so as to determine the amount of relative rigidity, pressures and deflection forces and pressures as described herein.

The index of refraction of one or more layers of covering 100 may correspond substantially to the index of refraction of the cornea.

One or more of the materials 110M1, 110M2 or 110M3 may comprise an index of refraction within a range from about 1.38 to about 1.43 so as to match the index of refraction of the cornea to within about +/−0.05. For example, the materials 110M1 and 110M3 may comprise an optically transparent soft silicone elastomer having an index of refraction of about 1.41 and the material 110M2 may comprise an optically transparent rigid silicone elastomer having an index of refraction of about 1.43, for example available from NuSil. Alternatively, material 110M1 and material 110M3 may comprise silicone hydrogel and material 110M2 may comprise silicone, for example.

While the covering may comprise similar materials such as a more rigid silicone combined with a softer silicone, the covering may comprise dissimilar materials. For example, and RGP material can be combined with a hydrogel, such as the bicurve or tricurve embodiments as described herein. The covering can extend at least to the limbus for stability. The RGP material may comprise the second layer 100/2 of the second material 110M2, for example in accordance with Table A, and the hydrogel may comprise the first layer 100/1 of the first material 110M1 and the third layer 100/3 of the third material 110M3. The hydrogel may have an index of refraction from about 1.38 to about 1.42 so as to match the index of refraction of the cornea of about 1.377 to within about 0.05 and may comprise one or more of HEMA, NVP, GMA, MMA, SiH, TRS, HEMA/NVP, MMA/NVP, HEMA/GMA, or SiH/TRS, commercially available from Vista Optics, UK, for example. The hydrogel comprising HEMA/NVP, MMA/NVP, or HEMA/GMA may have water content within a range from about 40% to about 70% so as to comprise the index of refraction within the range from about 1.38 to about 1.43. A water content of about 40% corresponds to an index of refraction of about 1.43 and a water content of about 70% corresponds to an index of refraction of about 1.38. The hydrogel comprising SiH/TRS may comprise water content within a range from about 20% to about 70% so as to comprise the index of refraction within the range from about 1.38 to about 1.43. With these SiH hydrogels a water content of about 20% corresponds to an index of refraction of about 1.43 and a water content of about 70% corresponds to an index of refraction of about 1.38.

Coverings Configured to Pump Tear Liquid

FIG. 2A1 shows covering 100 configured to pump tear liquid when positioned on a blinking eye.

FIG. 2A2 shows the covering of FIG. 2A1 configured to pump tear liquid under the covering. The covering 100 has inner portion 110 and outer portion 120, and fenestrations 100F extending through the thickness of the covering on the outer portion so as to tear liquid TL, which may comprise a medicament. The medicament may comprise an anesthetic, an analgesic, or other medication, for example.

The covering 100 comprises an optical component 100A and a coupling component 100B. The optical component 100A may comprise an inner portion 110 of covering 100 and the coupling component 100B may comprise an outer portion 120 of covering 100. The optical component 100A comprises rigidity sufficient to resist deformation such that the optical component 100A can correction vision of the eye. The optical component 100A may comprise a single layer of material, or a plurality of layers of materials. The coupling component 100B may comprise a rigidity less than optical component 100A, such that the coupling component can one or more of deflect or elastically deform so as to conform to the cornea when covered with the eyelid. The coupling component 100B may comprise an inner component 100B1 to couple to the optical component, an outer portion 100B3 to couple to the sclera, and an intermediate portion 100B2. The intermediate portion 100B2 can extend between the inner component 100B1 and the outer component 100B3 so as define a chamber when placed on the eye.

The optical component 100A and the coupling component 100B can pump tear liquid under the cornea when the eye closes and opens, for example when the eye blinks. The outer component 100B3 comprising outer portion 120 may comprise fenestrations 100F. For example, the intermediate portion 100B2 may comprise fenestrations 100F. The outer portion 120 may comprise outer portion 100B3 comprising a sclera coupling portion 130 to contact the conjunctiva over the sclera and peripheral portion 120P. The sclera coupling portion 130 may comprise a thin flange portion extending to the peripheral portion 120P. The sclera coupling portion may comprise a thin elastic portion capable of elastic deformation when the eye blinks to allow the optical component to move downward. Alternatively or in combination, the outer portion 120 may comprise a rigidity sufficient to deflect when the eye blinks.

FIG. 2A3 shows a schematic illustration of the covering of FIGS. 2A1 and 2A2 pumping tear liquid when the eye closes, in accordance with embodiments of the present invention;

When placed on the eye, the covering 100 can define a chamber with the lower surface of the covering extending along the cornea, the limbus and conjunctiva over the sclera. When the eyelids are separated, the covering 100 is held loosely on the eye with slight pressure from the eyelids extending under the outer portion of the covering. When the eye blinks, the lids extend over the outer portion 120 of the covering and inner portion 110 so as to exert pressure on the covering such that the covering is urged downward toward the cornea and the volume of the chamber under the covering is decreased. The downward movement of the optical component 100A of the inner portion 110 of the covering 100 can move the covering downward so as to pass pumped tear liquid 100TL through the fenestrations, and in many embodiments the pumped tear liquid 100TL can pass under the peripheral portion 120P.

FIG. 2A4 shows a schematic illustration of the covering of FIGS. 2A1 and 1A2 pumping tear liquid when the eye opens, in accordance with embodiments of the present invention.

When the eyelids open, the pressure on the covering is decreased, such that the covering can move away from the cornea and increase the volume of the chamber. The movement of the optical portion 100A away from the cornea can draw pumped tear liquid 100TL into the covering through the fenestrations, and contact of the peripheral portion 120P and sclera coupling portion 130 with the conjunctiva can inhibit flow of tear liquid under the peripheral portion 120P. In many embodiments, the peripheral portion 120P and sclera coupling portion 130 can contact the conjunctiva so as to form a seal when the eyelids open and the optical portion 100A moves away from the cornea.

The fenestrations 100F can be located away from the optical component, for example about 3.5 to about 4.5 mm from a center of the optical component to decrease optical artifacts of the fenestrations 100F. However, the fenestrations may be located within the optical component when one or more of sufficiently small or sufficiently few so as to not produce perceptible visual artifacts. The fenestrations may comprise a patter to indicate the orientation of the covering 100 on the cornea. For example the upper fenestration and lower fenestrations may indicated a 90 degree axis on the patient and horizontal fenestrations can be provided to indicated the location of the 180 degree axis on the patient. The fenestrations may comprise additional fenestrations to be located inferiorly to indicate that the covering is not flipped by 180 degrees on the patient, for example upside down. The additional inferior fenestrations may also couple to the rivulet comprising tear liquid that forms near the lower lid, so as to facilitate pumping of tear liquid. For example, when the eye blinks the lower lid may extend over the inferior fenestrations and the upper lid may extend downward to couple to the lower rivulet. When the eye opens and the eyelids separate the upper eyelid can draw tear liquid of the rivulet over the upper fenestration and the lower eyelid can move inferiorly so as to pass the rivulet over the inferior rivulets.

The covering 100 may comprise a base radius R1 of curvature corresponding to a curvature of a central portion of the cornea. The covering 100 comprises a first configuration 100C1 when placed on the cornea and the eyelids are spaced apart and a second configuration 100C2 when placed on the cornea and the blinks such that the eyelids. The first configuration 100C1 and the second configuration 100C2 pump tear liquid under the covering 100.

The covering 100 may comprise a lower surface corresponding to one or more of many suitable shapes to fit the covering to the cornea, such as a natural unablated cornea or an ablated cornea following refractive surgery such as PRK. The lower surface of the inner portion 110 of the covering 100 may correspond to base radius of curvature. With post ablation corneas, the covering can resist deformation and smooth the epithelium over about 3 mm and may deflect so as to conform substantially to the ablated cornea over a larger dimension such as 6 mm. The covering may comprise a second curve in combination with a first curve, such that the lower surface comprises a bicurve surface. Alternatively, the lower surface may correspond to an aspheric surface. For example, an aspheric surface may comprise an oblate shape and conic constant to fit a post PRK eye. The curved and aspheric surfaces as described herein can fit non-ablated eyes and the covering can be selected by based on the curvature of an unablated central region of the cornea. Also, it may be helpful to identify a covering that fits the cornea, for example with selection of one covering from a plurality of sizes.

The covering 100 may comprise an inner portion 110 having an optical component 1 100A. The optical component 100A may comprise an inner portion 110 of the covering 100. The optical component may have a modulus within a range from about 5 MPa to about 40 MPa, and a thickness within a range from about 100 um to about 300 um such that central portion can have sufficient rigidity to resist deformation and smooth irregularities and correct vision. The covering may comprise an elastomeric stretchable material such that the covering can stretch to fit the cornea, for example. The covering having the modulus within a range from about 4 MPa to about 40 MPa can be formed in many ways as described herein. For example, the covering may comprise a single piece of material having a non-uniform thickness extending across the cornea. The covering can be shaped in many ways and may comprise a single piece of one material, or may comprise a single piece composed to two similar materials, or may comprise a plurality of materials joined together.

FIG. 2B1 shows covering 100 having a tricurve profile to fit sclera and cornea. The tricurve profile can be used to fit an unablated natural eye, in which the base curvature R1 corresponds to the optically used central portion of the cornea. For ablated corneas, the base curvature R1 may correspond to the ablated cornea. The tricurve covering may comprise an inner portion with an inner lower surface having radius of curvature R1 and an outer portion comprising an outer lower surface having radius of curvature R1B. The outer portion 120 may comprise the sclera coupling portion 130 having a third radius of curvature R1C sized to fit the conjunctiva located over the sclera and contact the conjunctiva so as to inhibit sliding movement of inner portion 110. Work in relation to embodiments suggests that coupling to the sclera may improve alignment of the lens on the cornea.

The covering 100 having the tricurve profile may comprise dimensions sized to fit the cornea and sclera of the eye 2. The covering 100 having the at least tricurve profile may comprise an inner portion 110 and an outer portion 120 as described herein. The outer portion 120 may comprise the third sclera coupling portion 130 having curvature R1C shaped to fit the sclera of the eye, for example shaped so as to contact the conjunctiva of the eye such that the conjunctiva is located between the sclera and the sclera coupling portion 130. The inner portion 110 may comprise a dimension 102 and the outer portion 120 may comprise a dimension 104 as described herein. The covering 100 may comprise a sag height 105 extending between an upper location of the inner portion 110 and the outer boundary of outer portion 120 shaped to fit the cornea. The sclera coupling portion 130 may comprise a dimension across 103.

The dimension 102, the dimension 104, the dimension 103, the dimension 105 and the dimension 105S can be sized to the eye based on measurements of the eye. The dimension 103 may correspond to an annular region of the sclera extending from the limbus to the outer boundary of the sclera coupling portion across a distance within a range from about 1 to 4 mm, for example within a range from about 1.5 to 2 mm. The size of the limbus of the eye can be measured so as to correspond to dimension 104, for example, and can be within a range from about 11 to 13 mm. The dimension 105 may correspond to a height of the eye from the vertex of the cornea to the limbus, and the dimension 105S may correspond to the sag height were the outer location of the covering couples to the conjunctiva covering the sclera.

The dimension 102 may correspond to an inner region of the natural cornea or the dimension across an ablation. Dimension 102 may correspond to the more rigid inner portion 110 can be sized about 0.5 to about 2 mm less than the dimension across the ablation zone, such that the soft and less rigid outer portion 120 contacts the eye near the edge of the ablation and the epithelial debridement.

The radius of curvature R1C of portion 130 can be determined so as to fit the eye, and can be within a range from about 12 mm+/−3 mm. The radius R1B of the outer portion can be fit to within about +/−0.5 mm, for example to within about +/−0.25 mm.

The dimensions of the covering 100 can be determined in many ways, for example with topography measurements of the cornea and sclera. The corneal and scleral topography can be measured with many instruments, such as with the Orbscan™ topography system commercially available from Bausch and Lomb, and the Pentacam™ Scheimpflug camera system commercially available from Oculus, and commercially available optical coherence tomography (OCT). The ablation profile can be combined with the topography to determine the shape of the eye.

The dimensions of covering 100 can be sized to one or more of the cornea and sclera based on tolerances that may be determined clinically.

The outer portion 120 and sclera coupling portion 130 may comprise a hydrogel material, for example a silicone hydrogel material, and the inner portion 110 may comprise the rigid material 110M, for example second layer 100L2 and second material 110M2 between first layer 100L1 of first material 110M1 and third layer 100L3 of third material 110M3 as described herein.

The portions of the coverings as described herein, for example the inner portion and the outer portion, may comprise a junction wherein a first portion connects with a second portion, and the junction may have the modulus as described herein. The covering may comprise a contact lens having a central lens portion having a center stiffness of at least about 2 psi*mm2 coupled to an outer lenticular junction portion having a lenticular junction stiffness of at least about 5 psi*mm2.

FIG. 2B2 shows covering 100 having a tricurve profile to fit sclera with slopes of the curved profiles aligned so as to inhibit ridges at the boundaries of the curved portions, in accordance with embodiments of the present invention. The inner portion 110 comprises the optical component 100A and the outer portion 120 comprises the coupling component 100B. The coupling component 100B may comprise a thin layer of material 120M extending under the optical component 100A for improved comfort and support of the optical component. The outer portion 120 comprising coupling component 100B may comprise fenestrations 100F as described herein. The inner portion 120 comprises first radius R1 along the lower surface and a first anterior radius R1A along the upper surface. The outer portion 120 couples to the inner portion with a second radius R1B aligned with the first radius R1A at a boundary corresponding to dimension 102. The outer portion 120 has a second anterior radius R1BA extending along the anterior surface. The outer portion 120 comprising second radius R1B along the lower surface to contact the cornea may couple to sclera coupling portion 130 at a location corresponding to the limbus of the eye, for example along a boundary corresponding to dimension 104. Work in relation to embodiments suggests that formation of a ridge near the boundary of the cornea contacting portion and sclera coupling portion may decrease epithelial cell migration somewhat more than would be ideal, and the alignment of the curved profiles to inhibit ridge formation can provide a smooth transition over the limbus and may decrease mechanical pressure to the limbus. The sclera contacting portion 130 comprises an upper surface having an anterior radius of curvature R1CA.

The inner portion 110 can be curved to fit an ablated eye or a non-ablated eye. The modulus and thickness of the sclera coupling portion can be configured in many ways to fit many eyes with comfort and so as to resist movement of the inner portion 120. The modulus of sclera coupling portion 130 may be no more than about 5 MPa and the thickness no more than about 200 um, for example no more than 100 um, so as to stretch substantially for comfort and resist movement of the inner portion when placed on the sclera.

The dimension 103 of sclera coupling portion 130 may correspond to an annular region of the sclera extending from the limbus to the outer boundary of the sclera coupling portion across a distance within a range from about 1 to 4 mm, such that the dimension 103 can be from about 12 mm to about 16 mm, for example from about 14 mm to about 16 mm.

The radius of curvature R1C, thickness and modulus of the portion 130 can be configured so as to fit the eye to resist movement of inner portion 110 and with comfort. The radius of curvature R1C can be sized less than the radius of curvature of the sclera and conjunctiva. For example, the radius of curvature R1C can be no more than about 10 mm, for example no more than about 9 mm when the curvature of the sclera portion of the eye is at least about 12 mm for example. The third relative rigidity may comprise no more than about 4E-5 Pa*m^3 so as to stretch substantially for comfort and resist movement of the inner portion when the outer portion is placed on the sclera.

The thickness of the sclera coupling portion having radius of curvature R1C can vary, for example from a thickness of about 100 um to a tapered edge.

FIG. 2B2-1 shows alignment of the slope of the lower surface of the corneal contacting portion comprising second radius R1B with the slope of the lower surface of the sclera coupling portion 130 comprising radius R1C, such that pressure to the limbus is decreased substantially. The second slope corresponding to second radius R1B is given by a height R1BY and a length R1BX, and the third slope corresponding to third radius R1C is given by height R1CY and width R1CX. The second slope is aligned with the third slope such that no substantial ridge is formed at the location corresponding to the limbus. For example, the first slope can be substantially equal to the second slope. The slope of the inner portion 110 can be aligned with the slope of the second portion 120 at a location corresponding to dimension 102 in a similar manner.

FIG. 2B3 shows a tapered edge of the covering of FIG. 2B1 having a tricurve profile to fit sclera and cornea. The sclera coupling portion 130 may comprise a flange 120F having a narrowing taper extending a distance 120FW to a chamfer 120FE. The chamfer 120FE can be defined along an outer rim where a first convexly curved lower surface joins a second convexly curved upper surface. The convex surfaces along the outer rim allow the covering to slide along the conjunctiva and the narrowing taper permits the sclera coupling portion of the covering to stretch substantially and couple to the sclera and conjunctiva with decreased resistance for comfort.

The dimensions of the covering 100 can be determined in many ways, for example with one or more topography measurements or tomography measurements of the cornea and sclera. The corneal and sclera topography can be measured with many instruments, such as with the Orbscan™ topography system commercially available from Bausch and Lomb, and the Pentacam™ Scheimpflug camera system commercially available from Oculus. The tomography can be measured with optical coherence tomography (hereinafter "OCT") so as to determine the sag height of the limbus and conjunctiva, for example with OCT measurement systems commercially available from Zeiss/Humphrey. The ablation profile can be combined with the topography to determine the shape of the eye.

FIG. 2B4 shows a plan view covering 100 having a multi-curve profile to fit the cornea, limbus and sclera with slopes of the curved profiles aligned so as to inhibit ridges at the boundaries of the curved portions, in accordance with embodiments of the present invention. The covering 100 comprises fenestrations 100F and optical component 100A for vision correction and outer coupling component 100B that may pump tear liquid as described herein.

FIG. 2B5 shows a side sectional view of the covering of FIG. 2B4 and corresponding curved portions to couple to the cornea, limbus and sclera, in accordance with embodiments of the present invention;

The inner portion 110 comprises optical component 100A which may comprise material 110M. The outer portion 120 comprises coupling component 100B which may comprise outer material 120M. The inner portion 110 is coupled to the outer portion along a boundary corresponding to dimension 102. The lower surface of inner portion 110 has a shape profile corresponding to a first radius R1. The outer portion 120 couples to the inner portion with a first outer radius R1B1 of curvature, such that the slopes are aligned as described herein at a location corresponding to dimension 102. The outer portion 120 comprises a second outer radius R1B2 of curvature coupled to the first outer radius of curvature R1B1. The first outer radius R1B1 of curvature is coupled to the second outer radius R1B2 of curvature with the slopes aligned as described herein at a location corresponding to dimension 104A. The outer portion 120 comprises a third outer radius R1B3 of curvature coupled to the second outer radius of curvature R1B2. The second outer radius R1B2 of curvature is coupled to the third outer radius R1B3 of curvature with the slopes aligned as described herein at a location corresponding to dimension 104B.

The first outer radius of curvature R1B1, the second outer radius of curvature R1B2, and the third outer radius of curvature R1B3 may comprise values determined from a patient population. The first radius of curvature R1 may comprise a value determined based on the patient population. Alternatively or in combination, the first radius of curvature R1 may correspond to a post ablation profile.

The first outer radius of curvature R1B1, the second outer radius of curvature R1B2, and the third outer radius of curvature R1B3 can be combined or replaced with an aspheric surface such as a conic surface. The conic surface can be determined in accordance with first outer radius of curvature R1B1, the second outer radius of curvature R1B2, and the third outer radius of curvature R1B3, such that the conic surface corresponds to values determined from a patient population.

The sclera coupling portion 130 may have a lower surface comprising a first sclera coupling radius R1C1 of curvature and a second sclera coupling portion having a second sclera coupling radius R1C2 of curvature. The first sclera coupling portion comprising radius R1C1 can be aligned to the third radius R1B3 at a location corresponding to dimension 104. The second sclera coupling portion comprising radius R1C2 can be aligned to the first sclera coupling portion having radius R1C1 at a location corresponding to dimension 120FW corresponding to an inner boundary of tapering flange 120F.

FIG. 2B6 shows a side sectional view of the covering of FIG. 2B4 and corresponding curved portions of the upper surface, in accordance with embodiments of the present invention. The upper surface may comprise an inner anterior radius of curvature R1A, a first outer anterior radius of curvature R1B1A, a second outer anterior radius of curvature R1B2A. The sclera coupling portion 130 may comprise a first anterior radius R1C1A of curvature and a second anterior coupling radius R1C2A of curvature.

Figure 3A:
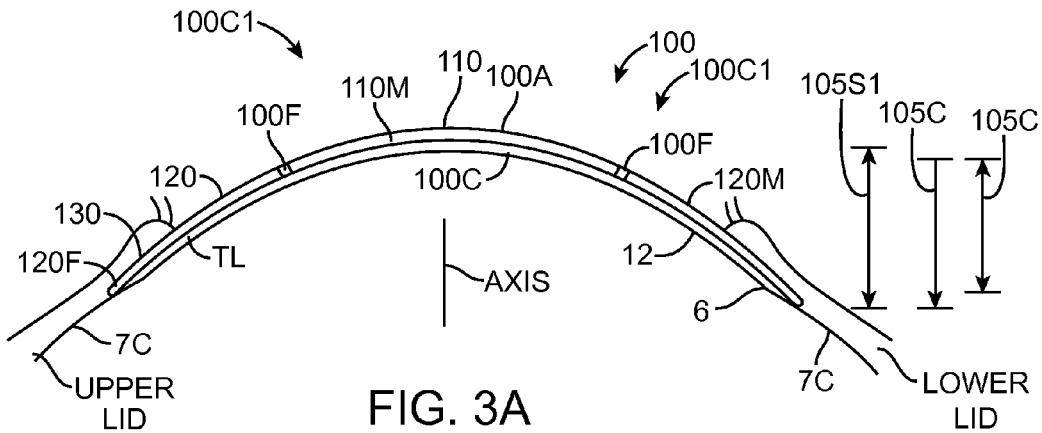
FIG. 3A shows a covering comprising a contact lens placed on the eye with the eyelids separated, in accordance with embodiments of the present invention.

FIG. 2B7 shows a tapered edge of the covering of FIG. 2B4, in accordance with embodiments of the present invention;

FIG. 3A shows a covering 100 comprising a contact lens placed on the eye with the eyelids separated, in accordance with embodiments of the present invention. The covering 100 is placed on the eye such that the tear liquid TL extends under at least a portion of the covering between the covering and the cornea so as to provide a chamber 100C. The covering 100 can be fit so as to match substantially the curvature of the cornea (hereinafter "on K") or fit slightly flatter than the cornea so as to provide chamber 100C. Alternatively or in combination, the flange 120F and sclera coupling portion 120S of the outer portion 120 may comprise an angle steeper than the conjunctiva such the covering is urged away from the cornea near inner portion 110 so as to provide chamber 100C. The covering 100 comprises a sag height 105S1 corresponding to the elevation distance from the center of the covering to the outer perimeter 120P of the sclera coupling portion 130. The eye lids can be separated for the patient to see an object.

Figure 3B:
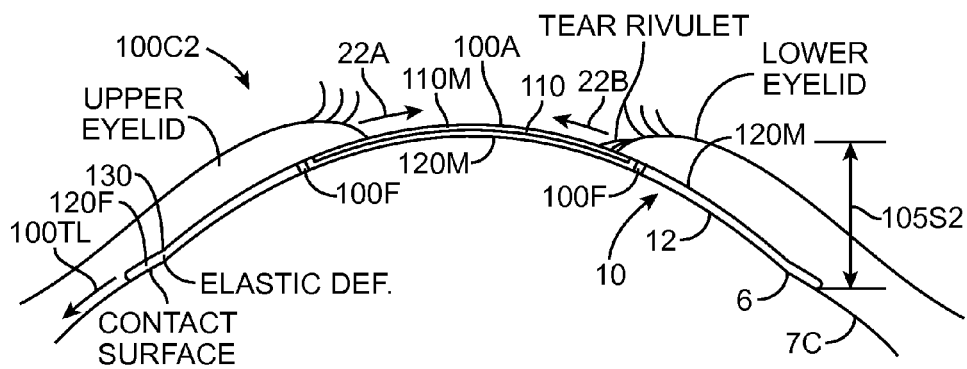
FIG. 3B shows a side sectional view of the covering of FIG. 3A with the eyelids closing, in accordance with embodiments of the present invention.

FIG. 3B shows a side sectional view of the covering of FIG. 3A with the eyelids closing.

Figure 3C:
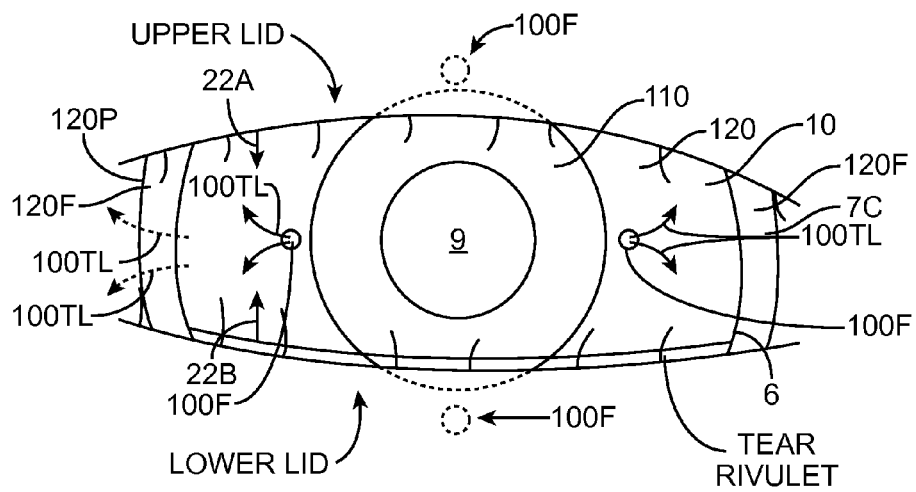
FIG. 3C shows a front view the covering of FIG. 3A with the eyelids closing, in accordance with embodiments.

FIG. 3C shows a front view the covering of FIG. 3A with the eyelids closing, in accordance with embodiments. The eyelids can close with a downward movement 22A of the upper eyelid and an upward movement 22B of the lower eyelid. The closing of the eyelids exerts pressure on the covering 100 such that covering 100 comprises second configuration 100C2. The second configuration 100C2 comprises the sag height 105 decreased to second sag height 105S2 such that the volume of chamber 100C decreases and urges pumped tear fluid 100TL from under the covering. The pumped tear liquid 100TL flows radially outward under the outer portion 120P and through fenestrations 100F such as fenestrations not covered by the eyelid. The pressure of the eyelid can urge the covering 100 toward cornea 10 so as to decrease the volume of chamber 100C. The volume of chamber 100C can decrease substantially when the outer portion 120 comprising flange 120F deflects with elastic deformation. Alternatively or in combination, the outer portion 120 corresponding to the cornea can deflect so as to decrease the volume of chamber 100C. In many embodiments, the inner portion 110 comprising optical component 100A may deflect with pressure of the eyelid so as to decrease the volume of chamber 100C.

Figure 3D:
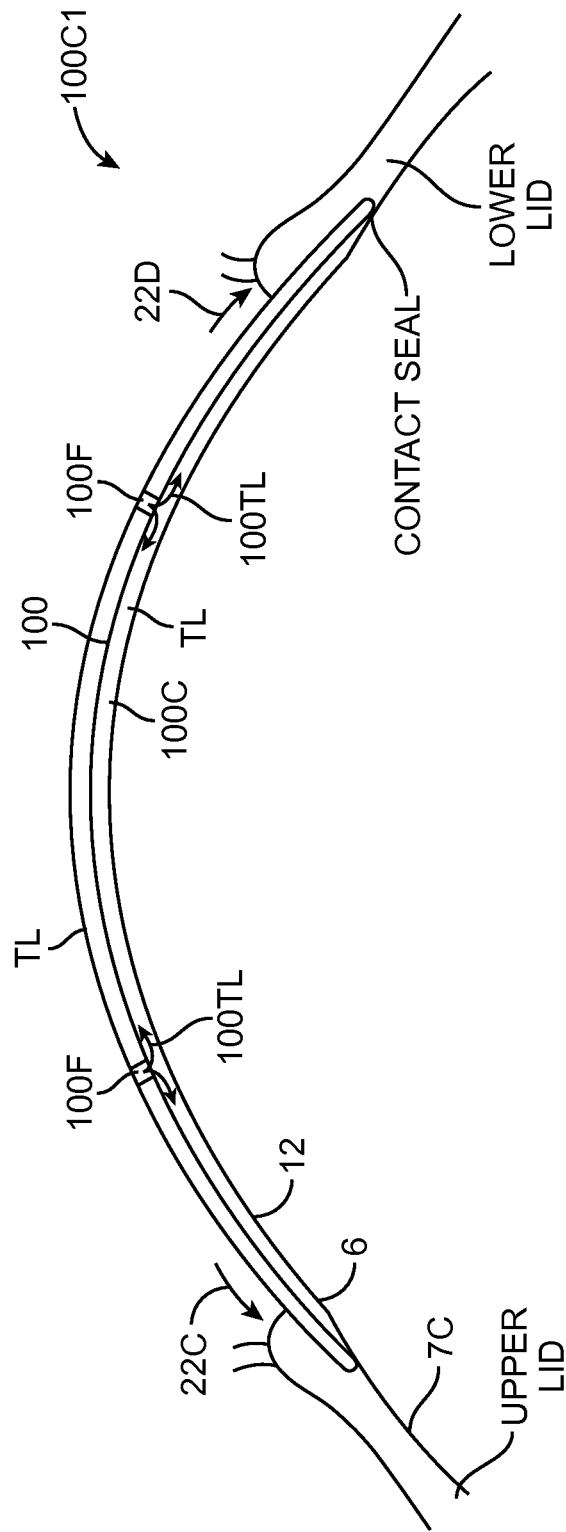
FIG. 3D shows side profile the covering of FIG. 3A with the eyelids opening, in accordance with embodiments of the present invention.

FIG. 3D shows side profile the covering of FIG. 3A with the eyelids opening, in accordance with embodiments of the present invention. When the eyelids retract with upward movement 22C of the upper eyelid and downward movement 22D of the lower eyelid, the covering 100 can return to the first configuration 100C1 having first sag height 105S1, such that the volume of the chamber increases. The outer portion 120 comprising flange 120F and peripheral portion 120P of the sclera coupling portion 130 may contact the conjunctiva so as to form a contact seal with the conjunctiva. The contact seal with the conjunctiva encourages flow of the tear liquid TL through the fenestrations 100F and into the chamber 100C, such that pumped tear liquid 100TL can be located between the cornea and the covering 100.

The tear rivulet of the lower lid can move upward when the eyes close so as to provide tear liquid on the surface of the eye, and at least a portion of the rivulet can couple to the upper lid when the lids contact each other. When the upper lid moves upward with movement 22C and the lower lid moves downward with movement 22D, the upper lid provides tear liquid TL near the upper fenestrations to pass through the upper fenestrations and the lower lid can provide tear liquid TL near the lower fenestrations to move through the lower fenestrations.

Repeated blinking of the eye may occur naturally, so as to pump tear liquid under the covering and rinse the cornea and conjunctiva under the covering. This pumping and rinsing provided by the covering can extend the amount of time the covering can be worn by a patient such as a patient having a normal unablated eye, and may encourage epithelial regenerations in post PRK eyes, for example.

Figure 3E:
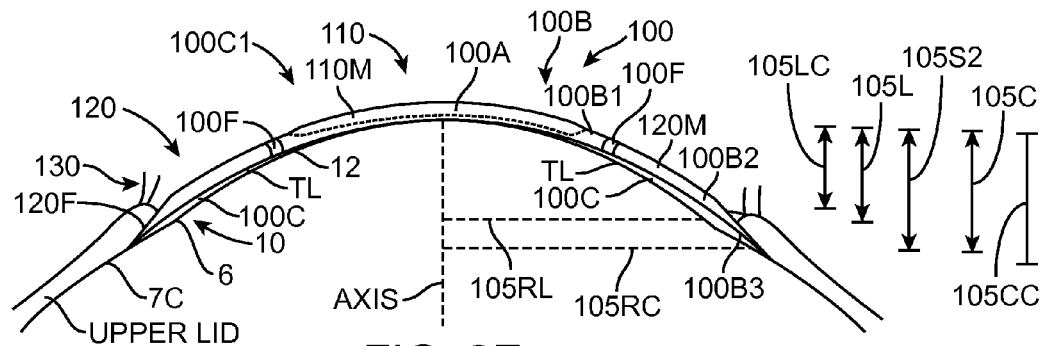
FIG. 3E shows a covering comprising a contact lens placed on the eye such that the covering is supported with an inner portion of the cornea and the conjunctiva with the covering separated from an outer portion of the cornea so as to define a chamber when the eyelids are separated, in accordance with embodiments of the present invention.

FIG. 3E shows a covering comprising a contact lens placed on the eye such that the covering is supported with an inner portion of the cornea and the conjunctiva with the covering separated from an outer portion of the cornea so as to define a chamber when the eyelids are separated, in accordance with embodiments of the present invention. The covering 100 may contact the cornea at an inner portion of the cornea, for example at a central location. The inner portion 110 can be sized to fit the cornea centrally as described herein, for example with on K fitting. The outer portion of the covering 120 comprising flange 120F and sclera coupling portion 130 can be sized to contact the conjunctiva when the inner portion 110 contacts the sclera centrally, such that chamber 100C is formed over the outer portion of the cornea with a gap extending between the outer portion of the cornea and the covering. The outer portion 120 of the covering extending over the outer portion of the cornea may have a curvature less than the cornea, such that the outer portion 120 over the outer portion of the cornea can form chamber 100C when the inner portion 110 is supported with the cornea and the outer portion 120 comprising flange 120F is coupled to the conjunctiva. The fenestrations 100F can be located on the covering to correspond with a location of chamber 100C and the gap when the eyelids are open. The outer portion 120 comprises a resistance to deflection sufficient to form chamber 100C when the eyelids are open and insufficient to resist deflection when the eyelids close and move over the outer portion such that the outer portion moves toward the cornea and decrease the gap distance when the eyelids at least partially cover the outer portion 120.

The covering 100 can be fit to the cornea to encourage formation of the chamber 100C and such that covering 100 comprises an initial configuration 100C1 with chamber 100C formed beneath. The cornea may comprise a limbus sag height 105L corresponding to an elevational distance extending from a vertex of the cornea to the limbus. The limbus may be located a radial distance 105RL from a measurement axis of the eye. The eye may comprise a conjunctiva sag height 105C at a radial distance 105RC from the axis of the eye. The covering may comprise a limbus sag height 105LC at a location corresponding to the radial distance 105RL to the limbus. The covering may comprise a conjunctiva sag height 105CC at a conjunctiva contacting location corresponding to the radial distance 105RC of the conjunctiva, for example along flange 120F. In many embodiments, the sag height 105LC of the covering at the location corresponding to the limbus is no more than the limbus sag height 105L, and the sag height 105CC of the covering at the location corresponding to the conjunctiva is no more than the conjunctiva sag height 105C, such that pressure to the limbus is decreased. When the covering is placed on the eye, the conjunctiva coupling portion 130 comprising flange portion 120F can deflect such that the sag height of the conjunctiva contacting portion is decreased from 105CC the sag height of the conjunctiva to the sag height of the conjunctiva 105C, such that the sag height of the covering comprises a sag deflected sag height 105S2.

Figure 3F:
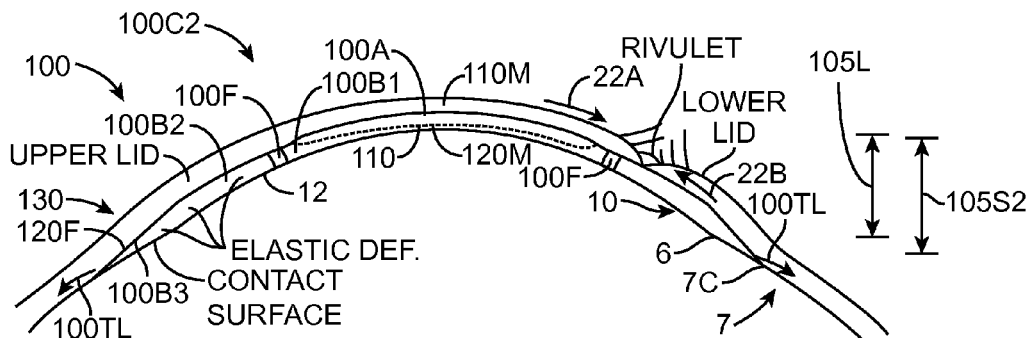
FIG. 3F shows a side sectional view of the covering of FIG. 3E with the eyelids closing, in accordance with embodiments of the present invention.

FIG. 3F shows a side sectional view of the covering of FIG. 2E with the eyelids closing such that covering 100 comprises a configuration 100C2 with chamber 100C having a decreased volume. When the eyelids close, the upper and lower lids exert pressure on the covering such that the covering is urged toward the outer portion of cornea and the conjunctiva. The outer portion of the covering over the outer portion of the cornea may not have sufficient resistance to deflection such that the outer portion of the covering is deflected downward toward the outer portion of the cornea. The gap distance extending between the outer portion of the covering over the outer portion of the cornea is decreased, such that the volume of chamber 100C decreases and pumped tear liquid 100TL flow from chamber 100C through fenestrations 100F and under the conjunctiva contacting portion 130 comprising flange portion 120F. The upper eyelid can extend across the pupil so as to cover inferior and superior fenestrations 100F. The upper eyelid may contact the lower eyelid so as to draw the tear liquid of the rivulet superiorly when the eye opens, such that tear liquid of the rivulet can be drawn into the chamber through the inferior and superior fenestrations.

The deflection of the outer portion of the covering over the outer portion of the cornea can be provided with a covering having a relative rigidity within a range from about 1.0E-6 $Pa*m^3$ to about 6E-4 $Pa*m^3$, for example from about 2.5E-6 $Pa*m^3$ to about 5E-4 $Pa*m^3$. Table A2 shows values suitable of relative rigidity and corresponding ranges of outer portion 120 corresponding to the outer portion of the cornea that can be determined based on the teachings described herein so as to determine the relative rigidity of the outer portion of the covering to provide resistance to deflection and form the chamber with the gap when the eyelid is away from the portion of the covering and so as to deflect toward the cornea and decrease the gap and corresponding chamber volume when the eyelid covers the portion of the covering.

The deflection of the sclera contacting portion 130 to couple to the conjunctiva can be provided with the sclera contacting portion 130 comprising a relative rigidity of no more than about 2E-4 $Pa*m^3$, for example no more than about 1E-4 $Pa*m^3$, and in many embodiments no more than about 2E-5 $Pa*m^3$. Table A2 shows values suitable of relative rigidity and corresponding ranges of sclera coupling portion 130 that can be determined based on the teachings described herein so as to determine the relative rigidity of the sclera coupling portion of the covering to provide resistance to deflection and form the chamber with the gap when the eyelid is away from the portion of the covering and so as to deflect toward the cornea and decrease the gap and corresponding chamber volume when the eyelid covers the outer portion of the covering over the outer portion of the cornea.

The deflection of the flange portion 120F to couple to the conjunctiva can be provided with the flange portion 130 comprising a relative rigidity of no more than about 1E-4 Pa*m^3, for example no more than about 2E-5 Pa*m^3, and in many embodiments no more than about 2.5E-6 Pa*m^3. Table A2 shows values suitable of relative rigidity and corresponding ranges of outer flange portion 120F that can be determined based on the teachings described herein so as to determine the relative rigidity of the flange portion 120F of the covering to provide resistance to deflection and form the chamber with the gap when the eyelid is away from the portion of the covering and so as to deflect toward the cornea and decrease the gap and corresponding chamber volume when the eyelid covers the outer portion of the covering over the outer portion of the cornea.

FIG. 3F1 shows a side sectional view of the covering of FIG. 3F with rotation of the eye when the lids close such that sliding of the covering along the epithelium is inhibited when tear liquid is pumped, in accordance with embodiments of the present invention. The axis of the eye can rotate superiorly such that the covering slides along the upper lid and the lower lid. The axis of the eye may comprise one or more known axis of the eye and can be determined in many ways by a person of ordinary skill in the art.

Figure 3G:
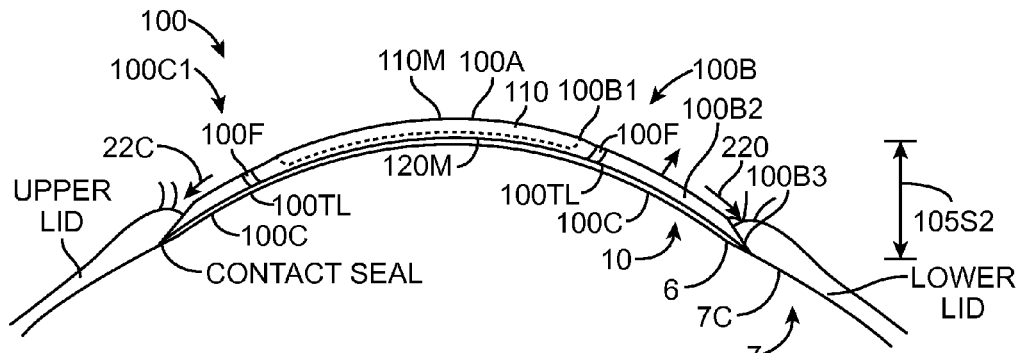
FIG. 3G shows a side sectional view of the covering of FIG. 3E with the eyelids opening, in accordance with embodiments of the present invention.

FIG. 3G shows a side view sectional view of the covering of FIG. 3E with the eyelids opening, in accordance with embodiments of the present invention. The opening of the eyelids decreases pressure and allows the outer portion of the covering above the outer portion of the cornea to move away from the cornea. The tear liquid TL may pass through fenestrations 100F and into the chamber 100C. The outer portion of the covering comprising portion 130 and flange 120F can contact the conjunctiva to inhibit tear flow and may seal the covering.

Figure 3H:
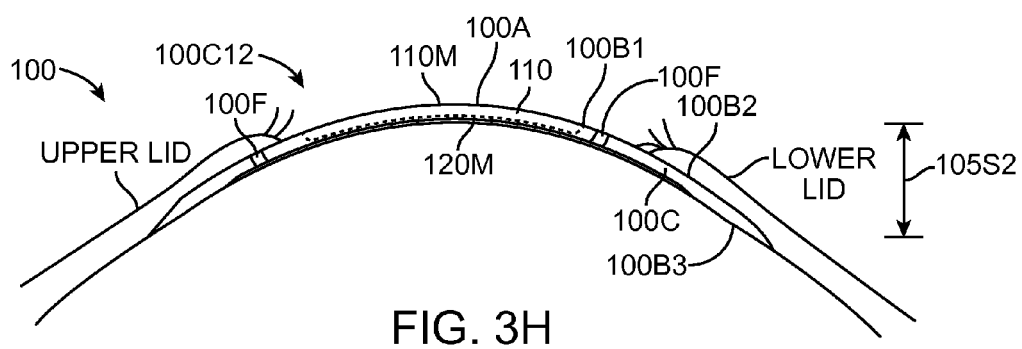
FIG. 3H shows a side sectional view of the covering of FIG. 3E with the eyelids located at an intermediate location such that the chamber comprises an intermediate volume, in accordance with embodiments of the present invention.

FIG. 3H shows a side view sectional view of the covering of FIG. 3E with the eyelids located at an intermediate location such that the chamber comprises an intermediate configuration 100C12 volume, in accordance with embodiments. The optical component 100A comprising inner portion 110 may comprise sufficient rigidity and resistance to deflection so as to provide vision for the patient when the covering comprises intermediate portion 100C12 having outer portion 120 deflected so as to decrease volume of chamber 100C. For example, the patient can close the eyelids to the pupil margin to deflect the outer portion and the optical component 100A and inner portion 110 can remain substantially undeflected such that the patient can have vision of 20/20 or better (metric 6/6 or better) with a portion of one or more eye lids contacting the inner portion 110. Opening of the eyelids can increase the chamber volume and pump tear liquid and closing of the eyelids can decrease chamber volume and pump tear liquid.

Figure 3I:
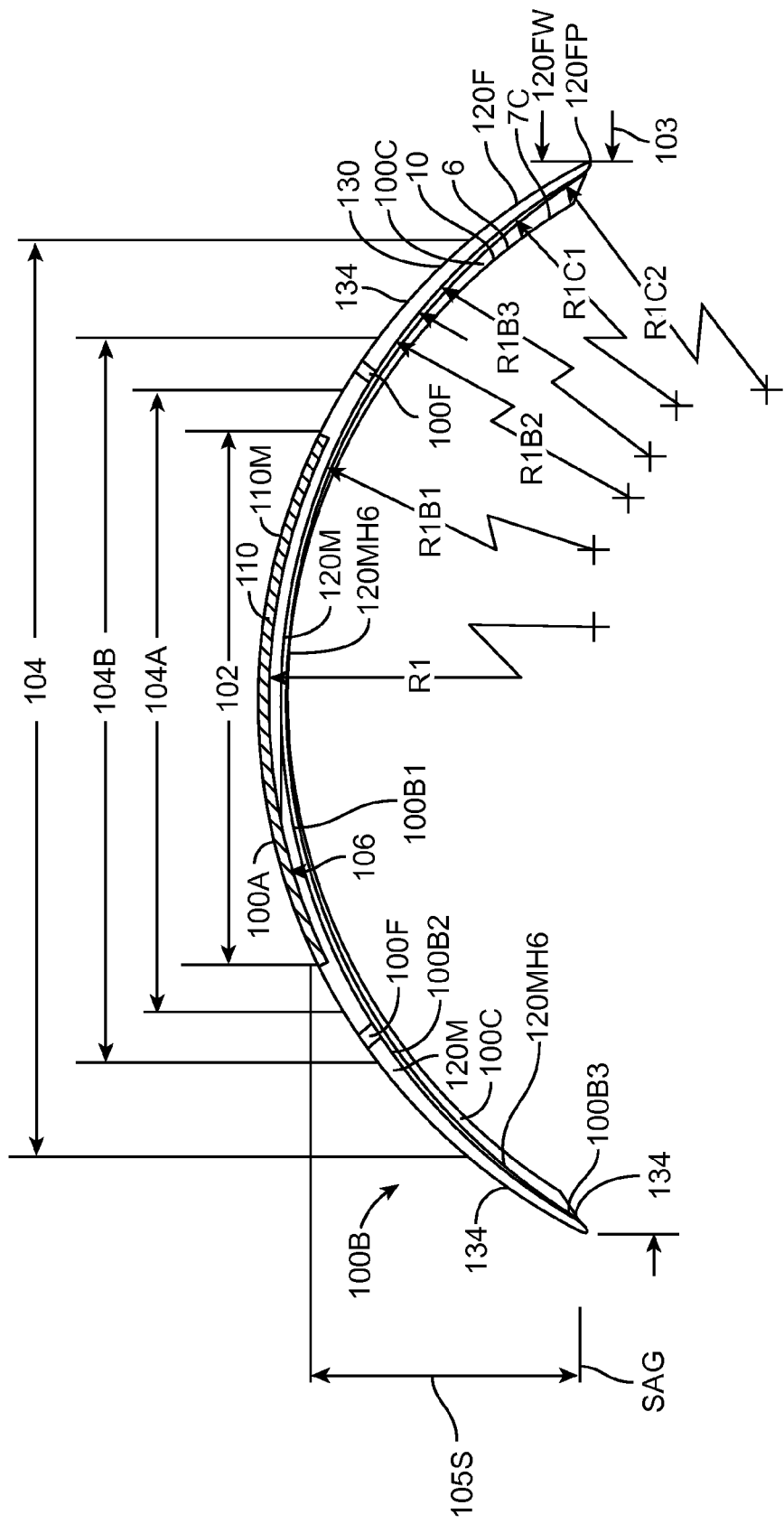
FIG. 3I shows a side sectional view of the covering of FIG. 1C4 placed on the eye with hydrogel contacting the eye, in accordance with embodiments of the present invention.

FIG. 3I shows a side view sectional view of the covering of FIG. 1C4 placed on the eye with hydrogel contacting the eye. The covering 100 comprises the layer of hydrogel material 120MHG extending along the posterior surface of the covering so as to contact the eye with at least a portion of the hydrogel layer. The covering 100 can be dimensioned to form chamber 100C defined at least in part with the layer of hydrogel material. The fenestration may extend through the hydrogel layer so as to provide pumping as described herein. Alternatively or in combination, the posterior end of the fenestration can be covered with the hydrogel material to couple the cornea to the fenestration with the layer of hydrogel material. The fenestrations covered with the layer of hydrogel material 120MHG can be located along the deflectable portion of the covering so as to encourage movement of water and therapeutic agents along the hydrogel material, for example when the eye blinks. The hydrogel layer may comprise a medium to pass liquid and therapeutic agent from the fenestration to a desired location of the cornea, for example with wicking of the liquid and therapeutic agent to a central location of the cornea. The covering comprising the hydrogel layer extending along the lower surface as described herein can be fit to an unablated eye to provide refractive correction or fit to an ablated eye as described herein.

Clinical testing in accordance with embodiments has shown that the curved portions of the covering can be fit with on K-values in accordance with corneal curvatures and sag heights and limbus sag heights and conjunctiva sag heights of a patient population.

Appendix I shown herein below provides dimensions and fit parameters for covering 100 in accordance with embodiments and teachings as described herein. The coverings may comprise one or more of the materials in the A series Tables shown herein, for example. The dimensions and fit parameters of the coverings can provide pumping of the tear liquid when placed on the cornea in accordance with embodiments described herein. The tables of Appendix I identify the coverings for use with steep K corneas, medium K corneas and flat K corneas, for example. The K values listed can be based on population norms, such that the coverings provide pumping as described herein when placed on the eye. The coverings can be used with non-ablated eyes or ablated eyes, and the covering can be identified at least in part based on the first inner curvature R1.

Table B1 shows covering 100 having a diameter of approximately 14 mm across and can be fit on K or flatter, for example as described herein. The table lists R1 corresponding to the center ablated portion of the cornea. The inner portion 110 comprising optical component 100A and inner coupling component 100B1 has dimension R1 extends about 5 mm across, and the ablation zone can be larger, for example about 6 mm. The portion corresponding to radius R1B1 has dimensions of about 5-7 mm across, and the curvature can be expressed with keratometry values (K-values) corresponding to the optical power of the eye in Diopters (D). The portion corresponding to radius R1B2 has dimensions of about 7-9 mm across. The portion corresponding to radius R1B3 has dimensions of about 9-11 mm across. The portion corresponding to R1C1 can extend from about 11 to 13.5 mm across, and may comprise curvature having one or more values between portion R1B3 and portion R1C2, for example a radius of curvature between about 8 mm and about 12 mm such as about 10 mm. The portion corresponding to R1C2 can extend from about 13.5 to 14 mm across. The sag height of the portion R1C2 can be from about 3.1 to about 3.4 mm, for example. The portion corresponding to R1C1 can be fit to the cornea in many ways as described herein, for example with the tangent of portion R1C1 aligned with R1B3 on the inner boundary and R1C2 along an outer boundary so as to inhibit ridge formation as described herein.

Table B2 shows covering 100 having a diameter of approximately 14 mm across and can be fit on K or flatter, for example as described herein. The table lists R1 corresponding to the center ablated portion of the cornea. The inner portion 110 comprising optical component 100A and inner coupling component 100B1 has dimension R1 extends about 5 mm across, and the ablation zone can be larger, for example about 6 mm. The portion corresponding to radius R1B1 has dimensions of about 5-7 mm across, and the curvature can be expressed with keratometry values (K-values) corresponding to the optical power of the eye in Diopters (D). The portion corresponding to radius R1B2 has dimensions of about 7-9 mm across. The portion corresponding to radius R1B3 has dimensions of about 9-11 mm across, and these values range from about 35.75 to about 40, such that each value is somewhat flatter at the peripheral portion than corresponding values of Table B1. For example, Table B1 lists the values for R1B3 as having a range from about 36.75 to about 41D. The portion corresponding to R1C1 can extend from about 11 to 13.5 mm across. The portion corresponding to R1C2 can extend from about 13.5 to 14 mm across. The sag height of the portion R1C2 can be from about 3.1 to about 3.4 mm, for example. The portion corresponding to R1C1 can be fit to the cornea in many ways as described herein, for example with the tangent of portion R1C1 aligned with R1B3 on the inner boundary and R1C2 along an outer boundary so as to inhibit ridge formation as described herein.

Table B3 shows covering 100 having a diameter of approximately 16 mm across and can be fit on K or flatter, for example as described herein. The table lists R1 corresponding to the center ablated portion of the cornea. The inner portion 110 comprising optical component 100A and inner coupling component 100B1 has dimension R1 extends about 5 mm across, and the ablation zone can be larger, for example about 6 mm. The portion corresponding to radius R1B1 has dimensions of about 5-7 mm across, and the curvature can be expressed with keratometry values (K-values) corresponding to the optical power of the eye in Diopters (D). The portion corresponding to radius R1B2 has dimensions of about 7-9 mm across. The portion corresponding to radius R1B3 has dimensions of about 9-105 mm across, and these values range from about 36.75 to about 41. The portion corresponding to R1C can extend from about 13 to about 16 mm across. The sag height of the portion R1C2 can be less than about 3.6 mm, for example, such that portion R1C2 can be deflected when placed on the eye. The portion corresponding to R1C1 can be fit to the cornea in many ways as described herein.

Table B4 shows covering 100 having curvatures for use with non-ablated eyes so as to pump tear liquid as described herein, for example with an extended wear contact lens. Covering 100 has a diameter of approximately 14 mm across and can be fit on K or flatter, for example as described herein. The table lists R1 corresponding to the center ablated portion of the cornea. The inner portion 110 comprising optical component 100A and inner coupling component 100B1 has dimension R1 extends about 5 mm across. The curvatures of the inner portion corresponding to R1 have curvature values corresponding to optical powers from about 39 D to about 48D, which can be based on population data for unablated eyes and combined with the curvatures for portions R1B1 to R1B3 and R1C1 and R1C2, for example. The portion corresponding to radius R1B1 has dimensions of about 5-7 mm across, and the curvature can be expressed with keratometry values (K-values) corresponding to the optical power of the eye in Diopters (D). The portion corresponding to radius R1B2 has dimensions of about 7-9 mm across. The portion corresponding to radius R1B3 has dimensions of about 9-11 mm across. The portion corresponding to R1C1 can extend from about 11 to about 13.5 mm across. The portion corresponding to R1C2 can extend from about 13.5 to 14 mm across. The sag height of the portion R1C2 can be from about 3.1 to about 3.4 mm, for example. The portion corresponding to R1C1 can be fit to the cornea in many ways as described herein, for example with the tangent of portion R1C1 aligned with R1B3 on the inner boundary and R1C2 along an outer boundary so as to inhibit ridge formation as described herein.

Although Tables B1-B4 list specific curvature values by way of example, a person of ordinary skill in the art can determine many curvature values based on the teachings and embodiments described herein and one or more of the curvatures can be combined with an aspheric surface, for example an aspheric surface having a conic constant.

Methods and Apparatus to Identify Coverings for Eye Treatment

FIG. 4 shows apparatus 200 and a plurality 208 of coverings to treat an eye. The apparatus 200 comprises a cornea and sclera eye measurement system 202, a wavefront measurement system, a laser ablation system 204, a topography measurement system 205, a user device 206 and the plurality of coverings 208.

The plurality of coverings 208 may comprise coverings 100 as described herein or commercially available coverings identified based on the teachings as described herein. The plurality of coverings 208 may comprise an inventory of coverings comprising a first covering, a second covering, a third covering, and up to an Nth covering.

The sclera measurement system 202 may comprise a processor having a computer readable memory and communication circuitry. The sclera measurement system may measure the conjunctiva over the sclera, and may measure the cornea when the sclera is measured. The cornea and sclera measurement system 202 may comprise a system to measure the cornea and the sclera to determine the shape of the covering to fit the eye. The cornea and sclera measurement system 202 may comprise components of a fluorescence topography based system for example components of the system commercially available from PAR technologies. The system may be modified so as to measure at least about 14 mm across the conjunctiva, sclera and cornea, for example.

The laser ablation system 204 may comprise a processor having a computer readable memory and communication circuitry, and may comprise a components of a commercially available excimer laser ablation system available from such as the Wavelight Allegretto Wave Eye-Q laser ablation system commercially available from Alcon, the Technolas laser ablation system commercially from Bausch and Lomb, the Star laser ablation system commercially available from Abbott Medical Optics, or the MEL laser ablation system commercially available from Meditech, for example.

The corneal topography measurement system 205 may comprise a processor having a computer readable memory and communication circuitry. The corneal topography measurement system 205 may comprise one or more of a Placido ring based system, a Scheimpflug imaging based system, or a florescence topography based system, for example. The corneal topography measurement system may comprise a commercially available Placido Ring based system: such as Orbscan™, Atlas™, Keratron™, TMS™, Magellan™, iTrace™ or a Pentacam™, for example. The corneal topography system may comprise as Scheimpflug system: such as the commercially available Pentacam™ and Galilei™. The commercially available corneal topography based system may comprise a fluorescence topography system such as the PAR corneal topography system.

The user communication device 206 may comprise a processor having a computer readable memory, communication circuitry and a display, for example a personal digital assistance such as an iPhone™, an iPad™, a Blackberry™, a tablet PC. The plurality of coverings 208 may comprise a first covering 100, a second covering 100 and an Nth covering 100, for example a 10th covering 100. The plurality of coverings may comprise an inventory of coverings having shape profiles, sizes, moduli and rigidity so as to treat the eye as described herein.

The eye measurement system may measure the eye from the cornea to the sclera to identify the covering, for example based on curvature of the sclera, curvature of the cornea, and curvature of the ablated portion of the cornea.

The above systems and components can be interchanged and combined in many ways. For example, the sclera measurement system can be used to measure the topography of the cornea to fit the covering 100. The laser ablation system 204 may be combined with one or more measurement systems. For example, the Orbscan Placido ring based system may be combined with a Technolas laser ablation system and the Zyoptix wavefront measurement system, each available from Bausch and Lomb. The commercially available STAR™ excimer laser ablation system may be combined with a WaveScan™ wavefront measurement system, both available from Abbot Medical Optics. The commercially available MEL laser ablation system may be combined with the Atlas Placido topography system, for example commercially available form Zeiss Meditec. The wavefront system and refraction measurement system may comprise a combined Hartmann Shack topography and wavefront system, or a full gradient topography system, for example as is commercially available from Wavefront Sciences, Inc.

Figure 4A:
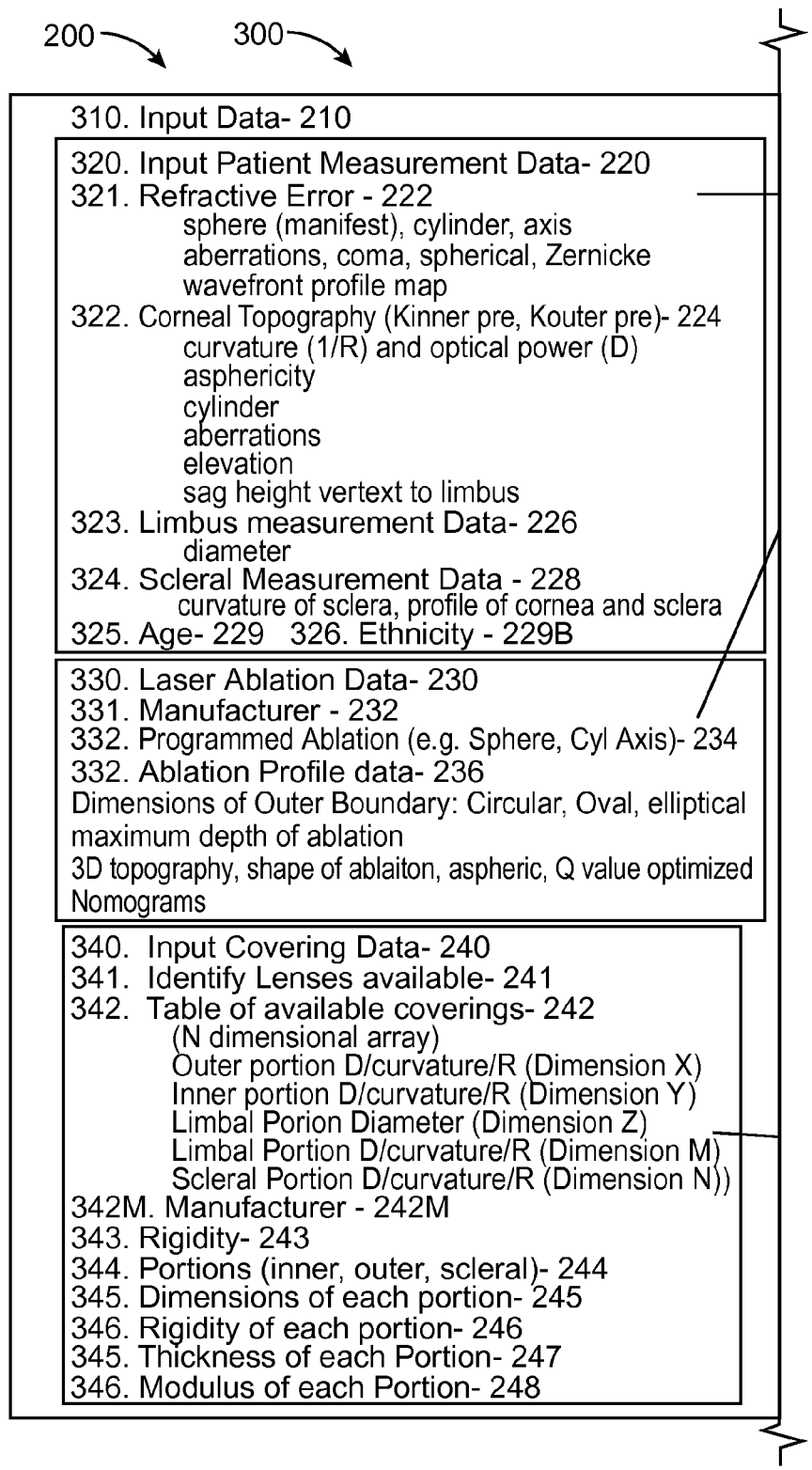
FIG. 4A shows data structures and a method of identifying a covering, in accordance with embodiments of the present invention.
Figure 4A:
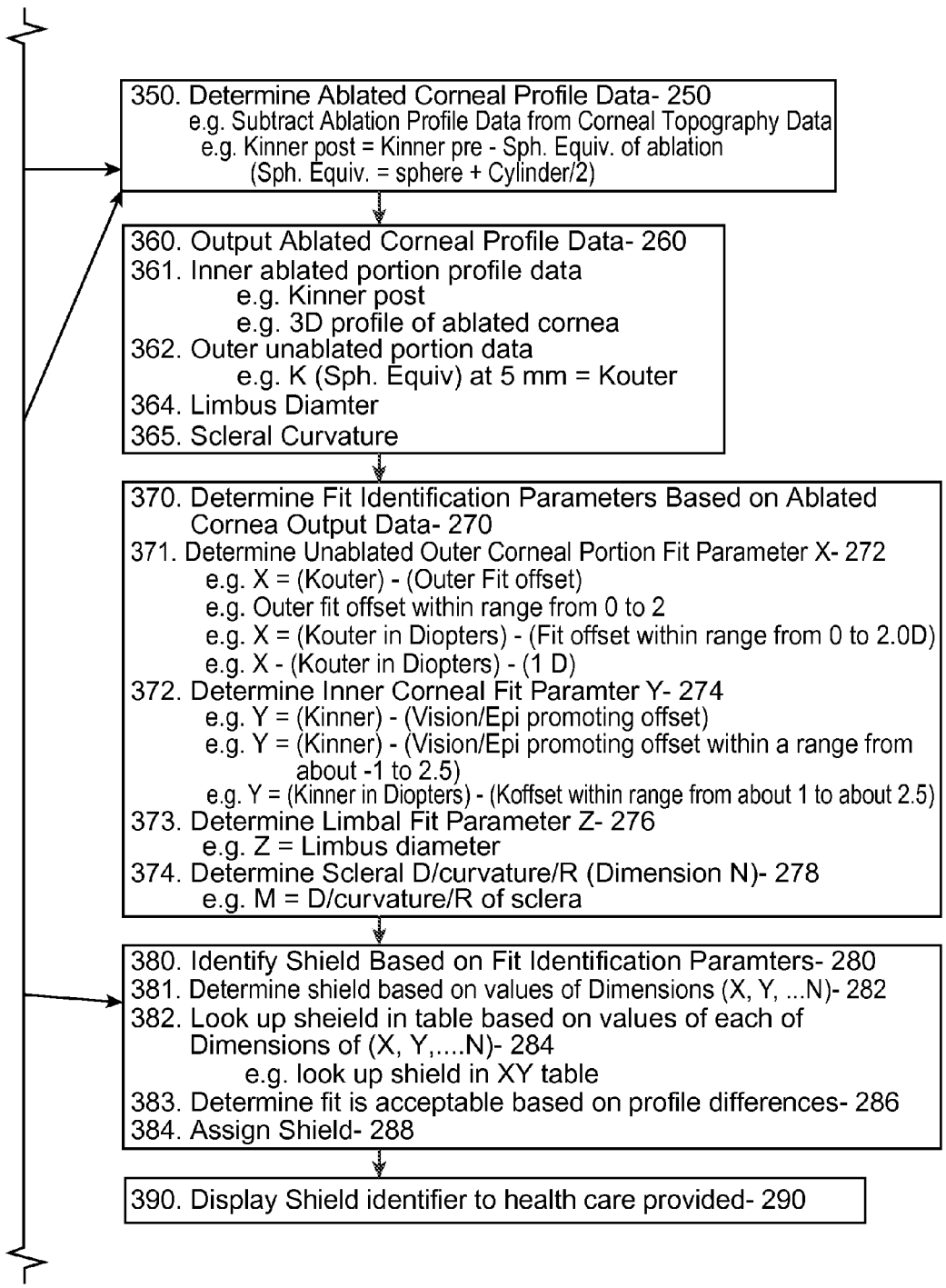

FIG. 4A shows data structures 200 and a method 300 of identifying a covering. The data structures 200 may comprise data structures of one or more of the system 202, the system 204, the device 206, for example, and may comprise data structures of a distributed processor system.

A step 310 inputs data 210
A step 320 inputs patient measurement data 220
A step 321 determines refractive error 222. The refractive error 222 may comprise one or more of:
 sphere (manifest), cylinder, axis
 aberrations, coma, spherical, Zernicke
 wavefront profile map
A step 322 measures corneal topography (Kinner pre, Kouter pre) 224. The corneal topography data 224 may comprise one or more of:
 curvature (1/R) and optical power (D)
 asphericity
 cylinder
 aberrations
 elevation
 sag height corneal vertex to limbus to sclera
A step 323 measure limbus measurement data 226. The data 226 may comprise one or more of:
 A diameter or a sag height of the limbus, for example the sag height and diameter of the limbus
A step 324 measures scleral measurement data 228. The data 228 may comprise one or more of:
 curvature of sclera, a sag height of the sclera at an axial location, or an angle of the sclera at the axial location, for example a sag height where an outer portion of the covering 100 contacts the sclera.
A step 325 determines age data 229 and ethnicity data 229B, for example corresponding to eye color and size and pupil size
A step 330 determines laser ablation data—230. The laser ablation data 230 may comprise one or more of:
manufacturer 232 determined with a step 331;
programmed ablation (e.g. sphere, cylinder & axis) 234 determined with step 332; and
ablation profile data 236 determined with step 332.
 The ablation profile data may comprise one or more of:
 dimensions of outer Boundary
 circular, oval, elliptical
 maximum depth of ablation
 3D topography shape of ablation
 a Q value for an optimized aspheric ablation
 a physician nomogram, for example to adjust ablation depth
A step 340 determines input covering data—240
A step 341 identifies available coverings 241
A step 342 provides a Table of available coverings—242. The table 242 may comprise one or more of:
 (N dimensional array);
 outer portion D/curvature/R (Dimension X);
 inner portion D/curvature/R (Dimension Y);
 limbal portion diameter (Dimension Z);
 limbal portion D/cuvature/R (Dimension M);
 scleral portion D/curvature/R (Dimension N);
A step 342M determines Manufacturer—242M
A step 343 determines rigidity—243
A step 344 determines Portions (inner, outer, scleral)—244
A step 345 determines Dimensions of each portion—245
A step 346 determines Rigidity of each portion—246
A step 345 determines Thickness of each Portion—247
A step 346 determines Modulus of each Portion—248
A step 350 determines Ablated Corneal Profile Data—250. The data 250 may comprise one or more of:
 e.g. Subtract Ablation Profile Data from Corneal Topography Data
 e.g. Kinner post=Kinner pre−Sph. Equiv. of ablation (Sph. Equiv.=Sphere+Cylinder/2)
A step 360 outputs Ablated Corneal Profile Data—260
A person of ordinary skill in the art will recognize that steps 350 and 360 may not be necessary when the cornea comprises an unablated cornea. Alternatively or in combination, the ablation profile can be set to zero to determine the covering for a non-ablated cornea.
A step 361 determines Inner ablated portion profile data may comprise one or more of:
 e g Kinner post
 e.g. 3D profile of ablated cornea
A step 362 determines outer unablated portion data
 e.g. K (Sph. Equiv) at 5 mm=Kouter
A step 364 provides one or more of the Limbus Diameter or the limbus sag height
A step 365 provides one or more of the Scleral Curvature or the scleral sag height at an axial location of the sclera, for example.
A step 370 determines fit identification parameters based on cornea output data 270
The cornea output data may comprise fit profiles for an unablated cornea such as a cornea to receive an extended wear contact lens for refractive correction, or fit profiles for an ablated cornea such as a cornea receiving a PRK ablation, or combinations thereof.
A step 371 Determines Unablated Outer Corneal Portion Fit Parameter X—272. The parameter 272 may comprise one or more of:
 e.g. X=(Kouter)−(Outer Fit offset)
 e.g. Outer fit offset within range from 0 to 2
 e.g. X=(Kouter in Diopters)−(Fit offset within range from 0 to 2.0D)
 e.g. X−(Kouter in Diopters)−(1D)
A step 372. Determine Inner Corneal Fit Parameter Y—274. The parameter 274 may comprise one or more of:
 e.g. Y=(Kinner)−(Vision/Epi promoting offset)
 e.g. Y=(Kinner)−(Vision/Epi promoting offset within a range from about −1 to 2.5)
 e.g. Y=(Kinner in Diopters)−(Koffset within range from about 1 to about 2.5)
A step 373 Determines a Limbal Fit Parameter Z-276, such as
 e.g. Z=Limbus diameter or sag height or combinations thereof.
A step 374 Determines Scleral D/curvature/R (Dimension N)—278, such as
 e.g. M=D/curvature/R of sclera or sag height of the sclera at an axial location or a combination thereof.
A step 380 identifies a Shield Based on Fit Identification Parameters—280. The identification of the shield covering can be based on the fit identification parameters and the array of data comprising the table of available coverings 242.

A step 381 Determines shield based on values of Dimensions (X, Y, . . . N)—282

A step 382 Looks up shield identifier in table based on values of each of Dimensions of (X, Y, . . . N)—284, such as e.g. look up shield in XY table A step 383 Determines when fit is acceptable based on profile differences—286

A step 384 Assigns Shield—288

A step 390 Displays shield identifier to health care provided—290

Table I. shows a look up table in accordance with embodiments. The look up table comprises a unique identifier.

TABLE I

Look Up Table for Shield 100

| Y | X = Outer power 38-40D | X = Outer power 38-40D | X = Outer power 38-40D | X = Outer power 38-40D |
|---|---|---|---|---|
| Y = Inner Power 36-38D | A1 | B1 | C1 | D1 |
| Y = Inner power 38-40D | A2 | B2 | C2 | D2 |
| Y = Inner Power 40-42D | A3 | B3 | C3 | D3 |
| Y = Inner power 42-44D | A4 | B4 | C4 | D4 |

The method 300 can be performed separately from the structures 200.

Figure 4B:
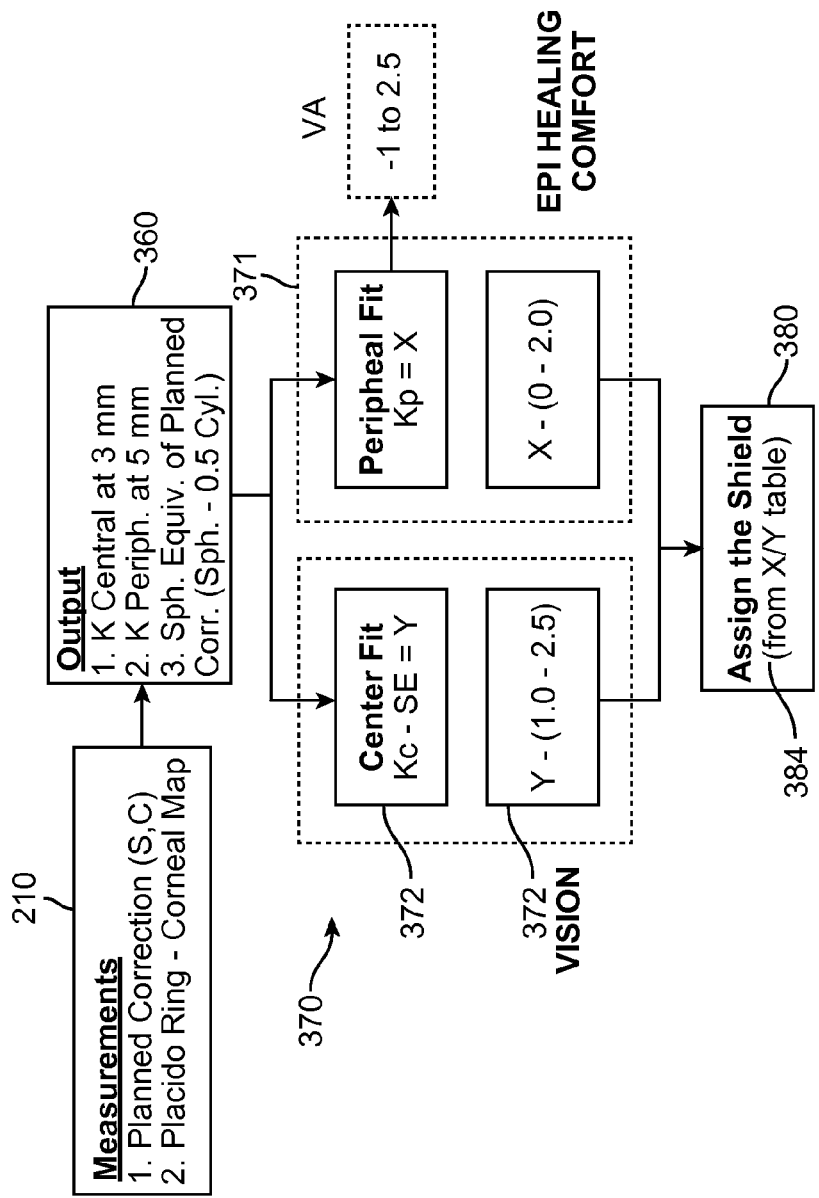
FIG. 4B shows data structures and the method of identifying the covering as FIG. 4A, in which the fit parameters comprise a two fit parameters and the data array comprises a two dimensional look up table, in accordance with embodiments of the present invention.

FIG. 4B shows data structures and the method of identifying the covering as FIG. 4A, in which the fit parameters comprise a two fit parameters and the data array comprises a two dimensional look up table. The K's of FIG. 4B refer to the optical power of the cornea in Diopters (D).

It should be appreciated that the specific steps illustrated in FIGS. 4A and 4B provide a particular method of identifying a covering, according to embodiments of the present invention. Other sequences of steps may also be performed according to alternative embodiments. For example, alternative embodiments of the present invention may perform the steps outlined above in a different order. Moreover, the individual steps illustrated in FIGS. 4A and 4B may include multiple sub-steps that may be performed in various sequences as appropriate to the individual step. Furthermore, additional steps may be added or removed depending on the particular applications. One of ordinary skill in the art would recognize many variations, modifications, and alternatives.

Tables A to C show tables and data structures suitable for incorporation with data structures 200 and method 300. The tables of Appendix I show similar data structures for a plurality of coverings listed in the tables that can be identified similarly.

TABLE A

Table A shows a screening log having a plurality of patients and a covering identified for each eye of each patient, in accordance with embodiments.

| Screening Log | | | Pre-op center K | Mid K | |
|---|---|---|---|---|---|
| Subject ID | Sphere | Cylinder | (D) | (D) | SHIELD CODE |
| EMT OD | −1.25 | −0.5 | 42.9 | 42.2 | DZ |
| EMT OS | −1.25 | −0.5 | 42.0 | 41.7 | DZ |
| AEC OD | −1.75 | −1.50 | 44.0 | 43.4 | EC |
| AEC OS | −1.25 | −0.25 | 43.5 | 43.0 | EC |
| JML OD | −2.25 | −1 | 43.4 | 42.9 | DZ |
| JML OS | −2.25 | −0.5 | 43.4 | 43.1 | EA |
| EGT OD | −1.50 | −0.75 | 43.7 | 43.4 | EC |
| EGT OS | −2.00 | −0.25 | 44.6 | 44.0 | EC |
| REC OD | −2.75 | −0.5 | 44.3 | 43.8 | EA |
| REC OS | −2.50 | −0.5 | 44.2 | 43.8 | EA |
| JGG OD | −1.00 | −0.75 | 42.6 | 42.4 | DZ |
| JGG OS | −1.50 | −1 | 42.5 | 42.3 | DZ |
| NGT OD | −2.50 | −1.25 | 44.5 | 43.7 | EA |
| NGT OS | −3.00 | −1.25 | 44.1 | 43.5 | DY |
| DCG OD | −0.75 | −0.5 | 43.8 | 43.4 | EF |
| DCG OS | −1.25 | 0 | 43.9 | 43.6 | EF |
| JRJ OD | −2.50 | 0 | 44.1 | 43.6 | EC |
| JRJ OS | −2.00 | 0 | 43.6 | 43.1 | EC |
| REC OD | −2.75 | −0.5 | 44.3 | 43.8 | EA |
| REC OS | −2.50 | −0.5 | 44.2 | 43.8 | EA |
| DLL OD | −2.75 | −0.5 | 44.1 | 43.8 | EA |
| DLL OS | −2.75 | 0 | 45.0 | 44.5 | ED |

Table A shows: a subject ID; eye (OD or OS): refraction including sphere, cylinder: pre-op K(D) in spherical equivalents for the inner portion; Mid K in spherical equivalents in the outer portion; and the corresponding shield code comprising the unique identifier corresponding the covering that fits the patient. For patient EMT OD, the refraction is −1.25 sph, −0.5 cyl, the pre-op center K is 42.9 D and the mid periphery K is 42.2 D, such that the identified shield code is DZ. If a patient cannot be fit, a code "not a candidate" can be assigned and no covering is provided for the patient.

Table B comprises an array of data to identify a covering for the eye from among a plurality of coverings, and the properties for a plurality of coverings and the corresponding properties of each covering 100 of the plurality. As used herein, a covering encompasses a shield, and corresponding unique identifier can also be referred to herein as a code.

| SHIELD | Center/Inner Portion Curve | | Mid/Outer Portion Curve | | Center Fitting Range (−1.00 to −2.00) | | Mid-Peripheral/ Outer Portion Fitting Range (0 to −1.50) | |
|---|---|---|---|---|---|---|---|---|
| UNIQUE | R1 | Center/INNER | R1B | | | | | |
| ID Code | Center (mm) | OPTICAL POWER (D) | Mid (mm) | Mid (D) | min (D) | max (D) | min (D) | max (D) |
| DV | 9.0 | 37.5 | 8.1 | 41.5 | 38.50 | 39.50 | 41.50 | 43.00 |
| DW | 9.0 | 37.5 | 7.8 | 43.0 | 38.50 | 39.50 | 43.00 | 44.50 |

-continued

| SHIELD UNIQUE ID Code | Center/Inner Portion Curve | | Mid/Outer Portion Curve | | Center Fitting Range (−1.00 to −2.00) | | Mid-Peripheral/ Outer Portion Fitting Range (0 to −1.50) | |
|---|---|---|---|---|---|---|---|---|
| | R1 Center (mm) | Center/INNER OPTICAL POWER (D) | R1B Mid (mm) | Mid (D) | min (D) | max (D) | min (D) | max (D) |
| DX | 8.8 | 38.5 | 8.1 | 41.5 | 39.50 | 40.50 | 41.50 | 43.00 |
| DY | 8.8 | 38.5 | 7.8 | 43.0 | 39.50 | 40.50 | 43.00 | 44.50 |
| DZ | 8.5 | 39.5 | 8.1 | 41.5 | 40.50 | 41.50 | 41.50 | 43.00 |
| EA | 8.5 | 39.5 | 7.8 | 43.0 | 40.50 | 41.50 | 43.00 | 44.50 |
| EB | 8.5 | 39.5 | 7.6 | 44.5 | 40.50 | 41.50 | 44.50 | 46.00 |
| EC | 8.3 | 40.5 | 7.8 | 43.0 | 41.50 | 42.50 | 43.00 | 44.50 |
| ED | 8.3 | 40.5 | 7.6 | 44.5 | 41.50 | 42.50 | 44.50 | 46.00 |
| EF | 8.1 | 41.5 | 7.8 | 43.0 | 42.50 | 43.50 | 43.00 | 44.50 |
| EG | 8.1 | 41.5 | 7.6 | 44.5 | 42.50 | 43.50 | 44.50 | 46.00 |
| EG | 8.1 | 41.5 | 7.6 | 44.5 | 42.50 | 43.50 | 44.50 | 46.00 |

As shown in Table B, the plurality of coverings has an inner radius of curvature R1 corresponding to the inner portion 110, and an outer radius of curvature R1B corresponding to an outer portion 120 of the covering. The radius of curvature R1 of the inner portion 110 is listed in mm and also in optical power in Diopters. The "Center Fitting Range" (−1 to −2) shows that the inner portion can be fit with a covering having a curvature less than the ablated cornea, so as to promote epithelial regeneration. The covering can deflect and conform at least partially to the eye with the amount relative rigidity as described herein, for example an amount corresponding to a modulus of about 20 MPa and a thickness of about 200 um. The outer portion 120 can have a fitting range of about 1.5D, for example from about 41.5D to about 43D. The outer portion 120 corresponding to the unablated portion of the cornea can be flatter than the outer portion of the cornea, for example flatter within a range from about 0 to 1.5D. The flatter outer portion 120 can be coupled to a scleral portion 130, that can contact the conjunctiva and couple to the sclera. The scleral portion 130 can resist movement when the inner portion 110 and outer portion 120 provide the environment 100E to promote smooth regeneration of the epithelium.

TABLE C

Values to Identify Coverings.

| | Shield allocation | | | Pre-op | | Planned | | Shield | Shield | | |
|---|---|---|---|---|---|---|---|---|---|---|---|
| Subj ID | Sph (D) | Cyli (D) | SE (D) | CTR/Inner K (D) | Outer K (D) | Inner K (D) | SHIELD CODE | CTR/Inner K (D) | Outer K (D) | CTR diff (D) | Outer diff (D) |
| EMT OD | −1.25 | −0.5 | −1.50 | 42.9 | 42.2 | 41.40 | DZ | 39.50 | 41.50 | −1.90 | −0.70 |
| AGP OS | −1.25 | −0.25 | −1.38 | 42.0 | 41.7 | 40.63 | DZ | 39.50 | 41.50 | −1.13 | −0.20 |
| AML OD | −1.75 | −1.5 | −2.50 | 44.0 | 43.4 | 41.50 | EC | 40.50 | 43.00 | −1.00 | −0.40 |
| AML OS | −1.25 | −0.25 | −1.38 | 43.5 | 43.0 | 42.13 | EC | 40.50 | 43.00 | −1.63 | 0.00 |
| AMZ OD | −2.25 | −1 | −2.75 | 43.4 | 42.9 | 40.65 | DZ | 39.50 | 41.50 | −1.15 | −1.40 |
| AMZ OS | −2.25 | −0.5 | −2.50 | 43.4 | 43.1 | 40.90 | EA | 39.50 | 43.00 | −1.40 | −0.10 |
| BPS OD | −1.5 | −0.75 | −1.88 | 43.7 | 43.4 | 41.83 | EC | 40.50 | 43.00 | −1.33 | −0.40 |
| BPS OS | −2 | −0.25 | −2.13 | 44.6 | 44.0 | 42.48 | EC | 40.50 | 43.00 | −1.98 | −1.00 |
| DGU OD | −2.75 | −0.5 | −3.00 | 44.3 | 43.8 | 41.30 | EA | 39.50 | 43.00 | −1.80 | −0.80 |
| DGU OS | −2.5 | −0.5 | −2.75 | 44.2 | 43.8 | 41.45 | EA | 39.50 | 43.00 | −1.95 | −0.80 |
| JGG OD | −1 | −0.75 | −1.38 | 42.6 | 42.4 | 41.23 | DZ | 39.50 | 41.50 | −1.73 | −0.90 |
| JGG OS | −1.5 | −1 | −2.00 | 42.5 | 42.3 | 40.50 | DZ | 39.50 | 41.50 | −1.00 | −0.80 |
| KGC OD | −2.5 | −1.25 | −3.13 | 44.5 | 43.7 | 41.38 | EA | 39.50 | 43.00 | −1.88 | −0.70 |
| KGC OS | −3 | −1.25 | −3.63 | 44.1 | 43.5 | 40.48 | DY | 38.50 | 43.00 | −1.98 | −0.50 |
| RBT OD | −0.75 | −0.5 | −1.00 | 43.8 | 43.4 | 42.80 | EF | 41.50 | 43.00 | −1.30 | −0.40 |

TABLE C-continued

Values to Identify Coverings.

| | Shield allocation | | | Pre-op | | Planned | | Shield | Shield | | |
|---|---|---|---|---|---|---|---|---|---|---|---|
| Subj ID | Sph (D) | Cyli (D) | SE (D) | CTR/Inner K (D) | Outer K (D) | Inner K (D) | SHIELD CODE | CTR/Inner K (D) | Outer K (D) | CTR diff (D) | Outer diff (D) |
| RBT OS | −1.25 | 0 | −1.25 | 43.9 | 43.6 | 42.65 | EF | 41.50 | 43.00 | −1.15 | −0.60 |
| SVD OD | −2.5 | 0 | −2.50 | 44.1 | 43.6 | 41.60 | EC | 40.50 | 43.00 | −1.10 | −0.60 |
| SVD OS | −2 | 0 | −2.00 | 43.6 | 43.1 | 41.60 | EC | 40.50 | 43.00 | −1.10 | −0.10 |
| | −2.75 | −0.5 | −3.00 | 44.3 | 43.8 | 41.30 | EA | 39.50 | 43.00 | −1.80 | −0.80 |
| | −2.5 | −0.5 | −2.75 | 44.2 | 43.8 | 41.45 | EA | 39.50 | 43.00 | −1.95 | −0.80 |
| | −2.75 | −0.5 | −3.00 | 44.1 | 43.8 | 41.10 | EA | 39.50 | 43.00 | −1.60 | −0.80 |
| | −2.75 | 0 | −2.75 | 45.0 | 44.5 | 42.25 | ED | 40.50 | 44.50 | −1.75 | 0.00 |

Table C shows the covering assigned to each eye of each patient based on the pre-op refraction, the pre-op K's of the inner portion and the outer portion, the array of data corresponding to the fit coverings and the parameters of the coverings, and the logic steps to assign the covering based on the teachings described herein. For example, patient EMT is assigned a covering DZ based on the outer K of 42.2 and the planned inner K of 41.4 so as to provide a covering flatter than the ablated cornea by about 1.9 D. The "−" of the −1.9 D indicates that the covering corresponds to an optical power less than the ablated cornea by 1.9D. The outer difference of −0.70 D indicates that the outer unablated portion of the cornea is fit with a covering having a curvature less than the outer portion of the cornea. As the covering may comprise the scleral portion 130 having radius of curvature R1C, the movement of the covering on the eye can be resisted when the scleral portion contacts the conjunctiva to couple to the sclera.

While the covering can be identified in many ways, the covering can be identified based on the covering within a range of values and a sequence of logic steps, for example.

TABLE D

Inventory of coverings.

| SHIELD Code | Qty | Used |
|---|---|---|
| DV | 18 | 0 |
| DW | 9 | 0 |
| DX | 13 | 0 |
| DY | 16 | 1 |

TABLE D-continued

Inventory of coverings.

| SHIELD Code | Qty | Used |
|---|---|---|
| DZ | 16 | 6 |
| EA | 10 | 7 |
| EB | 12 | 0 |
| EC | 15 | 6 |
| ED | 17 | 1 |
| EF | 20 | 0 |
| EG | 18 | 3 |
| EG | 14 | 0 |

The inventory of coverings can show a number of coverings available for each covering and the number of coverings used, such that the health care provider can determine whether additional coverings should be ordered, for example.

The embodiments as described herein can be combined in many ways. As used herein like alphanumeric characters describe like structures, elements and methods and are interchangeable among the figures and supporting text to the full extent described and as understood by a person of ordinary skill in the art in accordance with the embodiments described herein.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

APPENDIX I

TABLE B1

| 14 mm multicurve designs | R1 center BC (D) | R1B1 5-7 mm K (D) | R1B2 7-9 mm K (D) | R1B3 9-11 mm K (D) | R1 C2 13.5-14 mm K (D) | SAG mm | DIA |
|---|---|---|---|---|---|---|---|
| Steep K | 36.5 | 43.50 | 42.25 | 39.50 | <12 mm BC (140 micron thick) | 3.1-3.4 | 13.8-14.1 mm |
| Medium | 36.5 | 42.00 | 40.75 | 38.25 | <12 mm BC (140 micron thick) | 3.1-3.4 | 13.8-14.1 mm |
| Flat K | 36.5 | 40.50 | 39.25 | 36.75 | <12 mm BC (140 micron thick) | 3.1-3.4 | 13.8-14.1 mm |
| Steep K | 38.5 | 44.25 | 43.00 | 40.25 | <12 mm BC (140 micron thick) | 3.1-3.4 | 13.8-14.1 mm |

TABLE B1-continued

| 14 mm multicurve designs | R1 center BC (D) | R1B1 5-7 mm K (D) | R1B2 7-9 mm K (D) | R1B3 9-11 mm K (D) | R1 C2 13.5-14 mm K (D) | SAG mm | DIA |
|---|---|---|---|---|---|---|---|
| Medium | 38.5 | 42.75 | 41.50 | 39.00 | <12 mm BC (140 micron thick) | 3.1-3.4 | 13.8-14.1 mm |
| Flat K | 38.5 | 41.25 | 40.00 | 37.50 | <12 mm BC (140 micron thick) | 3.1-3.4 | 13.8-14.1 mm |
| Steep K | 40.5 | 45.00 | 43.75 | 41.00 | <12 mm BC (140 micron thick) | 3.1-3.4 | 13.8-14.1 mm |
| Medium | 40.5 | 43.50 | 42.25 | 39.75 | <12 mm BC (140 micron thick) | 3.1-3.4 | 13.8-14.1 mm |
| Flat K | 40.5 | 42.00 | 40.75 | 38.25 | <12 mm BC (140 micron thick) | 3.1-3.4 | 13.8-14.1 mm |

TABLE B2

Flatter periphery design

| 14 mm multicurve designs | R1 Center BC (D) | R1B1 5-7 mm K (D) | R1B2 7-9 mm K (D) | R1B3 9-11 mm K (D) | R1 C2 13.5-14 mm K (D) | SAG (mm) | DIA |
|---|---|---|---|---|---|---|---|
| Steep K | 36.5 | 43.50 | 42.25 | 38.50 | <12 mm BC (140 micron thick) | 3.1-3.4 | 13.8-14.1 mm |
| Medium | 36.5 | 42.00 | 40.75 | 37.25 | <12 mm BC (140 micron thick) | 3.1-3.4 | 13.8-14.1 mm |
| Flat K | 36.5 | 40.50 | 39.25 | 35.75 | <12 mm BC (140 micron thick) | 3.1-3.4 | 13.8-14.1 mm |
| Steep K | 38.5 | 44.25 | 43.00 | 39.25 | <12 mm BC (140 micron thick) | 3.1-3.4 | 13.8-14.1 mm |
| Medium | 38.5 | 42.75 | 41.50 | 38.00 | <12 mm BC (140 micron thick) | 3.1-3.4 | 13.8-14.1 mm |
| Flat K | 38.5 | 41.25 | 40.00 | 36.50 | <12 mm BC (140 micron thick) | 3.1-3.4 | 13.8-14.1 mm |
| Steep K | 40.5 | 45.00 | 43.75 | 40.00 | <12 mm BC (140 micron thick) | 3.1-3.4 | 13.8-14.1 mm |
| Medium | 40.5 | 43.50 | 42.25 | 38.75 | <12 mm BC (140 micron thick) | 3.1-3.4 | 13.8-14.1 mm |
| Flat K | 40.5 | 42.00 | 40.75 | 37.25 | <12 mm BC (140 micron thick) | 3.1-3.4 | 13.8-14.1 mm |

TABLE B3

| Large shield (16 mm) multicurve designs | R1 center BC | R1B1 5-7 mm K (D) | R1B2 7-9 mm K (D) | R1B3 9-10.5 mm K (D) | 10.5-13 mm K (D) | 13-16 mm | SAG (mm) | DIA |
|---|---|---|---|---|---|---|---|---|
| Steep K | 36.5 | 43.50 | 42.25 | 39.50 | <10.0 mm/33.75 D | <14.5 mm/23 D | ≤3.6 | 15.6-16.1 mm |
| Medium | 36.5 | 42.00 | 40.75 | 38.25 | <10.0 mm/33.75 D | <14.5 mm/23 D | ≤3.6 | 15.6-16.1 mm |
| Flat K | 36.5 | 40.50 | 39.25 | 36.75 | <10.0 mm/33.75 D | <14.5 mm/23 D | ≤3.6 | 15.6-16.1 mm |
| Steep K | 38.5 | 44.25 | 43.00 | 40.25 | <10.0 mm/33.75 D | <14.5 mm/23 D | ≤3.6 | 15.6-16.1 mm |
| Medium | 38.5 | 42.75 | 41.50 | 39.00 | <10.0 mm/33.75 D | <14.5 mm/23 D | ≤3.6 | 15.6-16.1 mm |
| Flat K | 38.5 | 41.25 | 40.00 | 37.50 | <10.0 mm/33.75 D | <14.5 mm/23 D | ≤3.6 | 15.6-16.1 mm |
| Steep K | 40.5 | 45.00 | 43.75 | 41.00 | <10.0 mm/33.75 D | <14.5 mm/23 D | ≤3.6 | 15.6-16.1 mm |
| Medium | 40.5 | 43.50 | 42.25 | 39.75 | <10.0 mm/33.75 D | <14.5 mm/23 D | ≤3.6 | 15.6-16.1 mm |
| Flat K | 40.5 | 42.00 | 40.75 | 38.25 | <10.0 mm/33.75 D | <14.5 mm/23 D | ≤3.6 | 15.6-16.1 mm |

TABLE B4

| Multicurve CL designs | | R1 center BC (D) | R1B1 5-7 mm K (D) | R1B2 7-9 mm K (D) | R1B3 9-11 mm K (D) | R1C 13.5-14 mm K (D) | SAG (mm) | DIA |
|---|---|---|---|---|---|---|---|---|
| CL central curve 1 | Steep K | 40 | 41.75 | 39.00 | 39.00 | <12 mm BC (140 micron thick) | 3.1-3.4 | 13.8-14.1 mm |
| | Medium | 40.00 | 39.75 | 37.25 | 37.25 | <12 mm BC (140 micron thick) | 3.1-3.4 | 13.8-14.1 mm |
| | Flat K | 40.00 | 37.75 | 35.25 | 35.25 | <12 mm BC (140 micron thick) | 3.1-3.4 | 13.8-14.1 mm |
| CL central curve 2 | Steep K | 42.00 | 43.75 | 41.00 | 41.00 | <12 mm BC (140 micron thick) | 3.1-3.4 | 13.8-14.1 mm |
| | Medium | 42.00 | 41.75 | 39.25 | 39.25 | <12 mm BC (140 micron thick) | 3.1-3.4 | 13.8-14.1 mm |
| | Flat K | 42.00 | 39.75 | 37.25 | 37.25 | <12 mm BC (140 micron thick) | 3.1-3.4 | 13.8-14.1 mm |
| CL central curve 3 | Steep K | 44.000 | 44.75 | 42.00 | 42.00 | <12 mm BC (140 micron thick) | 3.1-3.4 | 13.8-14.1 mm |
| | Medium | 44.00 | 43.25 | 40.75 | 40.75 | <12 mm BC (140 micron thick) | 3.1-3.4 | 13.8-14.1 mm |
| | Flat K | 44.00 | 41.75 | 39.25 | 39.25 | <12 mm BC (140 micron thick) | 3.1-3.4 | 13.8-14.1 mm |
| CL central curve 4 | Steep K | 46.00 | 46.75 | 44.00 | 44.00 | <12 mm BC (140 micron thick) | 3.1-3.4 | 13.8-14.1 mm |
| | Medium | 46.00 | 45.25 | 42.75 | 42.75 | <12 mm BC (140 micron thick) | 3.1-3.4 | 13.8-14.1 mm |
| | Flat K | 46.00 | 43.75 | 41.25 | 41.25 | <12 mm BC (140 micron thick) | 3.1-3.4 | 13.8-14.1 mm |

What is claimed is:

1. A method of treating an eye of a patient, the eye having a cornea, the method comprising:
   measuring the eye to determine data of the eye corresponding to an inner ablated portion of the cornea and an outer unablated portion of the cornea away from the ablated portion; and
   identifying a covering of a plurality of coverings to treat the eye based on the data of the eye and an array of data corresponding to the plurality of therapeutic coverings,
   wherein the covering comprises an inner covering portion and an outer covering portion, the inner covering portion contacting the inner ablated portion of the cornea and an outer covering portion contacting an unablated portion when placed on the cornea and wherein the inner covering portion prior to placement on the eye has a covering curvature no more than a curvature of the ablated portion of the cornea and wherein the outer covering portion comprises a curvature prior to placement on the eye no more than the outer unablated portion of the cornea and wherein the covering resists movement of the inner portion when placed on the eye, and
   wherein the inner portion of the covering comprises an amount of rigidity within a range from about 1E-4 to about 5E-4 (Pa*m^3) and the outer portion of the covering comprises an outer amount of rigidity less than the amount of rigidity of the inner portion.

2. The method of claim 1, further comprising placing the covering on the eye.

3. The method of claim 1 wherein the outer portion of the covering extends to a conjunctiva of the eye and couples to the sclera of the eye to resist movement of the inner portion.

4. The method of claim 1 wherein the inner portion of the covering prior to placement comprise a substantially uniform thickness and an amount of curvature corresponding to less optical power than the optical power of the ablated portion of the cornea, the amount of curvature of the inner portion prior to placement within a range from about −1D to about −3D relative to the ablated portion of the cornea.

5. The method of claim 4 wherein the inner covering deflects at least about 1D so as to conform at least partially to the ablation and promote smooth epithelial regeneration and vision.

6. The method of claim 1 wherein measuring the eye comprises determining a conjunctiva sag height, the conjunctiva sag height corresponding to a portion of a conjunctiva of the eye at a radial location away from a reference axis of the eye and wherein the covering comprises a covering sag height at a covering location corresponding to the radial location of the portion of conjunctiva and wherein the covering is identified such that the covering sag height is greater than the conjunctiva sag height.

7. The method of claim 6 wherein the covering is deflected at the covering location when the covering is placed on the eye.

8. The method of claim 6 wherein the conjunctiva sag height is determined based on a measurement of a sclera of the eye corresponding to the radial location.

9. The method of claim 1 wherein measuring the eye comprises determining a limbus sag height, the limbus sag height corresponding to a portion of a limbus of the eye at a radial location away from a reference axis of the eye and wherein the covering comprises a covering sag height at a covering location corresponding to the radial location of the portion of the limbus and wherein the covering is identified such that the covering sag height is no more than the limbus sag height.

10. The method of claim 9 wherein the covering is deflected a first amount at a first covering location corresponding to a portion of the conjunctiva when the covering is placed on the eye and wherein the covering is deflected a second amount at a second covering location corresponding to a portion of the limbus when the covering is placed on the eye, the second amount less than the first amount such that pressure from the covering to the limbus is inhibited.

11. The method of claim 1 wherein the covering comprises an inner portion having a hydrogel layer extending along a lower surface to contact the ablated portion and the unablated portion of the cornea and wherein the covering comprises an outer portion comprising a sticky tacky surface to contact the conjunctiva and inhibit movement of the covering when the inner portion contacts the cornea.

12. An apparatus to treat an eye, the apparatus comprising:
an input to receive data of the eye, the data of the eye corresponding to an inner ablated portion of the cornea and an outer unablated portion of the cornea away from the ablated portion;
an output; and
at least one processor coupled to the input and the output the at least one processor comprising at least one computer readable memory, the at least one computer readable memory having instructions to store an array of data corresponding to a plurality of therapeutic coverings and instructions to identify a covering of the plurality based on the array and the data of the eye corresponding to the inner ablated portion and the outer portion,
wherein the covering comprises an inner covering portion and an outer covering portion, the inner covering portion contacting the inner ablated portion of the cornea and an outer covering portion contacting an unablated portion when placed on the cornea and wherein the inner covering portion prior to placement on the eye has a covering curvature no more than a curvature of the ablated portion of the cornea and wherein the outer covering portion comprises a curvature prior to placement on the eye no more than the outer unablated portion of the cornea and wherein the covering resists movement of the inner portion when placed on the eye, and
wherein the inner portion of the covering comprises an amount of rigidity within a range from about 1E-4 to about 5E-4 (Pa*m^3) and the outer portion of the covering comprises an outer amount of rigidity less than the amount of rigidity of the inner portion.

13. The apparatus of claim 12 wherein the instructions are configured to identify a covering having an inner portion comprising a lower surface curvature flatter than the inner ablated portion of the eye to inhibit one or more irregularities of the epithelium.

14. The apparatus of claim 13 wherein the lower surface curvature of the identified covering is flatter prior to placement than the inner ablated portion of the eye by at least about 1D.

15. The apparatus of claim 13 wherein the inner portion of the covering comprises a substantially uniform thickness and the instructions are configured to identify a covering prior to placement corresponding to hyperopia of the eye to improve vision and inhibit an epithelial irregularity located on an inner portion of the ablation and corresponding to nearsightedness of the eye.

16. The apparatus of claim 15 wherein the instructions are configured to identify the covering to inhibit formation of the epithelial irregularity based on one or more of a modulus of the inner portion of the covering, a thickness of the inner portion of the covering, or an amount rigidity of the inner portion of the covering.

17. The apparatus of claim 12 further comprising the plurality of coverings.

18. The apparatus of claim 12 wherein the array of data comprises a plurality of unique identifiers corresponding to the plurality of coverings.

19. The apparatus of claim 18 wherein the plurality of unique identifiers corresponds to a rigidity of an inner portion of each of the plurality of coverings.

20. The apparatus of claim 18 wherein the plurality of unique identifiers comprises 10 or more unique identifiers corresponding to an amount rigidity of the inner portion of at least about 3E-4 Pa*m^3.

21. The apparatus of claim 18 wherein the array of data comprises a first dimension corresponding to the inner ablated portion and a second dimension corresponding to the outer portion away from the ablated portion.

22. The apparatus of claim 21 wherein the array comprises a table, the first dimension corresponding to rows of the table, the second dimension corresponding to columns of the table and wherein the plurality of unique identifiers is stored in the rows and the columns of the table.

23. The apparatus of claim 21 wherein the display is visible to the user and the instructions are configured to show the unique identifier on the display.

24. The apparatus of claim 12, wherein the instructions are configured to receive a conjunctiva sag height, the conjunctiva sag height corresponding to a portion of a conjunctiva of the eye at a radial location away from a reference axis of the eye and wherein the instructions are configured such that the identified covering comprises a covering sag height at a covering location corresponding to the radial location of the portion of conjunctiva and wherein the instructions are configured such that the covering sag height is greater than the conjunctiva sag height.

25. The apparatus of claim 24 wherein the covering comprises an inner portion having a hydrogel layer extending along a lower surface to contact the ablated portion and the unablated portion of the cornea and wherein the covering comprises an outer portion at the covering location comprising a sticky tacky surface to contact the conjunctiva and inhibit movement of the covering when the inner portion contacts the cornea.

26. The apparatus of claim 25 wherein the inner portion of the covering comprises a low water content water inhibiting layer beneath the hydrogel layer and the outer portion of the covering at the covering location to contact the conjunctiva comprises a soft hydrophobic material.

27. The apparatus of claim 26 wherein the water inhibiting layer comprises silicone elastomer and the hydrogel layer comprises silicone hydrogel.

28. The apparatus of claim 24 wherein instructions are configured such that the identified covering is deflected at the covering location when the covering is placed on the eye.

29. The apparatus of claim 24 wherein the instructions are configured to receive the conjunctiva sag height based on a measurement of a sclera of the eye corresponding to the radial location.

30. The apparatus of claim 12, wherein the instructions are configured to receive a measurement the eye corresponding to a limbus sag height, the limbus sag height corresponding to a portion of a limbus of the eye at a radial location away from a reference axis of the eye and wherein the instructions are configured such that the covering comprises a covering sag height at a covering location corresponding to the radial location of the portion of limbus and wherein the instructions are configured such that the covering sag height is no more than the limbus sag height.

31. The apparatus of claim 12, wherein instructions are configured to identify the covering such that the identified covering is deflected a first amount at a first covering location corresponding to a portion of the conjunctiva when the covering is placed on the eye and wherein the instructions are configured to identify the covering such that the covering is deflected a second amount at a second covering location corresponding to a portion of the limbus when the covering is placed on the eye, the second amount less than the first amount such that pressure from the covering over the limbus is inhibited.

* * * * *